US012788264B2

(12) United States Patent
Lee et al.

(10) Patent No.: US 12,788,264 B2
(45) Date of Patent: Nov. 10, 2026

(54) SYSTEMS AND METHODS FOR OPTICAL WAVEGUIDES FOR HIGH EFFICIENCY AND HIGH QUALITY BIOSENSING OF SHALLOW ARTERIAL BEDS

(71) Applicant: Lumina Health, Inc., Allston, MA (US)

(72) Inventors: Daniel Lee, Boston, MA (US); Gregory Kaiser, Boston, MA (US); Richard Moyer, Boston, MA (US); Paul Jin, Boston, MA (US)

(73) Assignee: Lumina Health, Inc., Allston, MA (US)

( * ) Notice: Subject to any disclaimer, the term of this patent is extended or adjusted under 35 U.S.C. 154(b) by 0 days.

(21) Appl. No.: 18/741,607

(22) Filed: Jun. 12, 2024

(65) Prior Publication Data

US 2025/0380881 A1 Dec. 18, 2025

(51) Int. Cl.
*A61B 5/026* (2006.01)
*A61B 5/00* (2006.01)

(52) U.S. Cl.
CPC ............ *A61B 5/0261* (2013.01); *A61B 5/002* (2013.01); *A61B 5/6815* (2013.01); *A61B 5/7264* (2013.01); *A61B 5/7405* (2013.01)

(58) Field of Classification Search
CPC ..... A61B 5/0261; A61B 5/6815; A61B 5/002; A61B 5/7264; A61B 5/7405
See application file for complete search history.

(56) References Cited

U.S. PATENT DOCUMENTS

| | | | | |
|---|---|---|---|---|
| 7,477,924 | B2 * | 1/2009 | Chin | A61B 5/02438 600/323 |
| 8,700,111 | B2 * | 4/2014 | LeBoeuf | A61B 5/11 600/310 |
| 8,923,941 | B2 * | 12/2014 | LeBoeuf | A61B 5/0816 600/310 |
| 9,794,653 | B2 * | 10/2017 | Aumer | G08B 21/18 |
| 10,219,709 | B2 | 3/2019 | Basu | |
| 10,820,814 | B2 * | 11/2020 | Tsai | A61B 5/14551 |
| 11,266,320 | B2 | 3/2022 | Block et al. | |
| 11,330,993 | B2 | 5/2022 | Basu | |

(Continued)

FOREIGN PATENT DOCUMENTS

| | | | |
|---|---|---|---|
| EP | 3128761 | A1 | 2/2017 |
| WO | 2013003077 | A2 | 1/2013 |

OTHER PUBLICATIONS

P. Burton, T. Powers, J. Chalupper; "A New Era of Form and Function," The Hearing Review, Aug. 8, 2008; https://hearingreview.com/hearing-products/hearing-aids/bte/a-new-era-of-form-and-function.

*Primary Examiner* — Oommen Jacob
(74) *Attorney, Agent, or Firm* — Scale LLP

(57) ABSTRACT

The disclosed wearable photoplethysmography system is designed to be placed at a target location on a user. The system includes an emitter configured to emit photons, a photodiode, and a lens. The lens is designed to direct a majority of the photons within a specific exit angle range. When placed at the target location, the lens positions the emitter such that an arterial bed is within a path defined by the exit angle range. The arterial bed is located at a specific depth from the skin surface. The photons emitted by the emitter penetrate the user's tissue, interact with the arterial bed, and are then redirected to and detected by the photodiode.

17 Claims, 32 Drawing Sheets

(56) References Cited

U.S. PATENT DOCUMENTS

| | | | | |
|---|---|---|---|---|
| 11,471,103 | B2 | 10/2022 | LeBoeuf et al. | |
| 2003/0214717 | A1* | 11/2003 | Kaminsky | G02B 6/0065 349/64 |
| 2006/0274918 | A1* | 12/2006 | Amantea | G06V 40/19 382/117 |
| 2008/0165017 | A1* | 7/2008 | Schwartz | A61B 5/486 600/324 |
| 2010/0113948 | A1* | 5/2010 | Yang | A61B 5/02416 600/500 |
| 2010/0192952 | A1* | 8/2010 | Melker | A61B 5/6819 128/204.23 |
| 2011/0293822 | A1* | 12/2011 | Davidovits | B24B 13/00 451/178 |
| 2012/0106191 | A1* | 5/2012 | Duong | F21K 9/62 362/555 |
| 2012/0197093 | A1* | 8/2012 | LeBoeuf | A61B 5/7203 250/226 |
| 2013/0158372 | A1* | 6/2013 | Haisley | A61B 5/1455 600/310 |
| 2015/0257662 | A1* | 9/2015 | Lee | A61B 5/7207 600/323 |
| 2016/0058309 | A1 | 3/2016 | Han | |
| 2017/0000350 | A1* | 1/2017 | Kwon | A61B 5/02427 |
| 2017/0078780 | A1* | 3/2017 | Qian | H04R 1/1016 |
| 2017/0164848 | A1 | 6/2017 | Nadeau et al. | |
| 2018/0177416 | A1* | 6/2018 | Church | A61B 5/6814 |
| 2020/0229767 | A1* | 7/2020 | Eletr | A61B 5/14552 |
| 2022/0061669 | A1 | 3/2022 | Caizzone et al. | |
| 2023/0039857 | A1* | 2/2023 | Hayes-Gill | A61B 5/277 |
| 2023/0130889 | A1* | 4/2023 | Glenn | A61B 5/14552 600/324 |
| 2024/0407722 | A1* | 12/2024 | Monti | A61B 5/6835 |
| 2024/0423487 | A1* | 12/2024 | Brooks | A61B 5/02125 |

* cited by examiner

SYSTEMS AND METHODS FOR OPTICAL WAVEGUIDES FOR HIGH EFFICIENCY AND HIGH QUALITY BIOSENSING OF SHALLOW ARTERIAL BEDS

TECHNICAL FIELD

Various aspects of the present disclosure relate generally to systems and methods for biosensing and, more particularly, to systems and methods for biosensing using a wearable.

BACKGROUND

Poor Cerebral Blood Flow (CBF) is a major public health concern, especially for the elderly. Poor Cerebral Blood Flow most often occurs when a transition to standing causes a reduction of blood flow to the head. Some known diseases, conditions, and syndromes that cause Poor Cerebral Blood Flow upon standing include Orthostatic Hypotension (OH), Postural Orthostatic Tachycardia Syndrome (POTS), Orthostatic Cerebral Hypoperfusion Syndrome (OCHOs), Primary Cerebral Autoregulatory Failure (pCAF), Vasovagal Syncope, Carotid Sinus Sensitivity, hypovolemia, drug-induced hypotension, arrhythmias, vascular stenosis, aortic stenosis, Ehlers-Danlos Syndrome, Multiple Sclerosis, Multiple System Atrophy, Parkinson's, dementia, as well as various other neurological disorders that compromise the autonomic system (dysautonomias). Such loss of blood flow leads to debilitating dizziness that reduce quality of life. Blood flow sometimes drops low enough to also cause fainting which then leads to falling, a leading cause of death in the elderly. Approximately 1 in 4 adults over 65 years old fall once in a year causing 4 deaths/hour. Further, 800,000 people are hospitalized each year, and 3 million people are treated in emergency rooms each year, for head injury or hip fracture, requiring an estimated 50 billion dollars in reactive medical costs.

The treatments currently available to patients suffering from Poor Cerebral Blood Flow are limited. Pharmacological approaches are generally not applicable as many patients suffering from Poor Cerebral Blood Flow are also hypertensive and often already taking medications to lower their blood pressure. Thus, medications to increase blood pressure to reduce Poor Cerebral Blood Flow symptoms are contradictory. Mechanical interventions such as compression socks or airbag belts can be helpful but they have limited adoption due to the daily inconvenience of having to don and doff such interventions. Lifestyle modifications such as increased exercise, dietary changes, increased fluid intake, and slowed transitions to standing are helpful, but behavior change is burdensome for patients to adhere to, is hard to quantify the effective benefit relative to the costly effort, and often forgotten in practice. There is a strong need for an effective approach to managing Cerebral Blood Flow that patients will adopt and adhere to.

The present disclosure is directed to overcoming one or more of these above-referenced challenges.

SUMMARY OF THE DISCLOSURE

According to certain aspects of the disclosure, systems, methods, and computer readable memory are disclosed for biosensing using a wearable.

In some cases, a system for non-invasively measuring blood flow to a brain may include: a biometric sensor configured to be removably retained against an external surface of a skin portion of a target location at a head of a user; and a processor and a memory storing computer instructions. The system may be configured to: obtain, using the biometric sensor, biometric data relating to a blood flow waveform of one or more arteries near the target location; determine, based on the biometric data relating to the biometric data and/or blood flow waveform of the one or more arteries near the target location, a parameter indicative of a blood flow to a brain of the user; and display or transmit the parameter indicative of the blood flow to the brain of the user. The determining the parameter indicative of the blood flow to the brain of the user may include performing one or more computations using the biometric data and/or the blood flow waveform of the one or more arteries at the target location, the one or more computations being statistically determined by: obtaining sample target location biometric data relating to sample blood flow waveforms one or more sample arteries within ears of a plurality of sample subjects; obtaining sample brain biometric data relating to one or more brains of the plurality of sample subjects; for each of at least a subgroup of the plurality of sample subjects, pairing the sample ear biometric data to the sample brain biometric data obtained for a respective sample subject to create a plurality of sample data pairs; and based on the sample data pairs, determine one or more relationships between the sample ear biometric data and the sample brain biometric data.

In some cases, a computer-implemented method may include: obtaining, using a biometric sensor, biometric data relating to a blood flow waveform of one or more arteries near a target location of a user; determining, based on the biometric data relating to the blood flow waveform of the one or more arteries near the target location, a parameter indicative of a blood flow to a brain of the user; and displaying or transmitting the parameter indicative of the blood flow to the brain of the user; wherein determining the parameter indicative of the blood flow to the brain of the user comprises performing one or more computations using the biometric data and/or the blood flow waveform of the one or more arteries near the target location.

In some cases, a wearable photoplethysmography system (wearable PPG system) configured to be placed at a target location of a user may include: a wearable device configured to engage a body portion of the user; an emitter configured to emit photons having a wavelength of at least 590 nanometers; a photodiode; a lens cavity adjacent to the emitter; and at least one lens disposed within the lens cavity; wherein, when the wearable PPG system is placed at the target location of the user: the at least one lens is configured to direct at least 75% of the photons within an exit angle range between 30 and 90 degrees, the exit angle range being defined relative to a surface plane of the wearable PPG system; the wearable device disposes the emitter and lens such that an arterial bed is less than 5 millimeters from an exit surface of the lens and within a path defined by the exit angle range, the arterial bed being between 0.6 millimeters and 5 millimeters from an external surface of the skin of the user, the arterial bed comprising a portion of a posterior auricular artery, a superficial temporal artery, or a radial artery of the user; and at least a portion of the photons emitted by the emitter penetrates a tissue of the user, interacts with the arterial bed, and is then redirected to and detected by the photodiode.

In some cases, a method for monitoring blood flow in an arterial bed of a user using a wearable photoplethysmography system (wearable PPG system) may include: placing the wearable PPG system at a target location of the user such that an exit surface of a lens of the wearable PPG system is less than 5 millimeters from the arterial bed and the arterial bed is within a path defined by an exit angle range between 30 and 90 degrees relative to a surface plane, wherein the arterial bed is between 0.6 millimeters and 5 millimeters from an external surface of the skin of the user; emitting photons from an emitter of the wearable PPG system, wherein the photons have a wavelength of at least 590 nanometers; directing at least 75% of the photons within the exit angle range to the arterial bed of the user, wherein the photons interact with the arterial bed; and receiving, by a photodiode, redirected photons that have interacted with the arterial bed, wherein the photodiode detects the redirected photons.

In some cases, a wearable insert for positioning a biometric sensor at least partially within a cymba concha of an ear of a user may include: a first insert portion configured to abut an antihelix of the ear of the user; a second insert portion configured to be disposed at least partially within a cymba cavum of the ear; and a cavity configured to hold the biometric sensor; wherein, when the wearable insert is positioned within the ear: an engagement between the first insert portion and the antihelix applies a first retention force vector to the wearable insert, the first retention force vector being oriented at least partially medially; an engagement between the second insert portion and an ear portion against which the second insert portion abuts applies a second retention force vector to the wearable insert; and at least the first retention force vector and the second retention force vector retain the wearable insert such that the biometric sensor is pressed medially toward an external surface of a skin portion of the cymba concha of the ear.

In some cases, a method for providing a wearable insert for a user may include: scanning an ear of the user to obtain ear data; determining a two-dimensional rescaled or three-dimensional reconstructed model of the ear based on the ear data; selecting a wearable insert based on the two-dimensional or three-dimensional model; and providing the wearable insert and a biometric sensor to the user, wherein the wearable insert is configured to position the biometric sensor at least partially within a cymba concha of the ear; wherein the wearable insert includes a first insert portion configured to abut an antihelix of the ear, a second insert portion configured to be disposed at least partially within a cymba cavum of the ear, and a cavity configured to hold the biometric sensor.

Additional objects and advantages of the disclosed technology will be set forth in part in the description that follows, and in part will be apparent from the description, or may be learned by practice of the disclosed technology.

It is to be understood that both the foregoing general description and the following detailed description are exemplary and explanatory only and are not restrictive of the disclosed technology, as claimed.

BRIEF DESCRIPTION OF THE DRAWINGS

The accompanying drawings, which are incorporated in and constitute a part of this specification, illustrate various exemplary aspects and together with the description, serve to explain the principles of the disclosed technology.

DETAILED DESCRIPTION

Various aspects of the present disclosure relate generally to biosensing using a wearable.

Provided herein are methods, devices, systems, and platforms for detecting Cerebral Blood Flow (CBF) in real-time to prevent dizziness, fainting, and falls.

Technological solutions to helping with falling in the elderly have thus far been focused on fall detection, but fall detection is too late as the damage is already done. Rather than doing just fall detection, the methods described herein are focused on fall prevention through in-the-moment alerts made possible through continuously monitoring Cerebral Blood Flow.

1. PREVENTING PRESYNCOPE, SYNCOPE AND FALLS IN A SUBJECT

Provided herein is an exemplary method of preventing presyncope, syncope and falls in a subject comprising: receiving biometric data for the subject; aggregating and processing the biometric data; analyzing the data to detect or predict one or more of: poor cerebral blood flow, poor blood pressure, presyncope, syncope, and a fall event; and delivering one or more real-time messages to the subject pertaining to the identified detected or predicted event.

In some embodiments, the biometric data comprises one or more of: cerebral blood flow, blood pressure, blood volume, heart rate, heart rate variability, and blood oxygenation. In some embodiments, the biometric data is generated by a wearable device associated with the subject. In some embodiments, activity data is collected and comprises one or more of: motion, posture, change in posture, activity level, and type of activity. In some embodiments, the activity data is generated by a wearable device associated with the subject.

In some embodiments, analyzing the data comprises applying one or more artificial neural networks (ANNs). In some embodiments, analyzing the data comprises determining a posture or change in posture of the subject. In some embodiments, analyzing the data comprises one or more of: identifying trends pertaining to the biometric data of the subject, identifying trends pertaining to the activity data of the subject, identifying trends pertaining to detected or predicted poor cerebral blood flow of the subject, identifying trends pertaining to detected or predicated presyncope for the subject, identifying trends pertaining to detected or predicted syncope events for the subject, identifying trends pertaining to detected or predicted fall events for the subject. In some embodiments, the poor cerebral blood flow or fall risk threshold is based, at least in part, on one or more of: the biometric data of the subject, the activity data of the subject, demographic information of the subject, and a medical history of the subject. In some embodiments, trends are determined pertaining to the biometric data of the subject by comparing the biometric data with known medical patterns.

Figure 8:
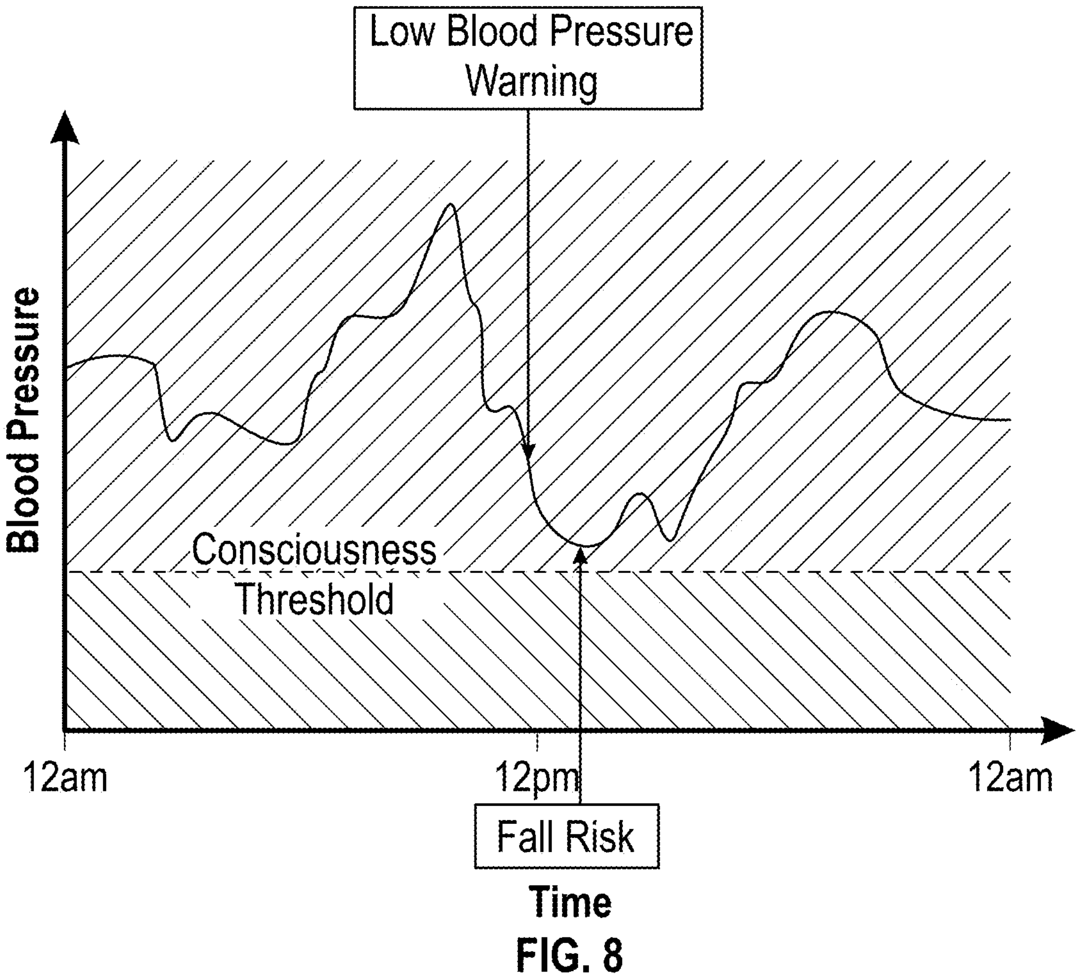
FIG. 8 shows a blood pressure vs time graph with consciousness warnings and alerts, per an embodiment herein.
Figure 9:
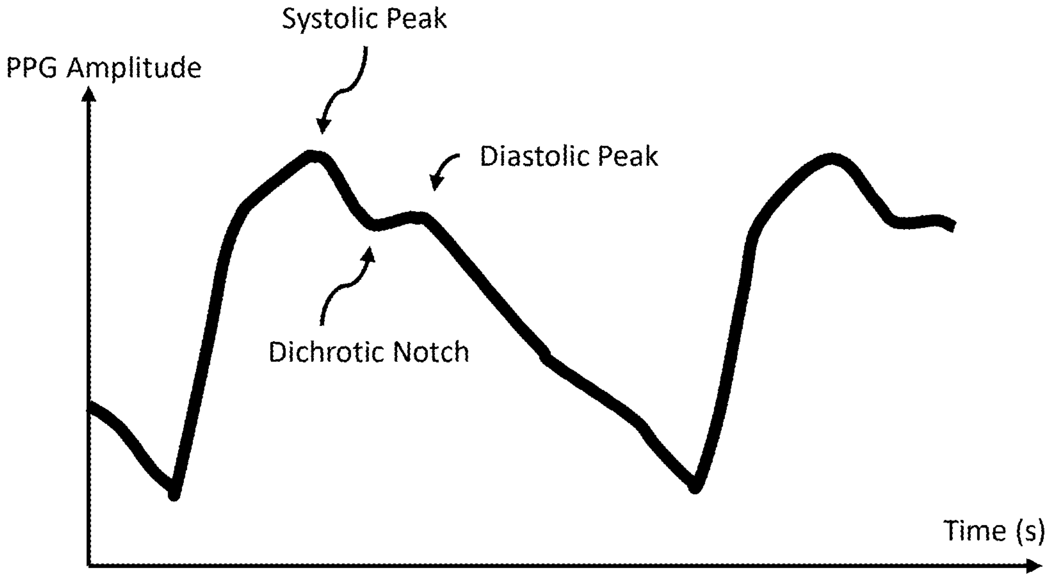
FIG. 9 shows a PPG measured amplitude vs time graph with labeled inflection systolic peak, dichrotic notch, and diastolic peak points, per an embodiment herein.
Figure 10:
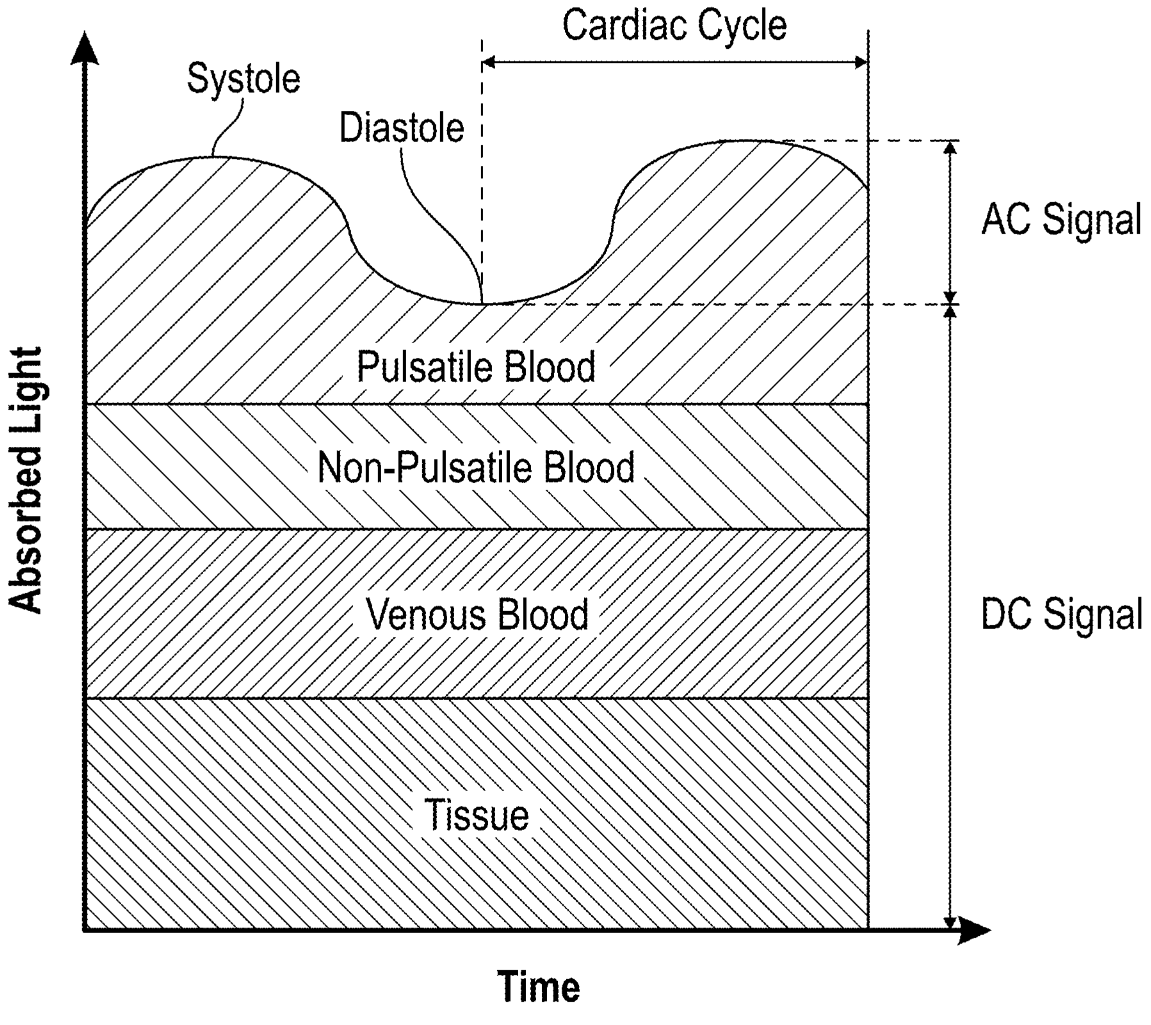
FIG. 10 shows a graph of absorption of the skin and corresponding DC and AC levels, per an embodiment herein.

In some embodiments, trends are determined by analyzing a blood pressure vs time graph of the biometric data. FIG. 8 shows a blood pressure vs time graph that demarcates a consciousness threshold and corresponding user warnings and alerts.

Figure 14:
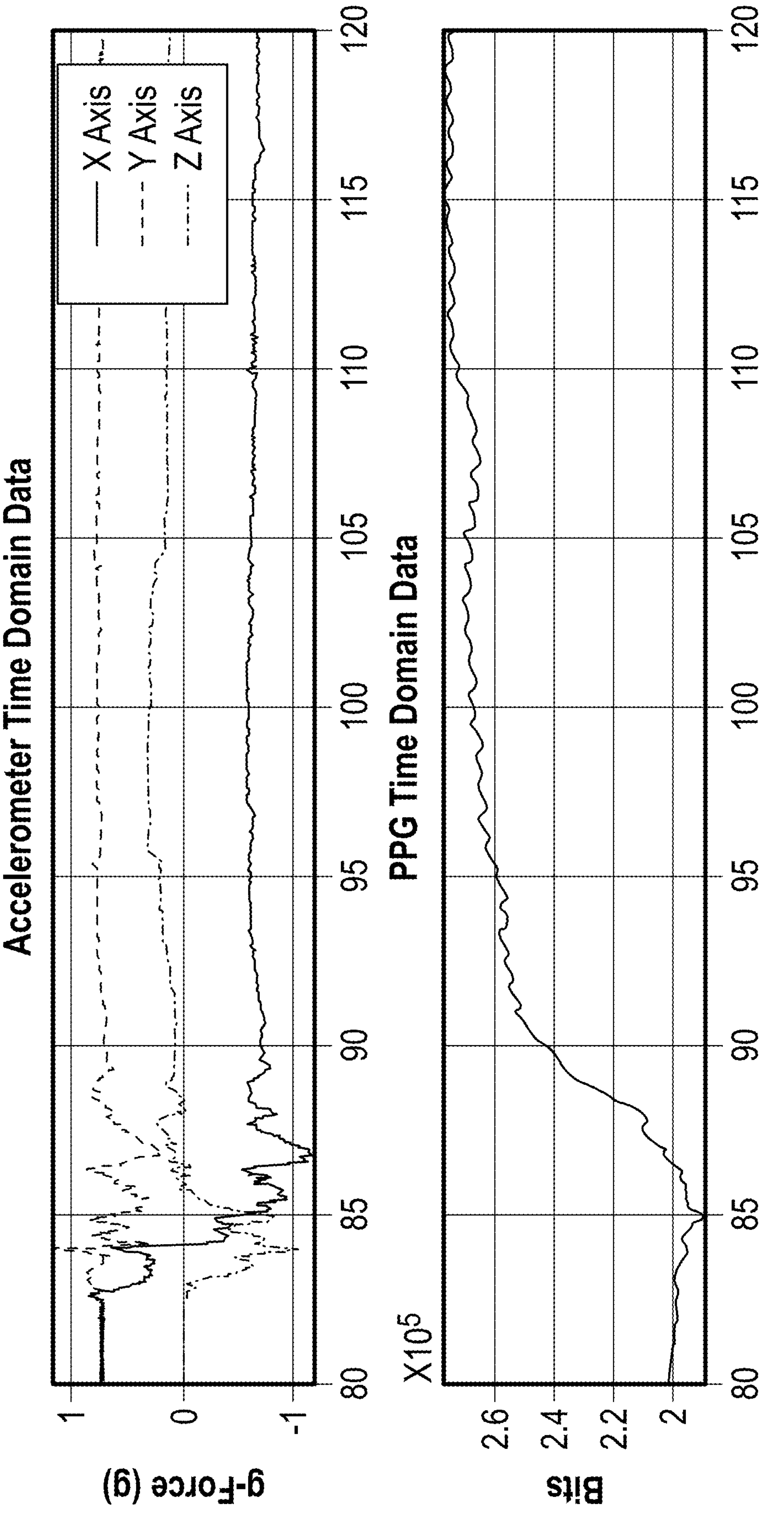
FIG. 14 shows a PPG Amplitude value read by a green light emitting diode (LED) during a transition of an elderly person from a supine to standing position, per an embodiment herein.
Figure 15:
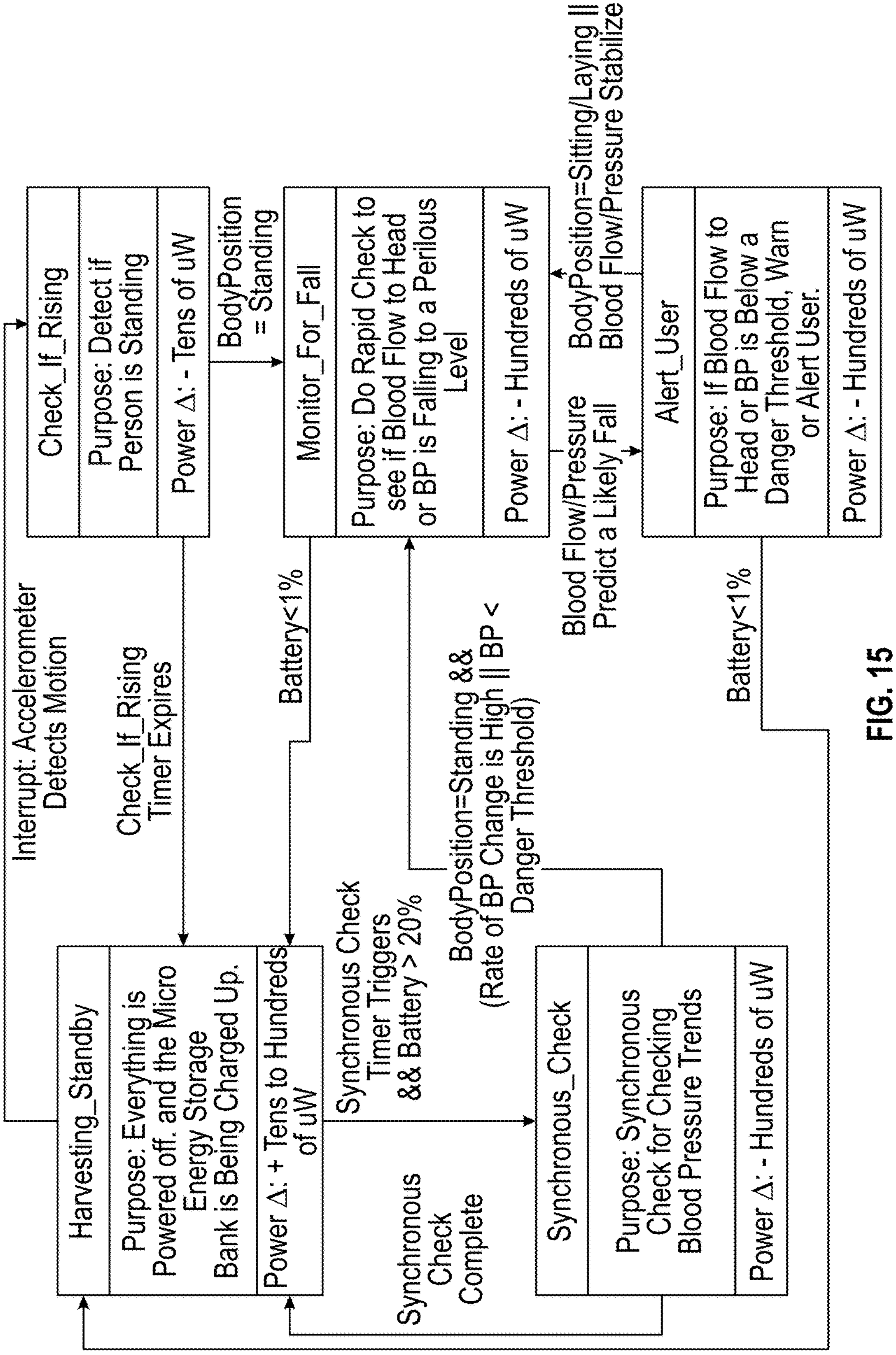
FIG. 15 shows another flowchart of the energy and data transfer in an exemplary in-ear system, per an embodiment herein.

In some embodiments, trends are determined by looking at the changes in cerebral blood flow upon postural changes. FIG. 14 shows a PPG amplitude value read by a green light emitting diode (LED), which reflects the relative level of blood flowing to the sensor location over a 40 second window. This was taken as an elderly subject transitioned from a supine to a standing position. The accelerometer data is provided to demarcate the timing of the postural change. You can see the dramatic change in cerebral blood flow as a result of the postural change. Younger healthy subjects do not exhibit as dramatic changes due to more elastic vasculature and better baroreceptor reflex function, amongst other age-related dynamics.

In some embodiments, the one or more real-time messages comprise an audio message delivered utilizing an acoustic transducer configured to deliver audio messages into the ear of the subject. In some embodiments, the device is configured to operate as an open ear audio device, and wherein the audio messages are delivered to the subject with low sound leakage perceived by others near the subject. In some embodiments, the method further comprises determining one or more applicable audio messages for the subject. In some embodiments, the one or more applicable audio messages for the subject comprise biometric feedback, a behavioral coaching recommendation, a warning, or an alert. In some embodiments, the biometric feedback or behavioral coaching recommendation may be conducted by reading to the subject one or more of their biometric parameters measured in that moment. In some embodiments, relative CBF percentage changes are read to the subject in real-time so the subject can determine if/when they should take action to avoid fainting. In some embodiments, blood volume levels are read to the subject so the subject can determine whether the subject should increase hydration and/or salt intake in order to reduce CBF instability.

Figure 7:
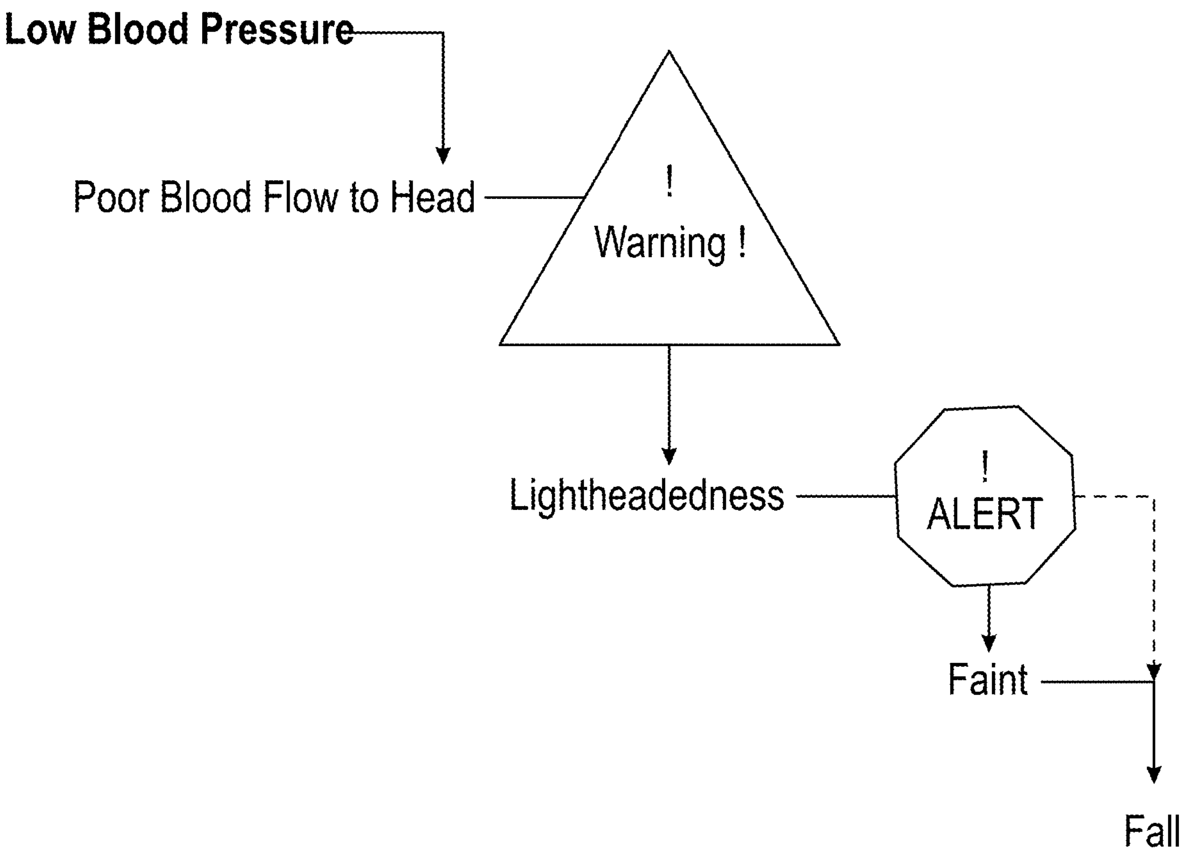
FIG. 7 shows an exemplary treatment method of in-the-moment warnings and alerts made possible through continuous monitoring of cerebral blood flow, per an embodiment herein.

FIG. 7 shows a treatment method of in-the-moment warnings and alerts made possible through continuous monitoring of cerebral blood flow. In some embodiments, the method comprises conveying the audio message in real-time. In some embodiments, the method comprises conveying the audio message in real-time, such that a period of time between the measurement of the sensor data, and the conveying of the audio message is at most about 1 microsecond, 5 microseconds, 10 microseconds, 50 microseconds, 100 microseconds, 500 microseconds, 1 millisecond, 5 millisecond, 10 millisecond, 50 millisecond, 100 millisecond, 500 millisecond, 1 second, 5 seconds, 10 seconds, or 50 seconds including increments therein. In some embodiments, as poor cerebral blood flow, poor blood pressure, presyncope, syncope, and fall events can develop quickly (e.g. within seconds) aggregating and processing the sensor data, detecting or predicting the event, and conveying the audio message in real-time greatly improves the odds of alerting the subject and/or a caretaker in time to prevent the event or further harm.

In some embodiments, the system provides intraday and interday interventions. In some embodiments, the intraday interventions, the interday interventions, or both are provided in an audio notification or alert, a visual notification or alert, a text notification, or any combination thereof. In some embodiments, the intraday intervention comprise a daily blood pressure readout, cerebral blood flow readout, high fall risk alert, fall detection alert, a caretaker notification or any combination thereof. Examples of interday user interventions are historical dashboards, trends, lifestyle tips, and disease detections.

Figure 6:
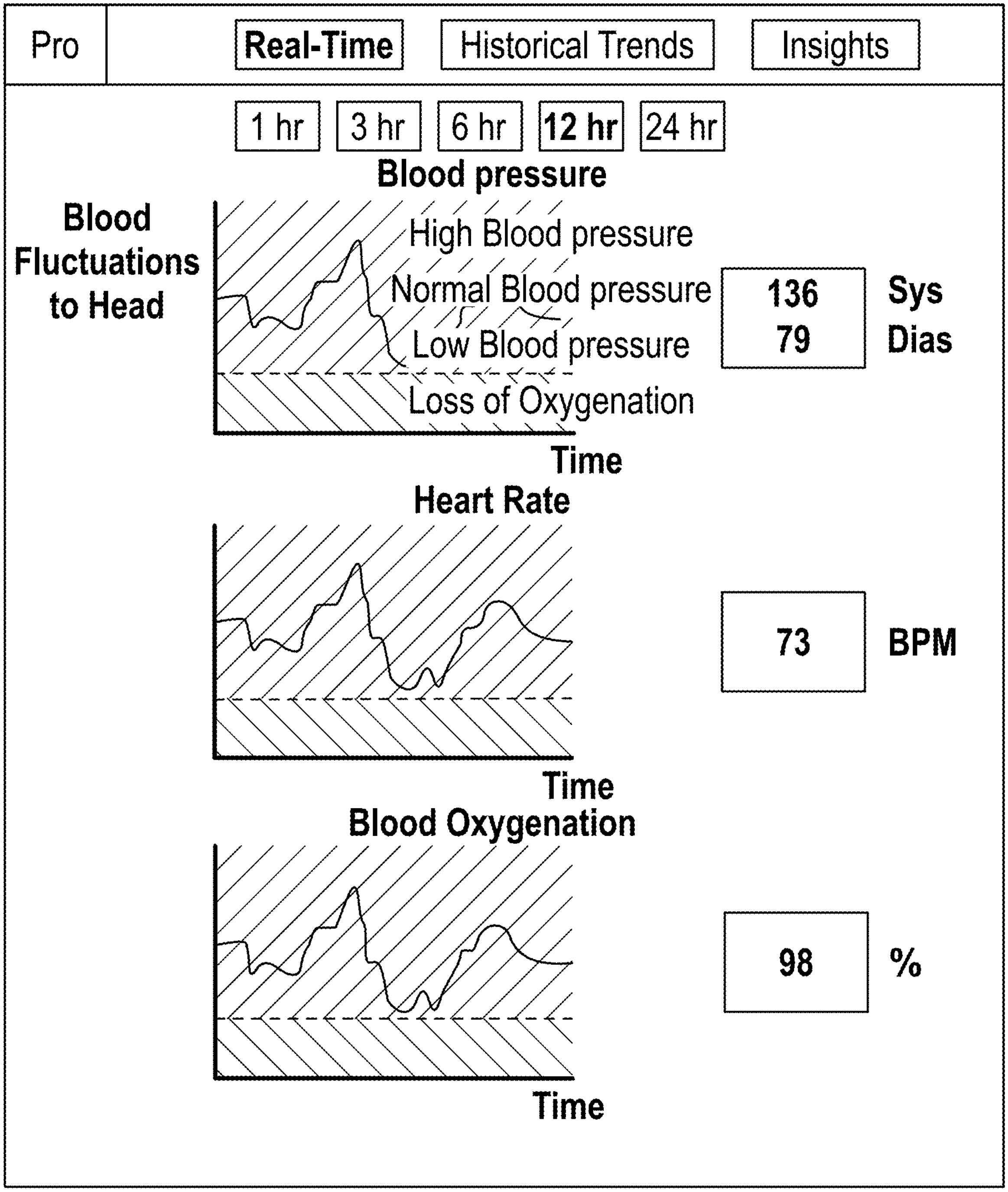
FIG. 6 shows an illustration of a graphical user interface (GUI) for displaying blood pressure, heart rate, and blood oxygenation by an in-ear device mechanism, per an embodiment herein.

In some embodiments, the one or more real-time messages comprise a visual message delivered utilizing a display of a device of the subject or a caretaker of the subject. In some embodiments, the method further comprises determining one or more applicable visual messages for the subject. In some embodiments, the one or more applicable visual messages for the subject comprise biometric feedback, a behavioral coaching recommendation, an alert, or a warning. In some embodiments, the method further comprises providing a subject health portal application allowing access to real-time and historical biometric data and activity data and trends for the subject. In some embodiments, the method further comprises providing a healthcare provider portal application allowing access to real-time and historical biometric data and activity data and trends for one or more subjects. FIG. 6 shows an illustration of a graphical user interface (GUI) for displaying blood pressure, heart rate, and blood oxygenation by an in-ear device.

1.A. Wearable Device for Preventing Presyncope, Syncope and Falls

Provided herein, per FIGS. 1-4 are exemplary wearable devices 100 for preventing presyncope, syncope and falls. In some embodiments, the device 100 comprises a biometric sensor 101, a movement sensor 102, a logic element 103, an acoustic transducer 104, a wireless communications transceiver 105, and a microcontroller 106. In some embodiments, the device 100 further comprises a housing containing the biometric sensor 101, the movement sensor 102, the logic element 103, the acoustic transducer 104, the wireless communications transceiver 105, the microcontroller 106, or any combination thereof. In some embodiments, the device 100 is configured to operate as an open ear audio device 100. In some embodiments, device 100 is configured to deliver audio messages to the subject with low sound leakage perceived by others near the subject. In some embodiments, the device 100 is configured to deliver the audio messages in real-time.

In some embodiments, the acoustic transducer 104 is configured to deliver audio messages into the ear of the subject. In some embodiments, the acoustic transducer 104 enables the device 100 to operate as an open ear audio device 100. In some embodiments, the acoustic transducer 104 delivers audio messages to the ear of the subject while at least a portion of the ear canal of the subject is unobstructed. In some embodiments, the acoustic transducer 104 delivers audio messages to the ear of the subject while the entire ear canal of the subject is unobstructed. In some embodiments, the entire device 100 is configured to be positioned outside the ear canal of the subject during delivery of the audio message. In some embodiments, maintaining an unobstructed ear canal enables the device 100 to be used without compromising the hearing of the subject.

In some embodiments, the acoustic transducer 104 enables the device 100 to operate with low sound leakage perceived by others near the subject. In some embodiments, the acoustic transducer 104 emits the audio message at a volume such that a subject (e.g. a subject without significant hearing disabilities) can hear and understand the audio message. In some embodiments, the acoustic transducer 104 emits the audio message at a frequency such that a subject (e.g. a subject without hearing disabilities) can hear and understand the audio message. In some embodiments, the acoustic transducer 104 emits the audio message at a volume such that another person (e.g. a person without hearing disabilities) within about 1, 2, 3, 4, 5, 6, 7, 8, 9, 10 or more feet from the subject is not able to hear or understand the audio message. In some embodiments, the acoustic transducer 104 emits the audio message at a frequency such that another person (e.g. a person without hearing disabilities) within about 1, 2, 3, 4, 5, 6, 7, 8, 9, 10 or more feet from the subject is not able to hear or understand the audio message. In some embodiments, the audio messages comprise one or more of: biometric feedback, a behavioral coaching recommendation, a warning, and an alert pertaining to one or more of: poor cerebral blood flow, poor blood pressure, presyncope, syncope, and a fall event. In some embodiments, the audio messages comprise a speech-based instruction regarding one or more of: biometric feedback, the behavioral coaching recommendation, the warning, and the alert pertaining to one or more of: poor cerebral blood flow, poor blood pressure, risk of syncope, and risk of falling. In some embodiments, the audio messages comprise an alarm or chime regarding one or more of: biometric feedback, the behavioral coaching recommendation, the warning, and the alert pertaining to one or more of: poor cerebral blood flow, poor blood pressure, risk of syncope, risk of falling.

In some embodiments, the biometric sensor 101 is configured to monitor at least one biometric parameter of the subject. In some embodiments, the biometric sensor 101 comprises an optical sensor. In some embodiments, the optical sensor comprises a photoplethysmography (PPG) sensor. In some embodiments, the at least one biometric parameter of the subject comprises one or more of: cerebral blood flow, blood pressure, blood volume, heart rate, heart rate variability, or blood oxygenation. In some embodiments, the wearable device 100 further comprises a temperature sensor. In some embodiments, the at least one biometric parameter of the subject comprises temperature.

In some embodiments, the movement sensor 102 is configured to monitor at least one activity parameter of the subject. In some embodiments, the movement sensor 102 comprises at least one accelerometer. In some embodiments, the at least one activity parameter of the subject comprises an activity level. In some embodiments, the activity level is associated with a movement frequency of movement sensor 102, a velocity of movement sensor 102, an acceleration of the movement sensor 102, or any combination thereof. In some embodiments, the activity level is associated with a relative movement frequency between two or more movement sensors 102, a relative velocity of movement between two or more movement sensors 102, a relative acceleration of the movement sensor 102 between two or more movement sensors 102, or any combination thereof.

In some embodiments, the microcontroller 106 is configured to aggregate and process sensor data. In some embodiments, the microcontroller 106 is configured to pass processed data to the wireless communications transceiver 105. In some embodiments, the microcontroller 106 is further configured to analyze the data to detect or predict one or more of: poor cerebral blood flow, poor blood pressure, presyncope, syncope, and a fall event. In some embodiments, the change in posture is sitting up from a laying posture, standing from a sitting posture, standing from a kneeling posture, standing from a squatting posture, or standing upright from a bent standing posture. In some embodiments, the microcontroller 106 is configured to determine an audio message content based on the processed data, the detected or predicted presyncope event, the detected or predicted syncope, the detected or predicted fall event, or any combination thereof. In some embodiments, a neural net model determines a cerebral blood flow metric, sitting blood pressure, a standing blood pressure, a laying blood pressure, a hypertension classification, an orthostatic hypotension classification, a user dizziness score, a syncope risk score, or any combination thereof.

In some embodiments, the microcontroller 106 is configured to aggregate and process sensor data, detect or predict an event, and direct the acoustic transducer 104 to convey the audio message in real-time. In some embodiments, the microcontroller 106 is configured to aggregate and process sensor data, detect or predict an event, and direct the acoustic transducer 104 to convey the audio message in real-time, such that a period of time between the measurement of the sensor data, and the conveying of the audio message by the acoustic transducer 104 is at most about 1 millisecond, 5 millisecond, 10 millisecond, 50 millisecond, 100 millisecond, 500 millisecond, 1 second, 5 seconds, 10 seconds, or 50 seconds including increments therein. In some embodiments, as poor cerebral blood flow, poor blood pressure, presyncope, syncope, and fall events can develop quickly (e.g. within seconds), aggregating and processing the sensor data, detecting or predicting the event, and directing the acoustic transducer 104 to convey the audio message in real-time greatly improves the odds of alerting the subject and/or a caretaker in time to prevent the event or further harm.

In some embodiments, the microcontroller 106 is further configured to provide a visual message based on the detection and/or prediction of poor cerebral blood flow, poor blood pressure, presyncope, syncope, a fall event, or any combination thereof. In some embodiments, the microcontroller 106 controls a user interface to display the visual message. In some embodiments, the microcontroller utilizes the wireless communications transceiver 105 to communicate with an external device 108 that provides the user interface medium through which the visual message is delivered.

In some embodiments, the logic element 103 performs state management. In some embodiments, the state management enables a sleep state, a first wake state, or a second wake state of the device 100. In some embodiments, in the first wake state, the second wake state, or both, the device 100 performs synchronous monitoring of the subject. In some embodiments, the state management maintains the device 100 in a sleep state, shifts the device 100 to the first wake state intermittently, at a predefined interval, and shifts the device 100 to a second wake state. In some embodiments, the state management shifts the device 100 to the second wake state when the at least one activity parameter indicates a change in posture of the subject. In some embodiments, in the sleep state, the micro energy storage bank is charged. In some embodiments, in the first wake state and the second wake state, the micro energy storage bank powers operation of the biometric sensor 101, the movement sensor 102, the acoustic transducer 104, and the wireless communications transceiver 105. In some embodiments, the predefined interval is between about 1 minute to about 30 minutes. In some embodiments, the state management further comprises returning the device 100 to the sleep state after performing the synchronous or asynchronous monitoring of the subject for a monitoring period. In some embodiments, the monitoring period is between about 5 seconds to about 120 seconds. In some embodiments, in the first wake state or the second wake state, the biometric sensor 101 monitors the at least one biometric parameter of the subject at a rate of between about 1 Hz to about 200 Hz. In some embodiments, in the first wake state or the second wake state, the movement sensor 102 monitors the at least one activity parameter of the subject at a rate of between about 1 Hz to about 200 Hz.

In some embodiments, the wireless communications transceiver 105 utilizes a Near-Field Communication (NFC) protocol, Bluetooth, Bluetooth Low Energy, LoRa, or Wi-Fi. In some embodiments, the wireless communications transceiver 105 is configured to send data to an external device 108 and receive data from the external device 108. In some embodiments, the external device 108 comprises a local base station, a mobile device of the subject, or at least one server.

In some embodiments, the wearable device 100 further comprises a micro energy storage bank. In some embodiments, the micro energy storage bank comprises a supercapacitor or a micro battery. In some embodiments, the micro energy storage bank has a maximum capacity of no more than 10 milli-Watt-hour (mWh). In some embodiments, the wearable device 100 further comprises an energy harvesting element configured to charge the micro energy storage bank. In some embodiments, the energy harvesting element compromises a photovoltaic cell configured to harvest energy from natural daylight, interior lighting, and infrared emitters. In some embodiments, the energy harvesting element comprises a RF antenna configured to harvest energy from the environment of the device 100. In some embodiments, the energy harvesting element comprises a thermoelectric generator configured to harvest energy from body heat of the subject. In some embodiments, the energy harvesting element comprises a piezoelectric material configured to harvest energy from motion of the subject. In some embodiments, a charging and/or discharging state of the device 100 is configured to optimize energy harvesting and energy usage periods.

Figure 1:
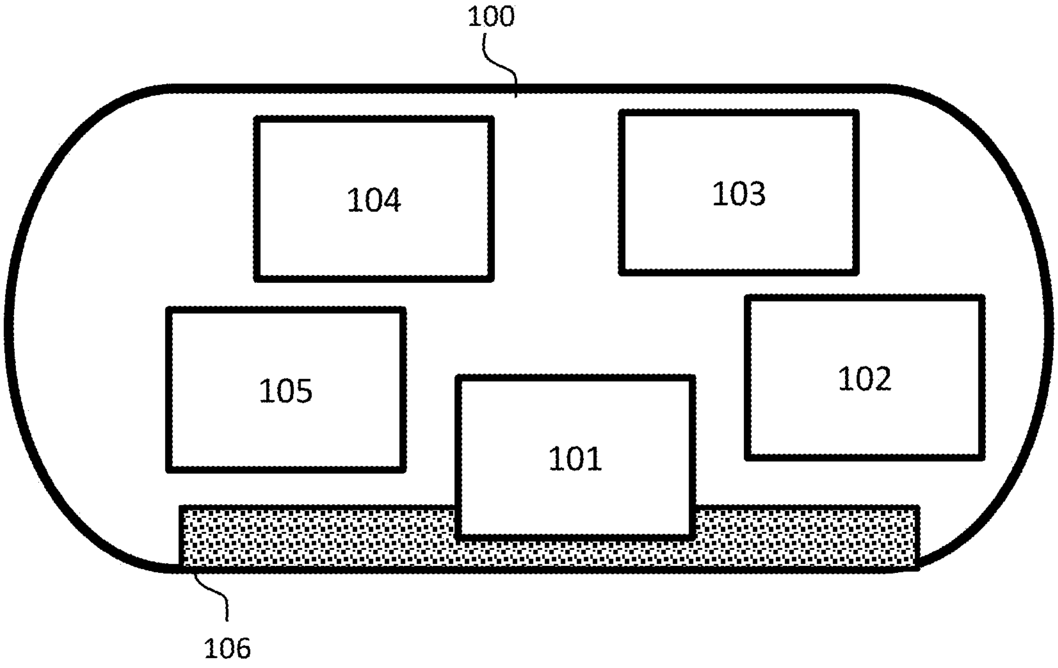
FIG. 1 shows a diagram of the components of an exemplary in-ear device, per an embodiment herein.
Figure 2:
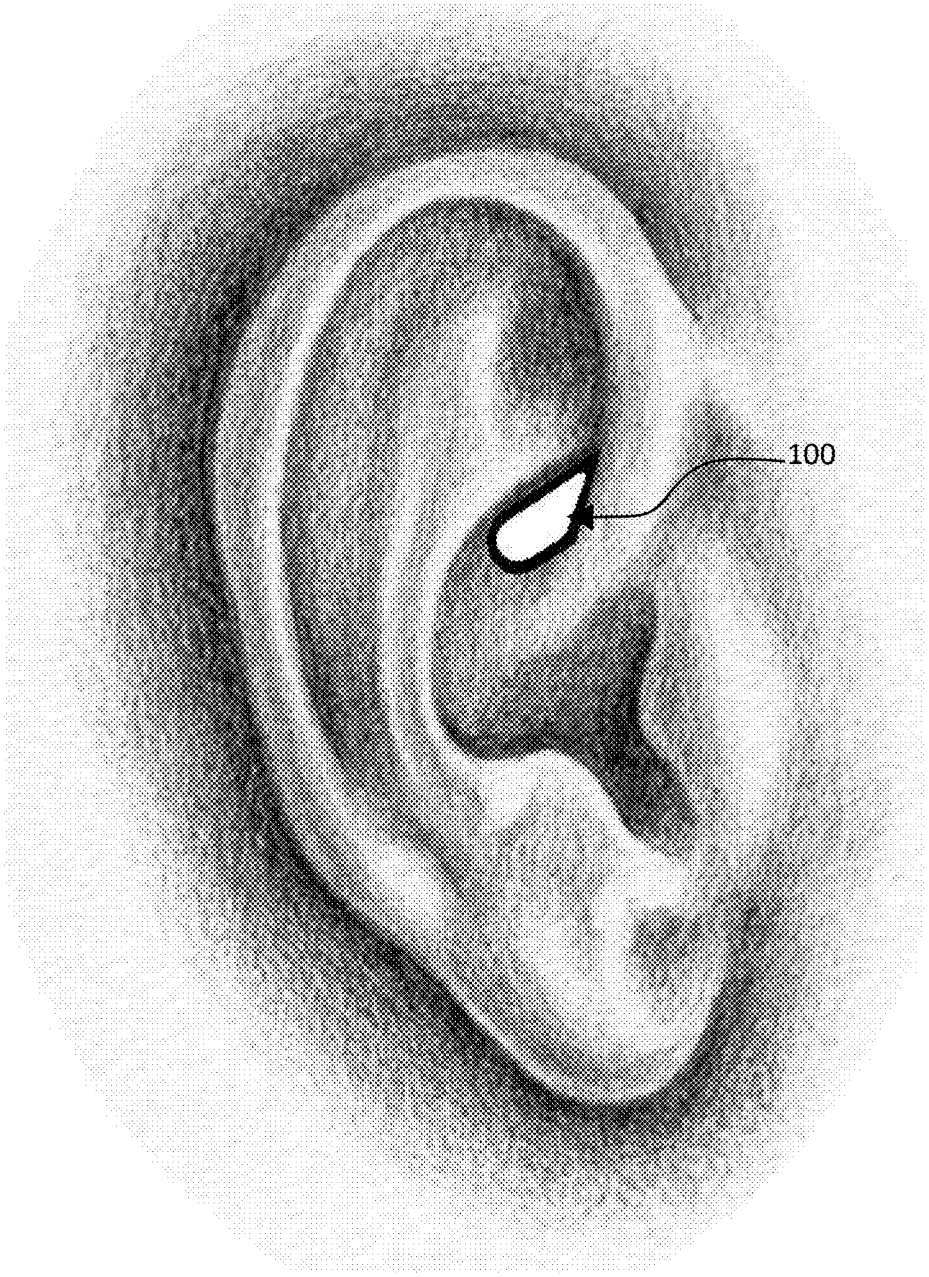
FIG. 2 shows an illustration of an exemplary in-ear device, per an embodiment herein.
Figure 3:
FIG. 3 shows an image of an exemplary in-ear device, per an embodiment herein.
Figure 4A:
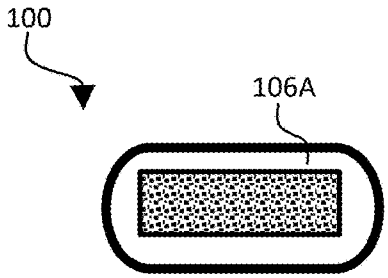
FIG. 4A shows an illustration of an exemplary in-ear device with a first attachment mechanism, per an embodiment herein.
Figure 4B:
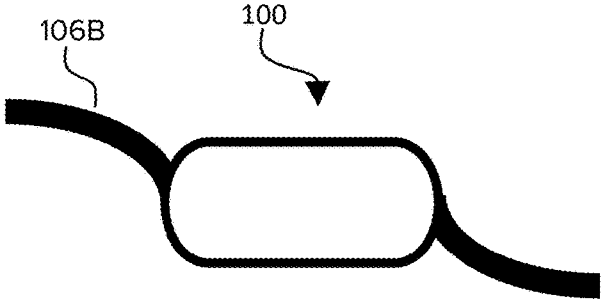
FIG. 4B shows an illustration of an exemplary in-ear device with a second attachment mechanism, per an embodiment herein.
Figure 4C:
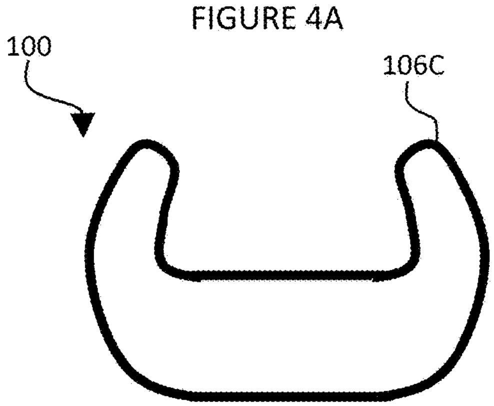
FIG. 4C shows an illustration of an exemplary in-ear device with a third attachment mechanism, per an embodiment herein.
Figure 4D:
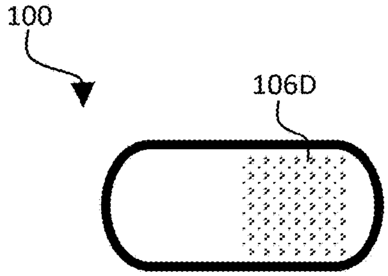
FIG. 4D shows an illustration of an exemplary in-ear device with a fourth attachment mechanism, per an embodiment herein.
Figure 4E:
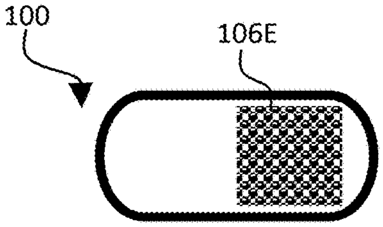
FIG. 4E shows an illustration of an exemplary in-ear device with a fifth attachment mechanism, per an embodiment herein.
Figure 4F:
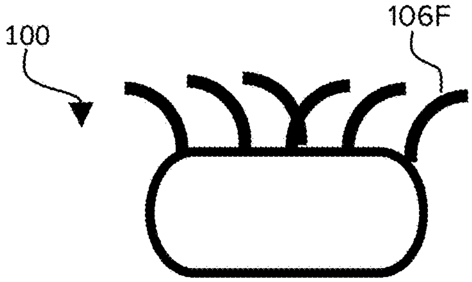
FIG. 4F shows an illustration of an exemplary in-ear device with a sixth attachment mechanism, per an embodiment herein.
Figure 4G:
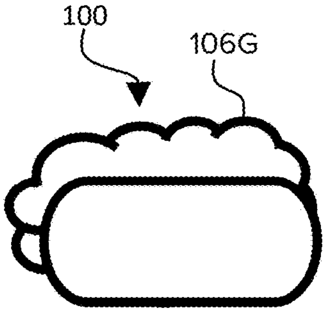
FIG. 4G shows an illustration of an exemplary in-ear device with a seventh attachment mechanism, per an embodiment herein.

In some embodiments, per FIGS. 1 and 4A, the wearable device 100 further comprises an attachment mechanism 106A for attaching the device 100 to the subject. In some embodiments, the device 100 is adapted to attach to an auricle of the subject. In some embodiments, the device 100 is adapted to attach to the auricle of the subject at the cymba concha, scapha, triangular fossa, anti-helix, or inner surface of the helix of the subject. In some embodiments, the device 100 is adapted to attach to the auricle of the subject at the cymba concha of the subject. In some embodiments, per FIG. 4B, the attachment mechanism 106 comprises one or more elastomeric wings 106B. In some embodiments, per FIG. 4C, the attachment mechanism 106 is one or more elastomeric clips 106C. In some embodiments, per FIG. 4D, the attachment mechanism 106 is one or more elastomeric rough surface finishes 106D. In some embodiments, per FIG. 4E, the attachment mechanism 106 is one or more elastomeric suction cups 106E. In some embodiments, per FIG. 4F, the attachment mechanism 106 is a set of elastomeric appendages 106F. In some embodiments, per FIG. 4G, the attachment mechanism 106 is an elastomeric mold 106G.

In some embodiments, the device 100 has a longest dimension of at most about 15 mm. In some embodiments, the device 100 has a longest dimension of at most about 12 mm. In some embodiments, the small size of the device 100 enables its use in the auricle of the subject while maintaining an open ear canal of the patient.

1.B. System for Preventing Presyncope, Syncope and Falls in a Subject

Another aspect provided herein is a system for preventing presyncope, syncope and falls in a subject. In some embodiments, the system comprises the wearable device as described in any one or more embodiment herein, and a local base station.

In some embodiments, the local base station comprises a wireless communications transceiver and a network interface. In some embodiments, the wireless communications transceiver is configured to send data to the wearable device, receive data from wearable device, or both. In some embodiments, the network interface is configured to provide connectivity to a computer network. In some embodiments, the local base station further comprises a wireless power transmitter (WPT) comprising an RF energy transmission antenna. In some embodiments, the local base station further comprises a wireless power transmitter (WPT) comprising infrared light emitters. In some embodiments, the infrared light emitters comprise infrared light-emitting diodes (LEDs). In some embodiments, the local base station further comprises an acoustic transducer for broadcasting audio messages. In some embodiments, the local base station further comprises a screen for displaying biometric information and notifications. In some embodiments, the wearable device further comprises an attachment mechanism for attaching the device to an auricle of the subject. In some embodiments, the local base station further comprises one or more processors configured to transmit an alert via one or more of: SMS, MMS, email, telephone, voice mail, and social media. In some embodiments, the computer network comprises the internet.

Figure 5:
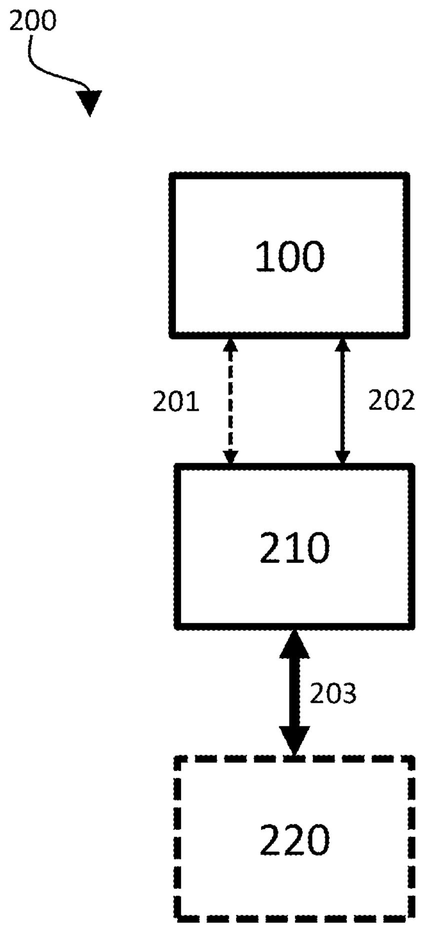
FIG. 5 shows a flowchart of the energy and data transfer in an exemplary in-ear system, per an embodiment herein.

In some embodiments, the local base station 210 comprises a wireless communications transceiver and a network 220 interface. In some embodiments, per FIG. 5., the wireless communication transceiver is configured to send a first data 201 to the in-ear device 100 and receive a first data 201 from the in-ear device 100. In some embodiments, the network interface is configured to provide connectivity to a computer network 220. In some embodiments, the network interface is configured to transmit a second data 203 to the computer network 220. In some embodiments, the first data 201, the second data 203, or both comprise the biometric parameter, the activity parameter, or both. In some embodiments, the first data 201, the second data 203, or both are based on the biometric parameter, the activity parameter, or both. In some embodiments, a transmission/reception bandwidth of the second data 203 is greater than a transmission/reception bandwidth of the first data 201. In some embodiments, power provided to the local base station 210 by a battery or a wall outlet enables the transmission/reception bandwidth of the second data 203 to be greater than a transmission/reception bandwidth of the first data 201. In some embodiments, the difference between the transmission/reception bandwidth of the second data 203 and the first data 201 reduces the power required by the in-ear device 100 to communicate with the computer network 220. In some embodiments, the physiological trends comprise intraday and interday trends of cerebral blood flow, blood pressure, presyncope risk, syncope risk, and fall risk.

1.C. Platforms for Predicting Presyncope, Syncope and Fall Events in a Subject

Another aspect provided herein is a platform for predicting presyncope, syncope and fall events in a subject. In some embodiments, the platform comprises the wearable device, as described in any one or more embodiment herein, the local base station, as described in any one or more embodiment herein, and a cloud computing back-end.

In some embodiments, the network interface is configured to provide connectivity to the cloud computing back-end; and a cloud computing back-end comprising: a module configured to store and analyze the biometric and activity data of the subject to identify trends and provide resulting biometric feedback and behavioral coaching recommendations; and a module configured to determine one or more applicable audio messages for the subject. In some embodiments, the computer network comprises the internet. In some embodiments, the analysis comprises one or more of: identifying trends pertaining to the biometric data of the subject, identifying trends pertaining to the activity data of the subject, identifying trends pertaining to cerebral blood flow for the subject, identifying trends pertaining to predicted or actual presyncope events for the subject, identifying trends pertaining to predicted or actual syncope events for the subject, or identifying trends pertaining to predicted or actual fall events for the subject. In some embodiments, the analysis is further based on an age, gender, height, weight, existing diagnoses, comorbid conditions, number of previous falls, medication, or any combination thereof of the subject. In some embodiments, the analysis receives user data via a user survey. In some embodiments, the user survey conducts a question and response that collects age, gender, height, weight, existing diagnoses, comorbid conditions, number of previous falls, medications, or any combination thereof.

Figure 16:
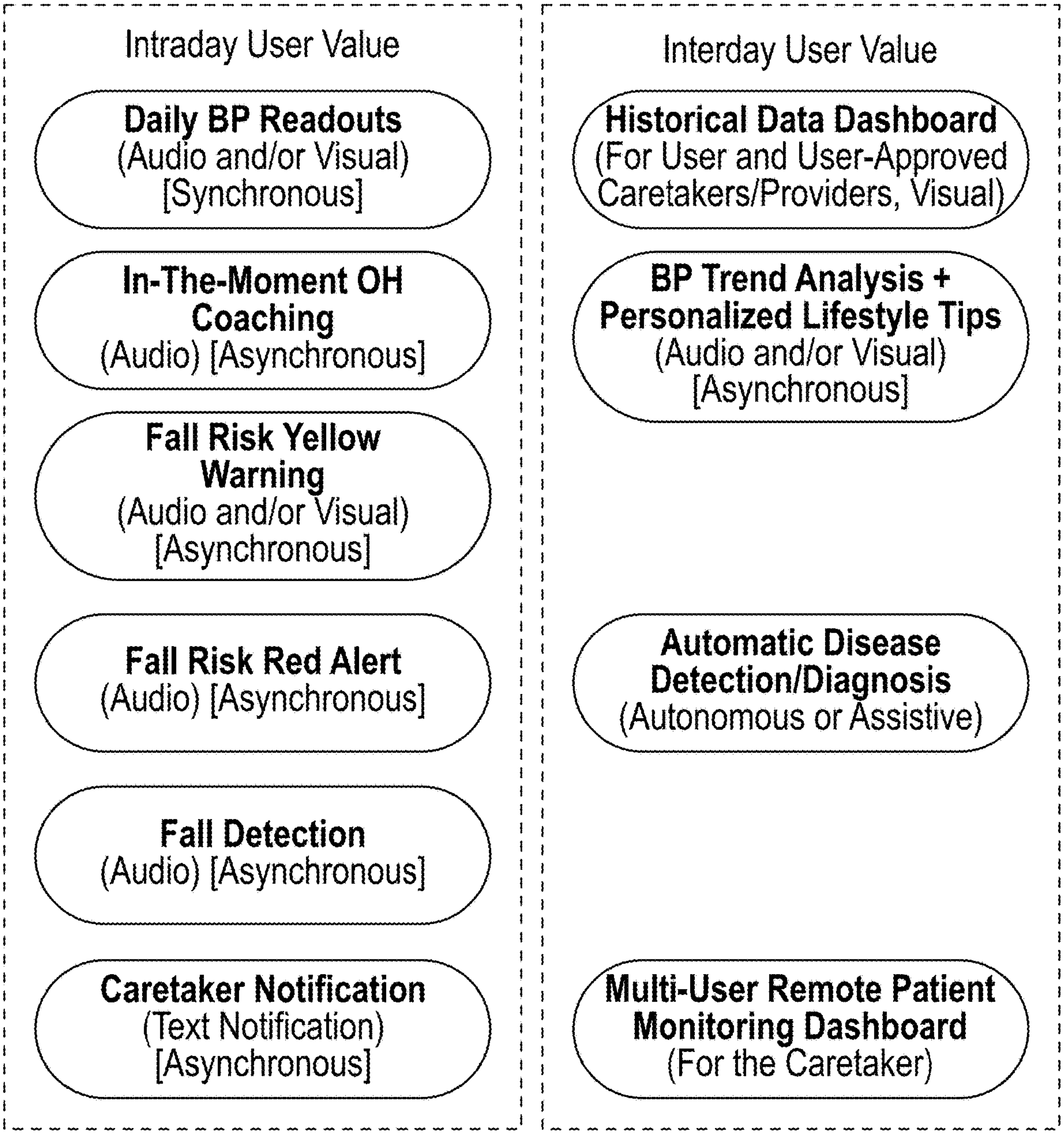
FIG. 16 shows a list of exemplary potential user features that provide value to a caregiver or user, per an embodiment herein.

FIG. 16 shows a list of exemplary user properties that provide value to a caregiver or the user. In some embodiments, the cloud computing back-end further comprises a module configured to provide a healthcare provider portal application allowing access to real-time and historical data and trends for one or more subjects. In some embodiments, the cloud computing back-end further comprises a module configured to provide a subject health portal application allowing access to real-time and historical data and trends for the subject. In some embodiments, the biometric feedback or behavioral coaching recommendations pertain to prevention of poor cerebral blood flow, poor blood pressure, presyncope, syncope that may result in a fall. In some embodiments, the biometric feedback or behavioral coaching recommendations are delivered to the subject via the acoustic transducer in the form of one or more audio messages. In some embodiments, the local base station further comprises an acoustic transducer for broadcasting audio messages. In some embodiments, the biometric feedback or behavioral coaching recommendations are delivered via an acoustic transducer in the local base station in the form of one or more audio messages. In some embodiments, the local base station further comprises a screen for displaying biometric information and notifications. In some embodiments, the biometric feedback or behavioral coaching recommendations are delivered via the screen of the local base station in the form of one or more visual messages. In some embodiments, the biometric feedback or behavioral coaching recommendations are delivered to the subject or a caretaker for the subject via text message to a mobile device. In some embodiments, the analysis comprises applying one or more artificial neural networks (ANNs). In some embodiments, the one or more ANNs are configured to detect or predict poor cerebral blood flow, poor blood pressure, presyncope, syncope, and a fall event.

1.D. Machine Learning

In some embodiments, machine learning algorithms are utilized to process the biometric data and the activity data. In some embodiments, the machine learning algorithm is used to analyze the data to detect or predict one or more of: poor cerebral blood flow, poor blood pressure, presyncope, syncope, and a fall event. In some embodiments, the machine learning algorithm is used to identify one or more of the detected or predicted events. In some embodiments, an ANN model outputs a cerebral blood flow metric, a sitting blood pressure, a standing blood pressure, a laying blood pressure, a hypertension classification, an orthostatic hypotension classification, a user dizziness score, a syncope risk score, or any combination thereof.

In some embodiments, the machine learning algorithms utilized herein employ one or more forms of labels including but not limited to human annotated labels and semi-supervised labels. The human annotated labels can be provided by a hand-crafted heuristic. For example, the hand-crafted heuristic can comprise comparing a current blood pressure to a predetermined blood pressure graph. The semi-supervised labels can be determined using a clustering technique to determine poor cerebral blood flow, poor blood pressure, presyncope, syncope, or a fall event similar to those flagged by previous human annotated labels and previous semi-supervised labels. The semi-supervised labels can employ a XGBoost, a neural network, or both.

In some embodiments, the methods and systems herein employ a distant supervision method. The distant supervision method can create a large training set seeded by a small hand-annotated training set. The distant supervision method can comprise positive-unlabeled learning with the training set as the 'positive' class. The distant supervision method can employ a logistic regression model, a recurrent neural network, or both.

Examples of machine learning algorithms can include a support vector machine (SVM), a naïve Bayes classification, a random forest, a neural network, deep learning, or other supervised learning algorithm or unsupervised learning algorithm for classification and regression. The machine learning algorithms can be trained using one or more training datasets.

In some embodiments, the machine learning algorithm utilizes regression modeling, wherein relationships between predictor variables and dependent variables are determined and weighted. In one embodiment, for example, a predicted event can be a dependent variable and is derived from the biometric and activity data.

In some embodiments, a machine learning algorithm is used to infer systolic and diastolic blood pressures from the available biometric and user profile data. A non-limiting example of a multi-variate linear regression model algorithm is seen below: probability=A0+A1 (X1)+A2 (X2)+A3 (X3)+A4 (X4)+A5 (X5)+A6 (X6)+A7 (X7) . . . , wherein Ai (A1, A2, A3, A4, A5, A6, A7, . . . ) are "weights" or coefficients found during the regression modeling; and Xi (X1, X2, X3, X4, X5, X6, X7, . . . ) are data collected from the Subject. Any number of Ai and Xi variable can be included in the model. For example, in a non-limiting example wherein there are 3 Xi terms, X1 is the biometric data, X2 is the activity data, and X3 is the probability that an event has been detected or predicted. In some embodiments, the programming language "Python" is used to run the model.

In some embodiments, training comprises multiple steps. In a first step, an initial model is constructed by assigning probability weights to predictor variables. In a second step, the initial model is used to infer blood pressure values. In a third step, the validation module compares against labeled blood pressure data and feeds back the verified data to improve prediction accuracy. At least one of the first step, the second step, and the third step can repeat one or more times continuously or at set intervals.

1.E. Computing System

Figure 11:
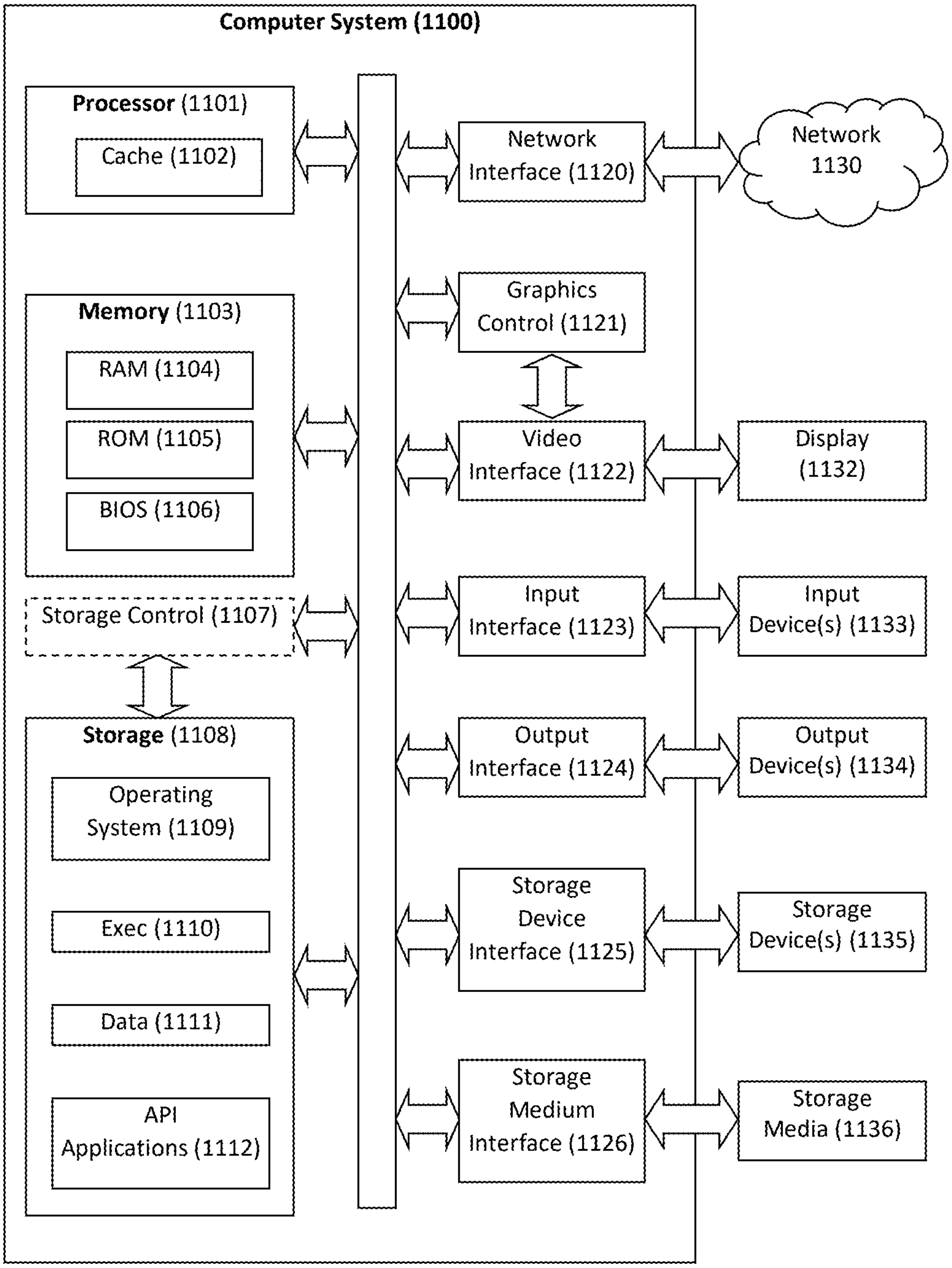
FIG. 11 shows a non-limiting example of a computing device; in this case, a device with one or more processors, memory, storage, and a network interface, per an embodiment herein.

Referring to FIG. 11, a block diagram is shown depicting an exemplary machine that includes a computer system 1100 (e.g., a processing or computing system) within which a set of instructions can execute for causing a device to perform or execute any one or more of the aspects and/or methodologies for static code scheduling of the present disclosure. The components in FIG. 11 are examples only and do not limit the scope of use or functionality of any hardware, software, embedded logic component, or a combination of two or more such components implementing particular embodiments.

Computer system 1100 may include one or more processors 1101, a memory 1103, and a storage 1108 that communicate with each other, and with other components, via a bus 1140. The bus 1140 may also link a display 1132, one or more input devices 1133 (which may, for example, include a keypad, a keyboard, a mouse, a stylus, etc.), one or more output devices 1134, one or more storage devices 1135, and various tangible storage media 1136. All of these elements may interface directly or via one or more interfaces or adaptors to the bus 1140. For instance, the various tangible storage media 1136 can interface with the bus 1140 via storage medium interface 1126. Computer system 1100 may have any suitable physical form, including but not limited to one or more integrated circuits (ICs), printed circuit boards (PCBs), mobile handheld devices (such as mobile telephones or PDAs), laptop or notebook computers, distributed computer systems, computing grids, or servers.

Computer system 1100 includes one or more processor(s) 1101 (e.g., central processing units (CPUs) or general purpose graphics processing units (GPGPUs)) that carry out functions. Processor(s) 1101 optionally contains a cache memory unit 1102 for temporary local storage of instructions, data, or computer addresses. Processor(s) 1101 are configured to assist in execution of computer readable instructions. Computer system 1100 may provide functionality for the components depicted in FIG. 11 as a result of the processor(s) 1101 executing non-transitory, processor-executable instructions embodied in one or more tangible computer-readable storage media, such as memory 1103, storage 1108, storage devices 1135, and/or storage medium 1136. The computer-readable media may store software that implements particular embodiments, and processor(s) 1101 may execute the software. Memory 1103 may read the software from one or more other computer-readable media (such as mass storage device(s) 1135, 1136) or from one or more other sources through a suitable interface, such as network interface 1120. The software may cause processor(s) 1101 to carry out one or more processes or one or more steps of one or more processes described or illustrated herein. Carrying out such processes or steps may include defining data structures stored in memory 1103 and modifying the data structures as directed by the software.

The memory 1103 may include various components (e.g., machine readable media) including, but not limited to, a random access memory component (e.g., RAM 1104) (e.g., static RAM (SRAM), dynamic RAM (DRAM), ferroelectric random access memory (FRAM), phase-change random access memory (PRAM), etc.), a read-only memory component (e.g., ROM 1105), and any combinations thereof. ROM 1105 may act to communicate data and instructions unidirectionally to processor(s) 1101, and RAM 1104 may act to communicate data and instructions bidirectionally with processor(s) 1101. ROM 1105 and RAM 1104 may include any suitable tangible computer-readable media described below. In one example, a basic input/output system 1106 (BIOS), including basic routines that help to transfer information between elements within computer system 1100, such as during start-up, may be stored in the memory 1103.

Fixed storage 1108 is connected bidirectionally to processor(s) 1101, optionally through storage control unit 1107. Fixed storage 1108 provides additional data storage capacity and may also include any suitable tangible computer-readable media described herein. Storage 1108 may be used to store operating system 1109, executable(s) 1110, data 1111, applications 1112 (application programs), and the like. Storage 1108 can also include an optical disk drive, a solid-state memory device (e.g., flash-based systems), or a combination of any of the above. Information in storage 1108 may, in appropriate cases, be incorporated as virtual memory in memory 1103.

In one example, storage device(s) 1135 may be removably interfaced with computer system 1100 (e.g., via an external port connector (not shown)) via a storage device interface 1125. Particularly, storage device(s) 1135 and an associated machine-readable medium may provide non-volatile and/or volatile storage of machine-readable instructions, data structures, program modules, and/or other data for the computer system 1100. In one example, software may reside, completely or partially, within a machine-readable medium on storage device(s) 1135. In another example, software may reside, completely or partially, within processor(s) 1101.

Bus 1140 connects a wide variety of subsystems. Herein, reference to a bus may encompass one or more digital signal lines serving a common function, where appropriate. Bus 1140 may be any of several types of bus structures including, but not limited to, a memory bus, a memory controller, a peripheral bus, a local bus, and any combinations thereof, using any of a variety of bus architectures. As an example and not by way of limitation, such architectures include an Industry Standard Architecture (ISA) bus, an Enhanced ISA (EISA) bus, a Micro Channel Architecture (MCA) bus, a Video Electronics Standards Association local bus (VLB), a Peripheral Component Interconnect (PCI) bus, a PCI-Express (PCI-X) bus, an Accelerated Graphics Port (AGP) bus, HyperTransport (HTX) bus, serial advanced technology attachment (SATA) bus, and any combinations thereof.

Computer system 1100 may also include an input device 1133. In one example, a user of computer system 1100 may enter commands and/or other information into computer system 1100 via input device(s) 1133. Examples of an input device(s) 1133 include, but are not limited to, an alpha-numeric input device (e.g., a keyboard), a pointing device (e.g., a mouse or touchpad), a touchpad, a touch screen, a multi-touch screen, a joystick, a stylus, a gamepad, an audio input device (e.g., a microphone, a voice response system, etc.), an optical scanner, a video or still image capture device (e.g., a camera), and any combinations thereof. In some embodiments, the input device is a Kinect, Leap Motion, or the like. Input device(s) 1133 may be interfaced to bus 1140 via any of a variety of input interfaces 1123 (e.g., input interface 1123) including, but not limited to, serial, parallel, game port, USB, FIREWIRE, THUNDERBOLT, or any combination of the above.

In particular embodiments, when computer system 1100 is connected to network 1130, computer system 1100 may communicate with other devices, specifically mobile devices and enterprise systems, distributed computing systems, cloud storage systems, cloud computing systems, and the like, connected to network 1130. Communications to and from computer system 1100 may be sent through network interface 1120. For example, network interface 1120 may receive incoming communications (such as requests or responses from other devices) in the form of one or more packets (such as Internet Protocol (IP) packets) from network 1130, and computer system 1100 may store the incoming communications in memory 1103 for processing. Computer system 1100 may similarly store outgoing communications (such as requests or responses to other devices) in the form of one or more packets in memory 1103 and communicated to network 1130 from network interface 1120. Processor(s) 1101 may access these communication packets stored in memory 1103 for processing.

Examples of the network interface 1120 include, but are not limited to, a network interface card, a modem, and any combination thereof. Examples of a network 1130 or network segment 1130 include, but are not limited to, a distributed computing system, a cloud computing system, a wide area network (WAN) (e.g., the Internet, an enterprise network), a local area network (LAN) (e.g., a network associated with an office, a building, a campus or other relatively small geographic space), a telephone network, a direct connection between two computing devices, a peer-to-peer network, and any combinations thereof. A network, such as network 1130, may employ a wired and/or a wireless mode of communication. In general, any network topology may be used.

In addition to a display 1132, computer system 1100 may include one or more other peripheral output devices 1134 including, but not limited to, an audio speaker, a printer, a storage device, and any combinations thereof. Such peripheral output devices may be connected to the bus 1140 via an output interface 1124. Examples of an output interface 1124 include, but are not limited to, a serial port, a parallel connection, a USB port, a FIREWIRE port, a THUNDERBOLT port, and any combinations thereof.

In addition or as an alternative, computer system 1100 may provide functionality as a result of logic hardwired or otherwise embodied in a circuit, which may operate in place of or together with software to execute one or more processes or one or more steps of one or more processes described or illustrated herein. Reference to software in this disclosure may encompass logic, and reference to logic may encompass software. Moreover, reference to a computer-readable medium may encompass a circuit (such as an IC) storing software for execution, a circuit embodying logic for execution, or both, where appropriate. The present disclosure encompasses any suitable combination of hardware, software, or both.

Those of skill in the art will appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof configured to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by one or more processor(s), or in a combination of the two. A software module may reside in RAM memory, flash memory, ROM memory, EPROM memory, EEPROM memory, registers, hard disk, a removable disk, a CD-ROM, or any other form of storage medium known in the art. A storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In accordance with the description herein, suitable computing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will also recognize that select televisions, video players, and digital music players with optional computer network connectivity are suitable for use in the system described herein. Suitable tablet computers, in various embodiments, include those with booklet, slate, and convertible configurations, known to those of skill in the art.

In some embodiments, the computing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smartphone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TVQ, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3®, Sony® PS4®, Microsoft® Xbox 360®, Microsoft Xbox One, Nintendo® Wii®, Nintendo Wii U®, and Ouya®.

1.F. Non-Transitory Computer Readable Storage Medium

In some embodiments, the platforms, systems, media, and methods disclosed herein include one or more non-transitory computer readable storage media encoded with a program including instructions executable by the operating system of an optionally networked computing device. In further embodiments, a computer readable storage medium is a tangible component of a computing device. In still further embodiments, a computer readable storage medium is optionally removable from a computing device. In some embodiments, a computer readable storage medium includes, by way of non-limiting examples, CD-ROMs, DVDs, flash memory devices, solid state memory, magnetic disk drives, magnetic tape drives, optical disk drives, distributed computing systems including cloud computing systems and services, and the like. In some cases, the program and instructions are permanently, substantially permanently, semi-permanently, or non-transitorily encoded on the media.

1.G. Computer Program

In some embodiments, the platforms, systems, media, and methods disclosed herein include at least one computer program, or use of the same. A computer program includes a sequence of instructions, executable by one or more processor(s) of the computing device's CPU, written to perform a specified task. Computer readable instructions may be implemented as program modules, such as functions, objects, Application Programming Interfaces (APIs), computing data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

1.H. Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft®.NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or extensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Figure 12:
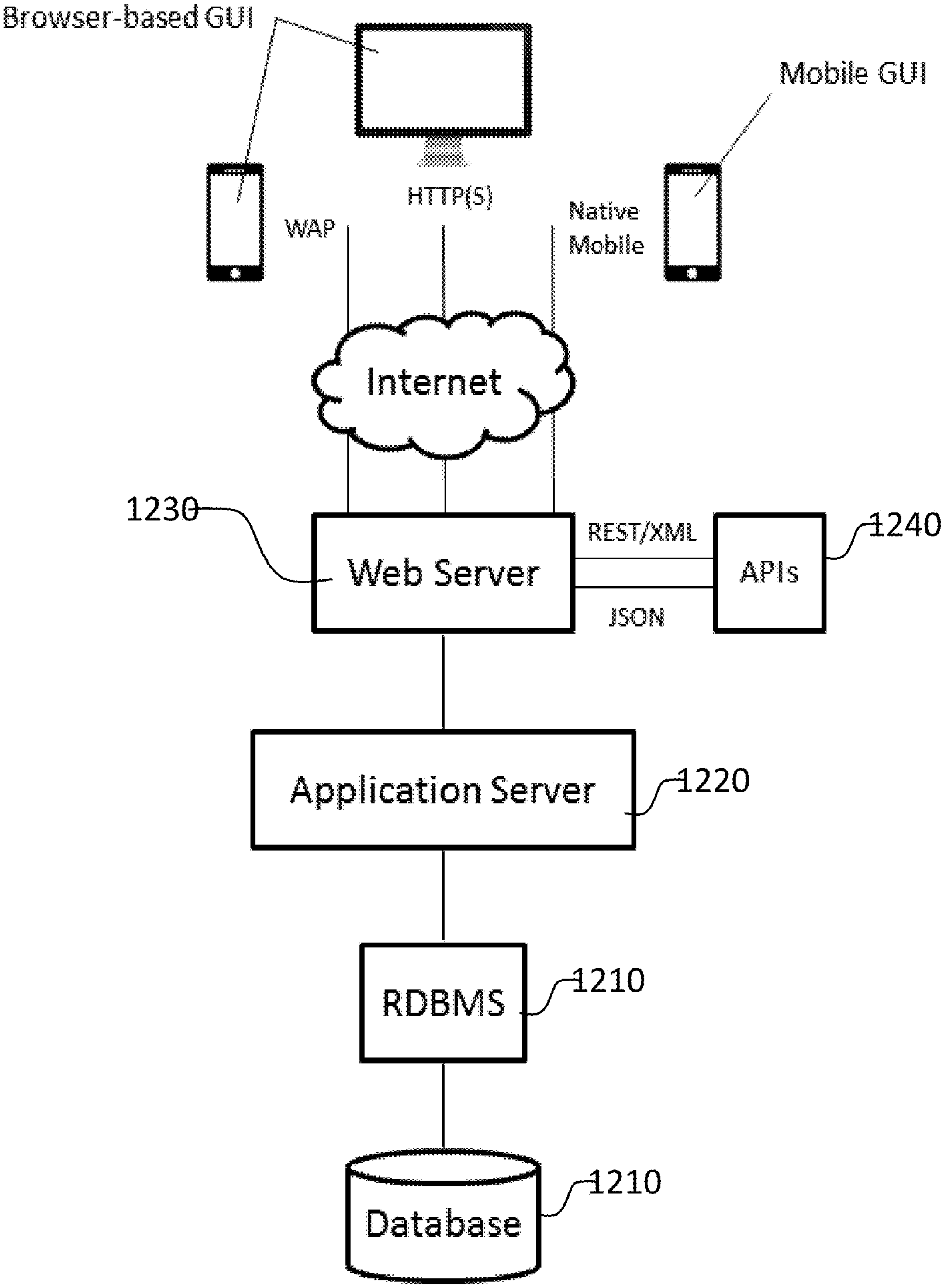
FIG. 12 shows a non-limiting example of a web/mobile application provision system; in this case, a system providing browser-based and/or native mobile user interfaces, per an embodiment herein.

Referring to FIG. 12, in a particular embodiment, an application provision system comprises one or more databases 1200 accessed by a relational database management system (RDBMS) 1110. Suitable RDBMSs include Firebird, MySQL, PostgreSQL, SQLite, Oracle Database, Microsoft SQL Server, IBM DB2, IBM Informix, SAP Sybase, SAP Sybase, Teradata, and the like. In this embodiment, the application provision system further comprises one or more application severs 1220 (such as Java servers, .NET servers, PHP servers, and the like) and one or more web servers 1230 (such as Apache, IIS, GWS and the like). The web server(s) optionally expose one or more web services via app application programming interfaces (APIs) 1240. Via a network, such as the Internet, the system provides browser-based and/or mobile native user interfaces.

Figure 13:
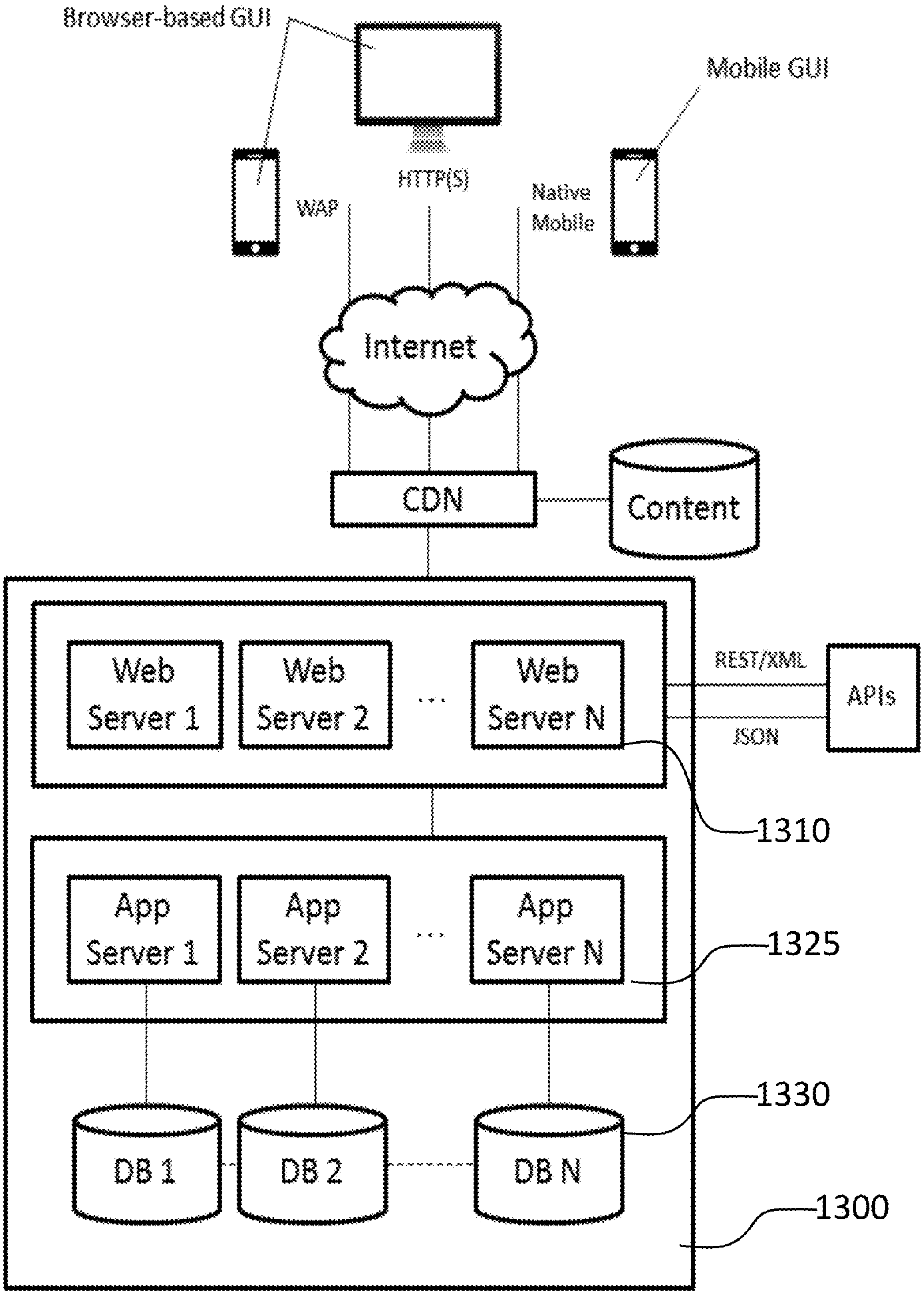
FIG. 13 shows a non-limiting example of a cloud-based web/mobile application provision system; in this case, a system comprising an elastically load balanced, auto-scaling web server and application server resources as well synchronously replicated databases, per an embodiment herein.

Referring to FIG. 13, in a particular embodiment, an application provision system alternatively has a distributed, cloud-based architecture 1300 and comprises elastically load balanced, auto-scaling web server resources 1310 and application server resources 1320 as well synchronously replicated databases 1330.

1.I. Mobile Application

In some embodiments, a computer program includes a mobile application provided to a mobile computing device. In some embodiments, the mobile application is provided to a mobile computing device at the time it is manufactured. In other embodiments, the mobile application is provided to a mobile computing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite,.NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome WebStore, BlackBerry® App World, App Store for Palm devices, App Catalog for webOS, Windows® Marketplace for Mobile, Ovi Store for Nokia® devices, Samsung® Apps, and Nintendo® DSi Shop.

1.J. Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on a distributed computing platform such as a cloud computing platform. In some embodiments, software modules are hosted on one or more machines in one location. In other embodiments, software modules are hosted on one or more machines in more than one location.

1.K. Databases

In some embodiments, the methods, devices, systems, and platforms disclosed herein include one or more databases, or use of the same. In view of the disclosure provided herein, those of skill in the art will recognize that many databases are suitable for storage and retrieval of medical information. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In a particular embodiment, a database is a distributed database. In other embodiments, a database is based on one or more local computer storage devices.

2. NON-INVASIVELY INFERRING CEREBRAL BLOOD FLOW FROM THE EXTERNAL CAROTID ARTERY

FIGS. 17-23 depict features of non-invasively inferring cerebral blood flow from the external carotid artery. FIGS. 17-23 may apply or use any of the features of FIGS. 1-16 and FIGS. 24-33.

Cerebral Blood Flow (CBF) refers to the blood supply to the brain. This blood flow is a major factor in brain function, as it delivers the oxygen and nutrients that the brain requires to operate effectively. Inadequate CBF, often referred to as poor CBF, can lead to a variety of health issues, including chronic fatigue, dizziness, brain fog, nausea, and fainting.

Poor CBF is often associated with a range of diseases, conditions, and syndromes, including Orthostatic Hypotension (OH), Postural Orthostatic Tachycardia Syndrome (POTS), Orthostatic Cerebral Hypoperfusion Syndrome (OCHOs), Primary Cerebral Autoregulatory Failure (pCAF), Vasovagal Syncope, Carotid Sinus Sensitivity, hypovolemia, drug-induced hypotension, arrhythmias, vascular stenosis, aortic stenosis, Ehlers-Danlos Syndrome, Multiple Sclerosis, Multiple System Atrophy, Parkinson's, dementia, and various other neurological disorders that compromise the autonomic system (Dysautonomias).

The measurement of CBF is challenging, as traditional techniques attempt to directly measure blood flow through the skull, which requires highly trained technicians and suffers from a lack of repeatability. Because existing direct measurements of CBF are challenging, two secondary metrics are used to infer CBF: blood pressure and heart rate. However, these metrics often do not correlate with symptoms, leading to difficulties in diagnosing and managing conditions associated with poor CBF.

Biometric sensors are devices that measure and analyze human body characteristics. These sensors can be used to measure a variety of physiological parameters, including blood flow. Different types of biometric sensors include optical sensors, ultrasound transducers, photoacoustic transducers, and RF transducers. These sensors can be used to record a blood flow waveform, which is a graphical representation of the blood flow over time.

The External Carotid Artery (ECA) and the Internal Carotid Artery (ICA) are two major arteries that supply blood to the head. The ECA primarily supplies blood to the face and scalp, while the ICA provides the majority of blood flow to the brain. The Superficial Temporal Artery and the Posterior Auricular Artery are branches of the ECA.

Machine learning is a type of artificial intelligence that enables computers to learn from and make decisions based on data. In the context of CBF measurement, machine learning models can be trained to extract features from the blood flow waveform and infer CBF based on these features. These models can be trained against various types of measurements, including Transcranial Doppler (TCD) Ultrasound measurements of the Middle Cerebral Artery, ultrasound measurements of the Carotid and/or Vertebral arteries, and Diffuse Correlation Spectroscopy measurements of frontal lobe perfusion.

The present disclosure provides a method and system for non-invasively measuring cerebral blood flow. This is achieved through the use of an in-ear device equipped with a biometric sensor and an algorithm. The biometric sensor is configured to record a blood flow waveform of branches of the Superficial Temporal Artery and/or Posterior Auricular Artery, which are branches of the External Carotid Artery. The sensor is further designed to be pressed against the auricle of the subject, ensuring accurate readings. The algorithm, on the other hand, is designed to extract features from the External Carotid Artery blood flow waveform morphology. These features are then used to infer total Cerebral Blood Flow, Blood Flow to the Head, Carotid Blood Flow, Stroke Volume (SV), and/or Cardiac Output (CO). This method and system offer a convenient and non-invasive approach to measure changes in cerebral blood flow, which is of paramount relevance in diagnosing and managing various health conditions.

The system includes a biometric sensor 101 that is configured to be removably retained against an external surface of a skin portion of a target location of a user. In some aspects, the biometric sensor 101 may be an optical sensor, an ultrasound transducer, a photoacoustic transducer, or an RF transducer. The biometric sensor 101 is designed to record a blood flow waveform of branches of the Superficial Temporal Artery and/or Posterior Auricular Artery, which are branches of the External Carotid Artery.

In some cases, the biometric sensor 101 is configured to be anchored to a left auricle of the user. This positioning may be advantageous due to the direct branching of the left common carotid artery from the aorta, which may provide a more accurate inference of changes in total Cerebral Blood Flow. In other cases, the biometric sensor 101 may be anchored to an auricle of the user at a cymba concha of the user. This location may provide easy access to a clean arterial pulse waveform due to the presence of a shallow ear artery that is a branch of the Posterior Auricular Artery and pierces through the auricular cartilage to the anterior side of the ear.

The system also includes a processor and a memory storing computer instructions. The processor and memory are configured to obtain, using the biometric sensor 101, biometric data relating to a blood flow waveform of one or more arteries near the target location. The system is further configured to determine, based on the biometric data relating to the blood flow waveform of the one or more arteries near the target location, a parameter indicative of a blood flow to a brain of the user. The parameter indicative of the blood flow to the brain of the user may be determined by performing one or more computations using the biometric data and/or the blood flow waveform of the one or more arteries near the target location. The system is also configured to display or transmit the parameter indicative of the blood flow to the brain of the user. This allows for real-time monitoring and analysis of cerebral blood flow, which can be beneficial in diagnosing and managing various health conditions.

In some aspects, the biometric sensor 101 may be an optical sensor. The optical sensor may use photoplethysmography, laser doppler flowmetry, or laser speckle contrast imaging to monitor the blood flow waveform. Photoplethysmography, for instance, may involve the use of a light source and a photodetector to measure changes in light intensity caused by changes in blood volume in the microvascular bed of tissue. Laser doppler flowmetry, on the other hand, may involve the use of laser light to measure the speed of blood flow in the arteries. Laser speckle contrast imaging may look at the dynamic backscattering of light caused by changes in blood flow. These techniques may provide a non-invasive way to monitor blood flow in the arteries near the target location.

In other cases, the biometric sensor 101 may be an ultrasound transducer or a photoacoustic transducer. These types of sensors may use sound waves to create images of the blood flow in the arteries. The ultrasound transducer may emit high-frequency sound waves that bounce off the blood cells moving through the arteries. The doppler echoes of these sound waves may then be used to calculate blood flow velocities and capture a representative waveform. The photoacoustic transducer, on the other hand, may use a combination of light and sound to capture a blood flow waveform. This may involve the use of a laser to heat up the blood cells, causing them to expand and create an acoustic signal that can be detected by the transducer.

In yet other cases, the biometric sensor 101 may be an RF transducer. The RF transducer may use radio frequency signals to measure the blood flow in the arteries. This may involve the use of an RF signal generator to produce a signal that is reflected off the blood cells moving through the arteries. The reflected signal may then be detected by the RF transducer and used to determine the speed and direction of the blood flow.

In some embodiments, the biometric sensor 101 is attached to a polymeric insert comprising an aperture through which the biometric sensor emits light or sound waves. The polymeric insert may be designed to fit comfortably in the ear of the user, ensuring that the biometric sensor 101 is positioned correctly to monitor the blood flow in the arteries near the target location. The aperture in the polymeric insert may allow the light or sound waves emitted by the biometric sensor 101 to reach the arteries without obstruction, ensuring accurate readings of the blood flow waveform.

In some aspects, the parameter indicative of the blood flow to the brain of the user is determined by an integrated hardware device that includes the biometric sensor 101 and is configured to be disposed at the target location of the user. The integrated hardware device, also referred to as device 100, may include additional components such as a movement sensor 102, a logic element 103, an acoustic transducer 104, a wireless communications transceiver 105, and a microcontroller 106. These components may work in conjunction to obtain, process, and display or transmit biometric data related to blood flow to the brain.

In some cases, the biometric sensor 101 may obtain biometric data relating to a blood flow waveform of one or more arteries near a target location of a user. This may involve the biometric sensor 101 emitting light or sound waves, which interact with the blood cells moving through the arteries. The reflected or scattered light or sound waves may then be detected by the biometric sensor 101, providing information about the blood flow waveform.

In some aspects, the device 100 may determine a parameter indicative of a blood flow to a brain of the user based on the biometric data relating to the blood flow waveform of the one or more arteries near the target location. This may involve the logic element 103 or the microcontroller 106 performing one or more computations using the biometric data and/or the blood flow waveform. The computations may involve analyzing the fullness of the blood flow waveform, determining the area under the systolic period of the cardiac cycle, or extracting features related to Stroke Volume (SV). The computations may also involve the use of a machine learning model that has been trained to identify relationships between the biometric data and cerebral blood flow.

In some cases, the device 100 may display or transmit the parameter indicative of the blood flow to the brain of the user. This may involve the use of an integrated display, an audio speaker, or a wireless communications transceiver 105 to transmit the parameter to an external device such as a smartphone, tablet, or computer. The display or transmission of the parameter may allow for real-time monitoring of cerebral blood flow, which can be beneficial in diagnosing and managing various health conditions.

In some aspects, the device 100 may perform one or more computations using the biometric data and/or the blood flow waveform of the one or more arteries near the target location to determine the parameter indicative of the blood flow to the brain of the user. These computations may be performed by the logic element 103 or the microcontroller 106, which may be configured to process the biometric data obtained by the biometric sensor 101. The computations may involve various techniques and methods to analyze the blood flow waveform and extract relevant features.

In some cases, the computations may involve analyzing the fullness of the blood flow waveform of the one or more arteries near the target location. The fullness of the blood flow waveform may refer to the relative area under the curve of the waveform, which may provide information about the volume of blood flowing through the arteries. The fullness of the blood flow waveform may be affected by various factors such as the heart rate, blood pressure, and the diameter of the arteries, among others. By analyzing the fullness of the blood flow waveform, the device 100 may be able to infer changes in the blood flow to the brain of the user.

In other cases, the computations may involve determining an area under the systolic period of a cardiac pulse in the blood flow waveform of the one or more arteries near the target location. The systolic period of a cardiac pulse refers to the phase of the cardiac cycle during which the heart contracts and pumps blood into the arteries. The area under the systolic period of the cardiac pulse in the blood flow waveform may provide information about the volume of blood pumped by the heart during each cardiac cycle, which may be used to infer the Stroke Volume (SV) and/or the Cardiac Output (CO).

In yet other cases, the computations may involve determining an assessment of a time period from a start of systole to a dichrotic notch of the cardiac pulse in a carotid artery of the user. The dichrotic notch refers to a small dip in the blood flow waveform that occurs after the peak of the systolic period, which corresponds to the closure of the aortic valve. The time period from the start of systole to the dichrotic notch, also known as the Carotid Flow Time, may provide information about the length of time that the heart is actively pumping blood into the carotid artery, which may be used to infer changes in the blood flow to the brain of the user.

In some aspects, the device 100 may display or transmit the parameter indicative of the blood flow to the brain of the user. This may involve the use of an integrated display or a wireless communications transceiver 105 to transmit the parameter to an external device such as a smartphone, tablet, or computer. The display or transmission of the parameter may allow for real-time monitoring of cerebral blood flow, which can be beneficial in diagnosing and managing various health conditions.

2.A. Shallow Artery for Biometric Sensing

Figure 17:
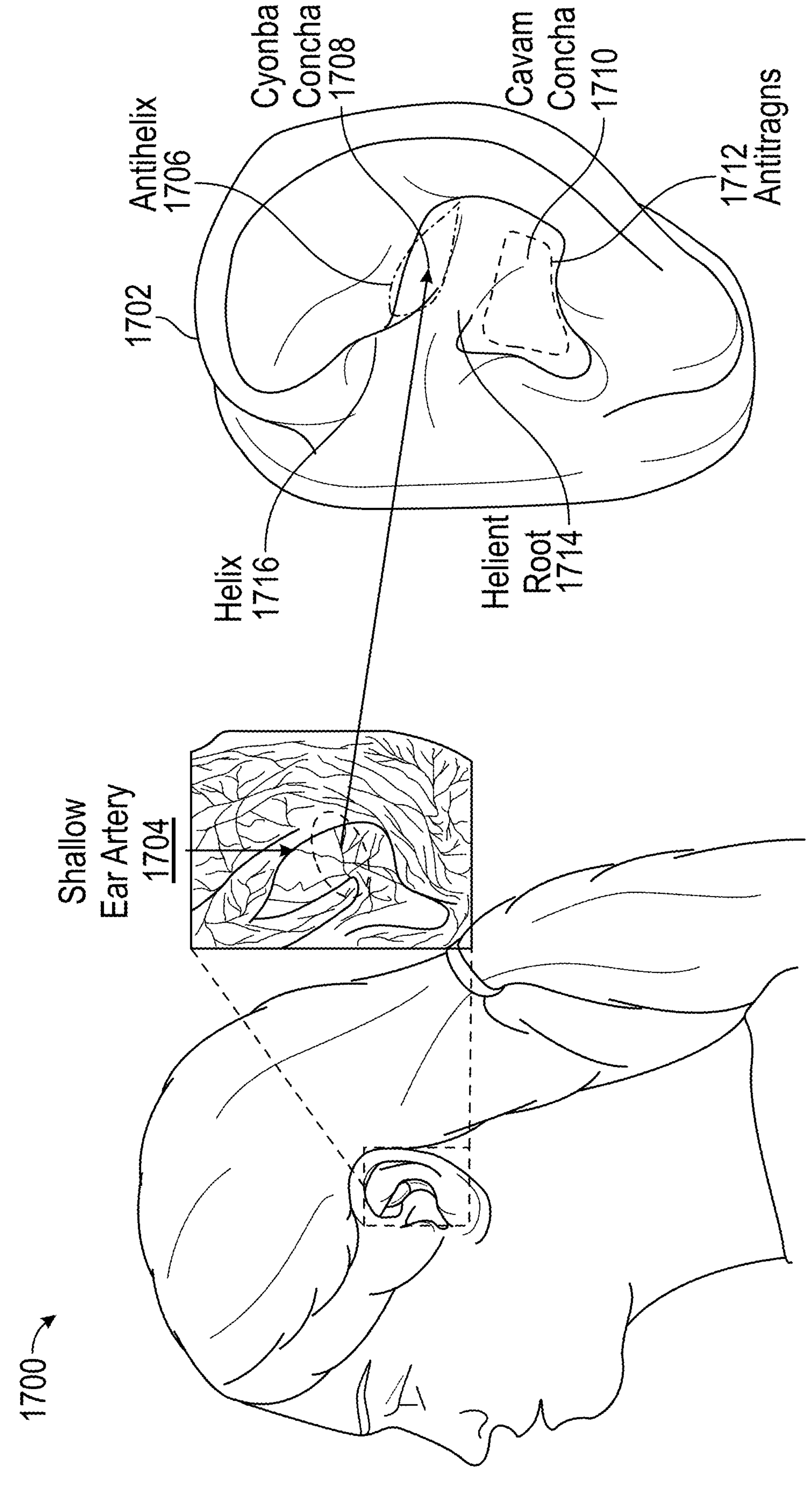
FIG. 17 depicts a detailed view of an ear highlighting various anatomical features and the location of a shallow ear artery, according to aspects of the present disclosure.

FIG. 17 depicts a view 1700 of an ear 1702 illustrating various anatomical features and the location of a shallow ear artery 1704. The ear 1702 includes an antihelix 1706, a cymba concha 1708, a cavum concha 1710, an antitragus 1712, a helical root 1714, and a helix 1716. In some aspects, the biometric sensor 101 may be configured to be anchored to a left auricle of the user. In other cases, the biometric sensor 101 may be anchored to an auricle of the user at a cymba concha 1708.

In some embodiments, the target location for the biometric sensor 101 may be within the ear 1702 of the user. The biometric sensor 101 may be attached to a polymeric insert comprising an aperture through which the biometric sensor emits light. When the polymeric insert is positioned within the ear 1702 of the user, the aperture may be less than five (5) millimeters from a branch of the posterior auricular artery that perforates an auricular cartilage to protrude at an anterior face of the ear 1702 of the user.

In some cases, the posterior auricular artery protrudes from a base of a helical root 1714 of the ear 1702 of the user, and the polymeric insert is positioned at the base of the helical root 1714. This positioning allows the biometric sensor 101 to capture a strong carotid artery pulse waveform, which can be used to infer changes in cerebral blood flow.

In other embodiments, the target location for the biometric sensor 101 may be a temple of the user to target a superficial temporal artery of the user, or an underside of a wrist of the user to target a radial artery of the user. Regardless of the target location, the biometric sensor 101 is configured to obtain biometric data relating to a blood flow waveform of one or more arteries near the target location. This data can then be used to determine a parameter indicative of a blood flow to a brain of the user.

2.B. Pipeline

Figure 18:
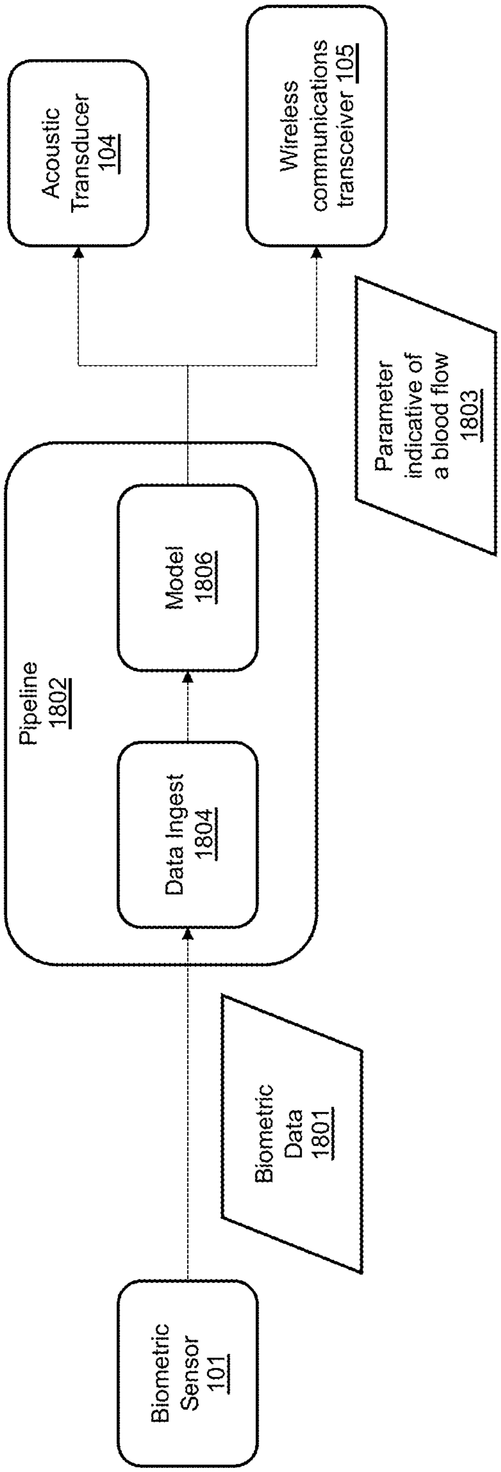
FIG. 18 presents a block diagram of a system for non-invasively measuring blood flow to a brain, according to aspects of the present disclosure.

FIG. 18 presents a block diagram 1800 illustrating the data processing pipeline of the system. The biometric sensor 101 collects biometric data 1801, which is then processed through a pipeline 1802. The pipeline 1802 includes a data ingest module 1804 and a model 1806. The processed data results in a parameter indicative of a blood flow 1803.

In some aspects, the biometric sensor 101 may be configured to obtain biometric data 1801 relating to a blood flow waveform of one or more arteries near a target location. This biometric data 1801 may be processed through the pipeline 1802, which includes a data ingest module 1804 and a model 1806. The data ingest module 1804 may be configured to receive and preprocess the biometric data 1801. The preprocessing may include, for example, filtering, normalization, or other data cleaning operations.

The model 1806 may be a machine learning model or other computational model configured to process the preprocessed biometric data 1801 and determine a parameter indicative of a blood flow 1803. The parameter indicative of a blood flow 1803 may be a measure of cerebral blood flow, blood flow to the head, carotid blood flow, stroke volume (SV), and/or cardiac output (CO). The determination of the parameter indicative of a blood flow 1803 may involve performing one or more computations using the biometric data 1801 and/or the blood flow waveform of the one or more arteries near the target location.

The system may also include an acoustic transducer 104 and a wireless communications transceiver 105, which facilitate additional data collection and communication functionalities. In some cases, the acoustic transducer 104 may be used to generate sound waves that interact with the blood flow in the one or more arteries near the target location. The reflected sound waves may be detected by the biometric sensor 101 and used to enhance the accuracy of the blood flow waveform measurement.

The wireless communications transceiver 105 may be used to transmit the parameter indicative of a blood flow 1803 to a remote device, such as a computer, smartphone, or medical device. In some aspects, the wireless communications transceiver 105 may also receive data from the remote device, such as updates to the model 1806 or instructions for controlling the operation of the biometric sensor 101.

In some embodiments, the one or more computations performed by the system are executed by a machine learning model 1806. This model 1806 may be trained based on a plurality of sample data pairs to identify one or more relationships between the sample biometric data and the sample brain biometric data. The sample data pairs may be obtained by pairing the sample biometric data to the sample brain biometric data obtained for a respective sample subject. Based on these sample data pairs, the model 1806 may determine one or more relationships between the sample biometric data and the sample brain biometric data.

In some cases, the model 1806 may be a machine learning model trained to process the preprocessed biometric data 1801 and determine a parameter indicative of a blood flow 1803. The parameter indicative of a blood flow 1803 may be a measure of cerebral blood flow, blood flow to the head, carotid blood flow, stroke volume (SV), and/or cardiac output (CO). The determination of the parameter indicative of a blood flow 1803 may involve performing one or more computations using the biometric data 1801 and/or the blood flow waveform of the one or more arteries near the target location.

In some aspects, the system may display or transmit the determined parameter indicative of a blood flow 1803. This may involve displaying the parameter on a display of the device 100 or transmitting the parameter to a remote device via the wireless communications transceiver 105. The remote device may be a computer, a smartphone, a medical device, or any other device capable of receiving and processing the transmitted parameter.

In some cases, the system may perform one or more computations using the biometric data 1801 and/or the blood flow waveform of the one or more arteries near the target location. These computations may involve analyzing the fullness of the blood flow waveform, determining an area under a systolic period of a cardiac pulse in the blood flow waveform, determining an assessment of a time period from a start of systole to a dichrotic notch of a cardiac pulse in a carotid artery of the user, or any combination thereof. The results of these computations may be used to determine the parameter indicative of a blood flow 1803.

In some embodiments, the system may use the parameter indicative of a blood flow 1803 to infer changes in cerebral blood flow, blood flow to the head, carotid blood flow, stroke volume (SV), and/or cardiac output (CO). This may provide a convenient and non-invasive way to measure changes in these parameters, which could be instrumental in the diagnosis and management of various neurological disorders and conditions that compromise the autonomic system.

2.C. Relationship Between Shallow Artery and Blood Flow to Head

FIGS. 19-22 depict charts and illustrations explaining the relationship between shallow arteries and blood flow to a head of a user.

Figure 19:
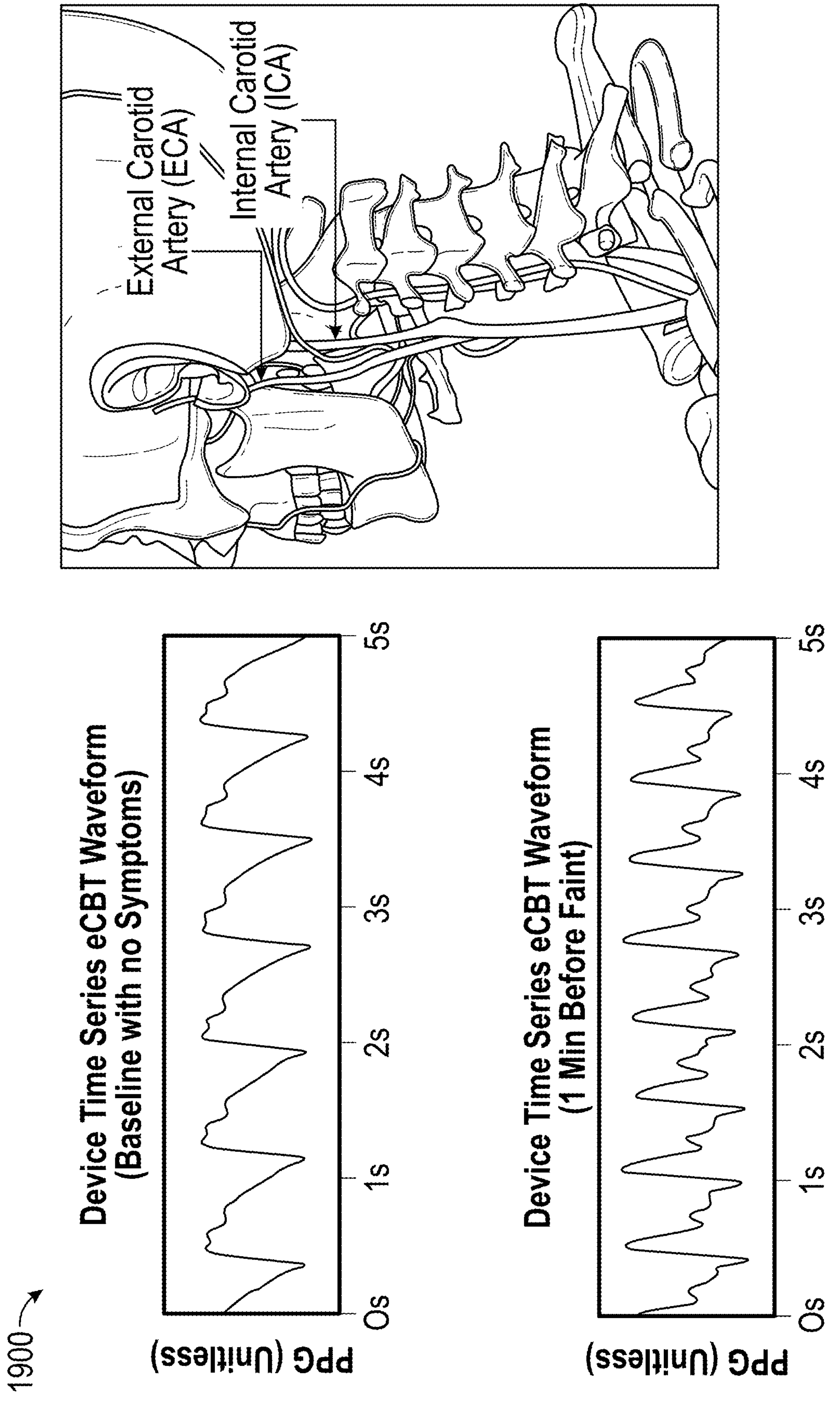
FIG. 19 shows a comparison of device time series eCBF waveforms and an anatomical illustration of the carotid arteries, according to aspects of the present disclosure.

FIG. 19 depicts a comparison 1900 of device time series External Carotid Blood Flow (eCBF) waveforms in the context of the anatomical illustration of the carotid arteries. The top graph shows the device time series eCBF waveform (baseline with no symptoms) with time markers from the 0-second mark 0 s to the 5-second mark 5 s. The bottom graph shows the device time series eCBF waveform (1 min before faint) with the same time markers from the 0-second mark 0 s to the 5-second mark 5 s. The anatomical illustration on the right highlights the External Carotid Artery (ECA) and the Internal Carotid Artery (ICA) in relation to the head and neck.

In some aspects, the graphs illustrate changes in the eCBF waveform over time. These changes may be indicative of changes in cerebral blood flow. For instance, a visible reduction in relative fullness (i.e., area under the curve) of the eCBF waveform may indicate a reduction in cerebral blood flow.

In some cases, the system may perform one or more computations to analyze these changes in the eCBF waveform. These computations may include analyzing a fullness of the blood flow waveform of the one or more arteries near the target location, determining an area under a systolic period of a cardiac pulse in the blood flow waveform of the one or more arteries near the target location, and determining an assessment of a time period from a start of systole to a dichrotic notch of the cardiac pulse in a carotid artery of the user.

In some embodiments, the system may use the results of these computations to determine a parameter indicative of a blood flow 1803. This parameter may be a measure of cerebral blood flow, blood flow to the head, carotid blood flow, stroke volume (SV), and/or cardiac output (CO). The determination of the parameter indicative of a blood flow 1803 may involve performing one or more computations using the biometric data 1801 and/or the blood flow waveform of the one or more arteries near the target location.

In some aspects, the system may display or transmit the determined parameter indicative of a blood flow 1803. This may involve displaying the parameter on a display of the device 100 or transmitting the parameter to a remote device via the wireless communications transceiver 105. The remote device may be a computer, a smartphone, a medical device, or any other device capable of receiving and processing the transmitted parameter.

In some cases, the system may perform one or more computations using the biometric data 1801 and/or the blood flow waveform of the one or more arteries near the target location. These computations may involve analyzing the fullness of the blood flow waveform, determining an area under a systolic period of a cardiac pulse in the blood flow waveform, determining an assessment of a time period from a start of systole to a dichrotic notch of a cardiac pulse in a carotid artery of the user, or any combination thereof. The results of these computations may be used to determine the parameter indicative of a blood flow 1803.

In some embodiments, the system may use the parameter indicative of a blood flow 1803 to infer changes in cerebral blood flow, blood flow to the head, carotid blood flow, stroke volume (SV), and/or cardiac output (CO). This may provide a convenient and non-invasive way to measure changes in these parameters, which could be instrumental in the diagnosis and management of various neurological disorders and conditions that compromise the autonomic system.

Figure 20:
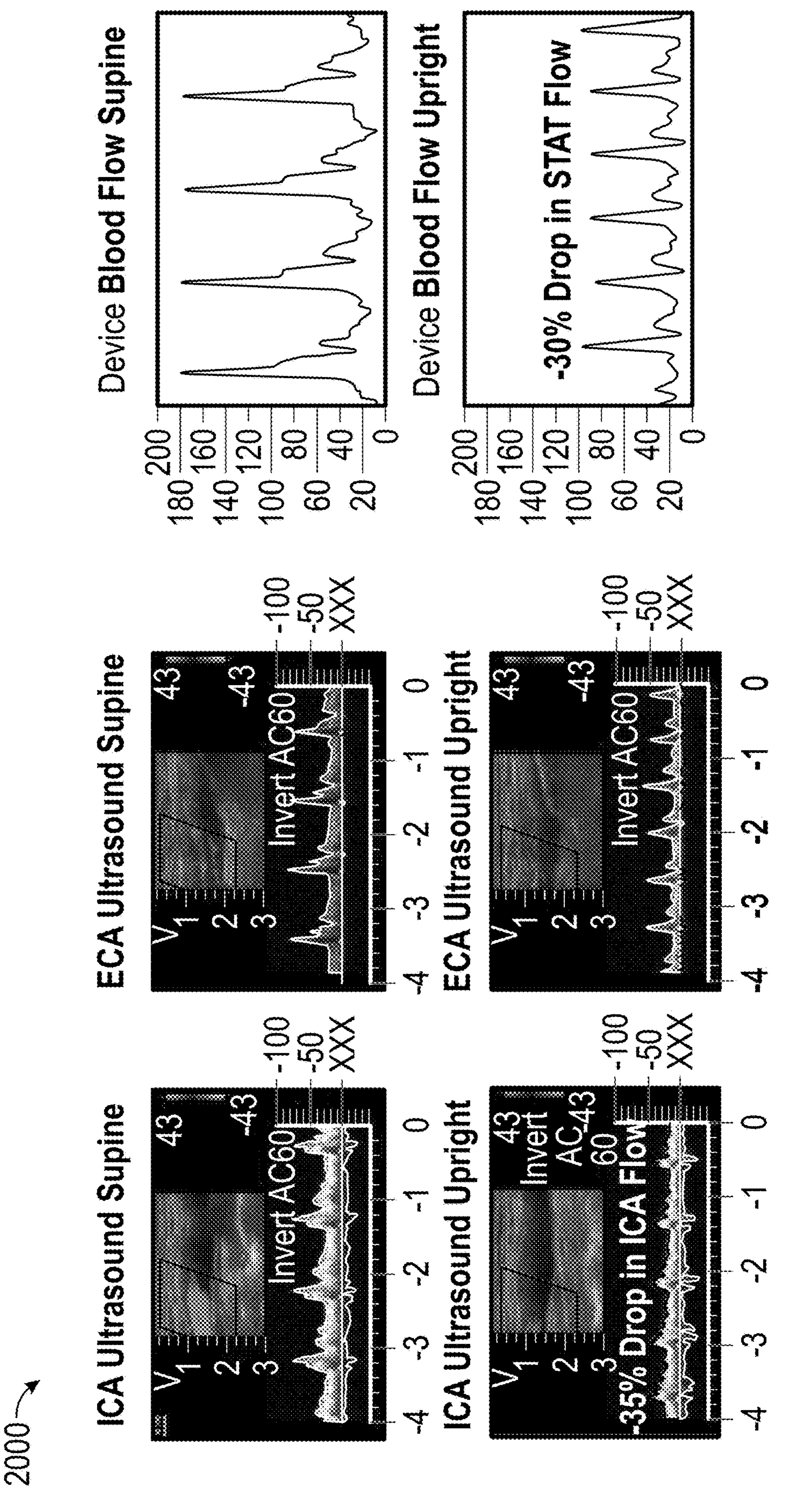
FIG. 20 depicts a comparison of blood flow measurements, according to aspects of the present disclosure.

FIG. 20 depicts a comparison of blood flow measurements 2000. On the left side of the figure, there are four ultrasound images showing blood flow in the Internal Carotid Artery (ICA) and External Carotid Artery (ECA) in both supine and upright positions. The top-left image shows ICA ultrasound in a supine position, while the top-right image shows ECA ultrasound in a supine position. The bottom-left image shows ICA ultrasound in an upright position with a noted 35% drop in ICA flow, and the bottom-right image shows ECA ultrasound in an upright position.

In some aspects, these ultrasound images may provide a visual representation of the changes in blood flow in the ICA and ECA when the user transitions from a supine to an upright position. These changes in blood flow may be indicative of changes in cerebral blood flow, which may be associated with various neurological disorders and conditions that compromise the autonomic system.

On the right side of FIG. 20, there are two graphs showing blood flow measurements inferred by the device 100 in supine and upright positions. The top graph shows blood flow inferred by the device 100 in a supine position, while the bottom graph shows blood flow inferred by the device 100 in an upright position with a noted 30% drop in STAT flow.

In some cases, the device 100 may infer blood flow measurements based on the biometric data 1801 obtained from the biometric sensor 101. The biometric sensor 101 may be configured to record a blood flow waveform of branches of the Superficial Temporal Artery and/or Posterior Auricular Artery, which are branches of the External Carotid Artery. The device 100 may then use this biometric data 1801 to infer changes in cerebral blood flow, blood flow to the head, carotid blood flow, stroke volume (SV), and/or cardiac output (CO).

In some embodiments, the device 100 may use a machine learning model 1806 to infer these blood flow measurements. The machine learning model 1806 may be trained based on a plurality of sample data pairs to identify one or more relationships between the sample biometric data and the sample brain biometric data. Based on these relationships, the machine learning model 1806 may infer changes in cerebral blood flow, blood flow to the head, carotid blood flow, stroke volume (SV), and/or cardiac output (CO) from the biometric data 1801.

In some aspects, the device 100 may display or transmit the inferred blood flow measurements. This may involve displaying the measurements on a display of the device 100 or transmitting the measurements to a remote device via the wireless communications transceiver 105. The remote device may be a computer, a smartphone, a medical device, or any other device capable of receiving and processing the transmitted measurements.

Figure 21:
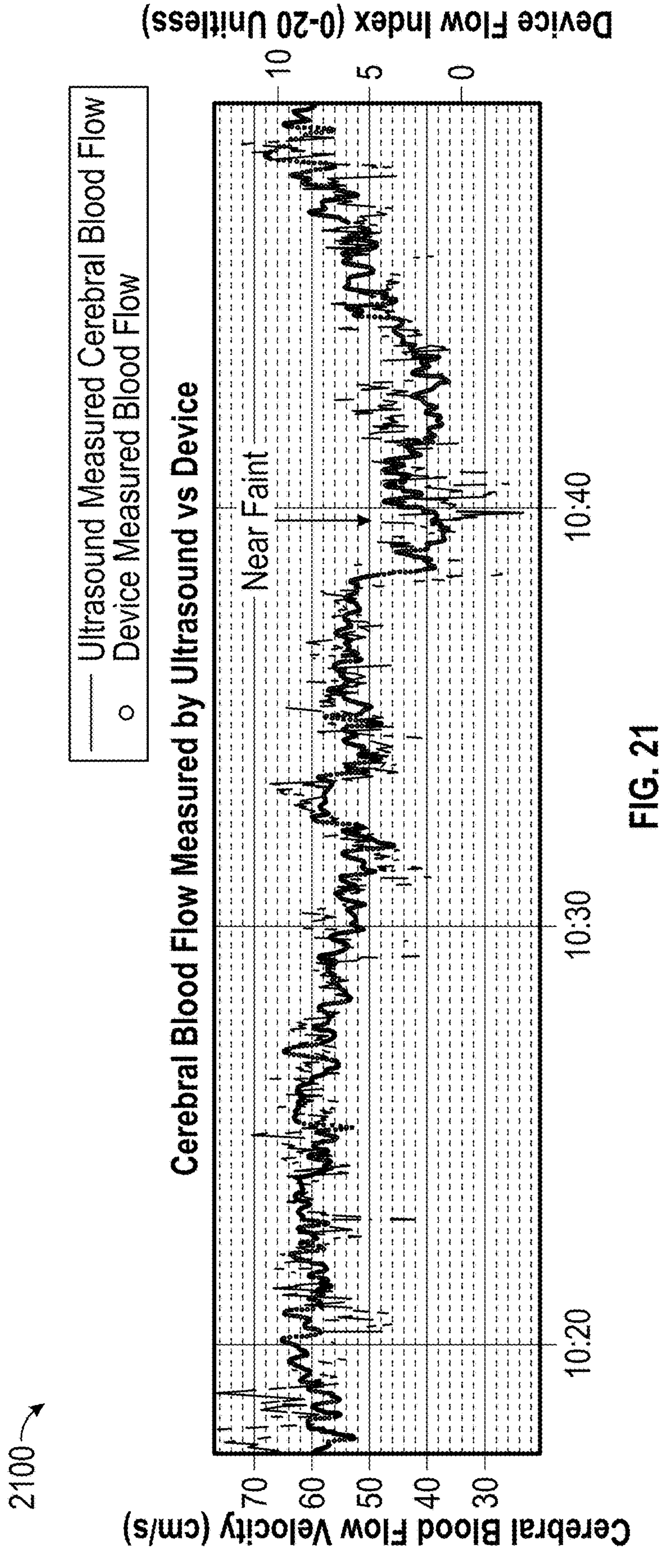
FIG. 21 illustrates a comparison graph of cerebral blood flow measurements, according to aspects of the present disclosure.

Referring to FIG. 21, the comparison graph of cerebral blood flow measurements 2100 illustrates the relationship between cerebral blood flow velocity measured by ultrasound and the device flow index measured by the in-ear device 100. The x-axis represents time, while the y-axis on the left shows cerebral blood flow velocity and the y-axis on the right shows the device flow index. The graph includes a marked event labeled "Near Faint," indicating a substantial drop in both ultrasound-measured cerebral blood flow and device-measured blood flow.

In some aspects, the cerebral blood flow velocity may be measured using a transcranial Doppler ultrasound, which provides a non-invasive method for assessing blood flow in the brain's major arteries. The device flow index, on the other hand, may be determined by the in-ear device 100 based on the biometric data 1801 obtained from the biometric sensor 101. The biometric sensor 101 may be configured to record a blood flow waveform of branches of the Superficial Temporal Artery and/or Posterior Auricular Artery, which are branches of the External Carotid Artery. The device 100 may then use this biometric data 1801 to infer changes in cerebral blood flow, blood flow to the head, carotid blood flow, stroke volume (SV), and/or cardiac output (CO).

In some cases, the marked event labeled "Near Faint" on the comparison graph of cerebral blood flow measurements 2100 may indicate a substantial drop in both ultrasound-measured cerebral blood flow and device-measured blood flow. This drop may be associated with a transition from a supine to an upright position, which can cause a reduction in cerebral blood flow due to the effects of gravity. The device 100 may be configured to detect such changes in blood flow and provide a timely alert to the user or a healthcare provider.

In other embodiments, the comparison graph of cerebral blood flow measurements 2100 may include additional marked events indicating other changes in cerebral blood flow, such as increases in blood flow associated with physical activity or decreases in blood flow associated with sleep or relaxation. These additional marked events may provide further insights into the user's cerebral blood flow patterns and may be used to inform the diagnosis or management of various neurological disorders and conditions that compromise the autonomic system.

In some aspects, the comparison graph of cerebral blood flow measurements 2100 may be displayed on a display of the device 100 or transmitted to a remote device via the wireless communications transceiver 105. The remote device may be a computer, a smartphone, a medical device, or any other device capable of receiving and processing the transmitted measurements. This may allow healthcare providers to remotely monitor the user's cerebral blood flow and provide timely interventions as appropriate.

Figure 22:
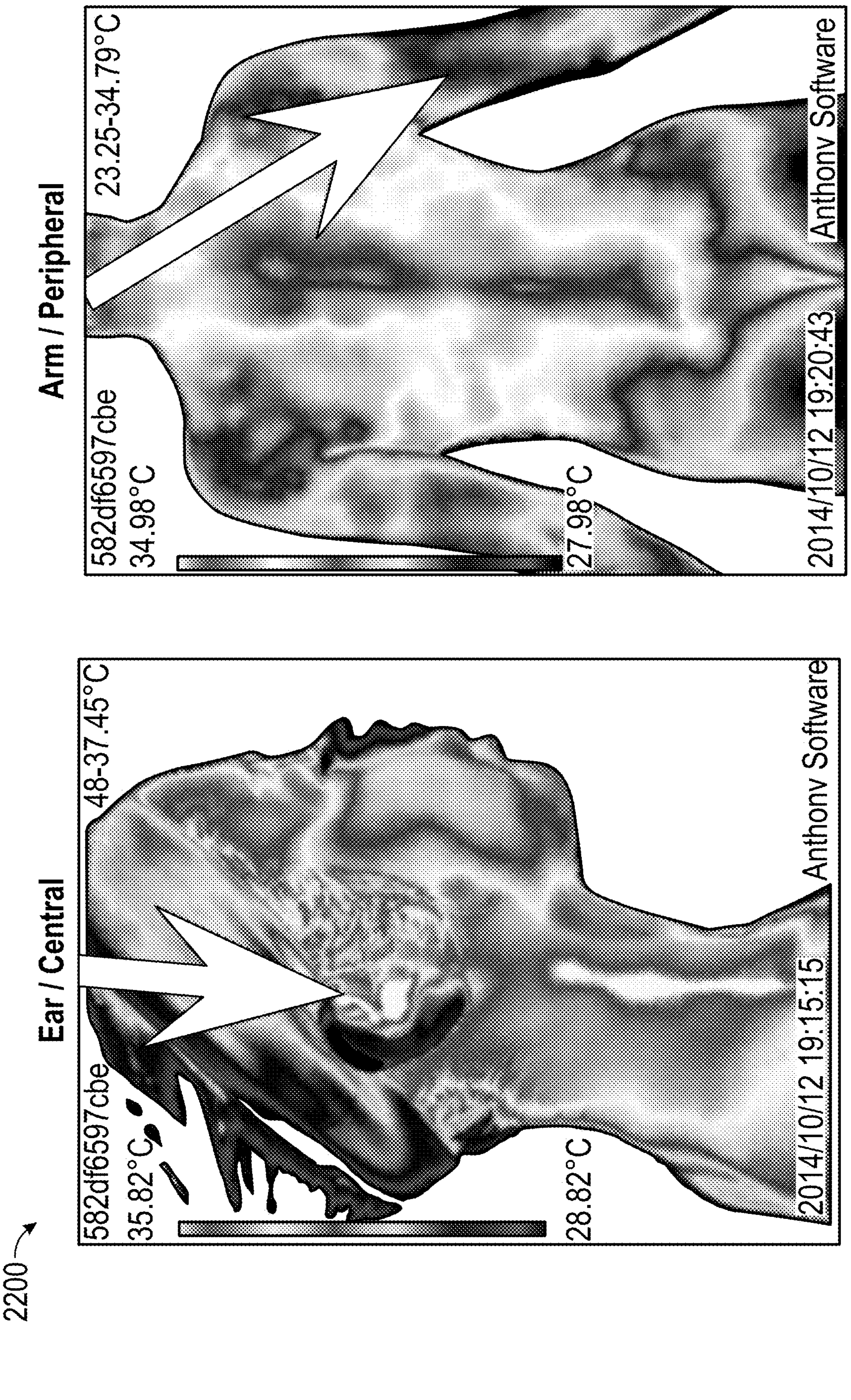
FIG. 22 presents a thermographic comparison between an ear/central region and an arm/peripheral region, according to aspects of the present disclosure.

FIG. 22 depicts a thermographic comparison 2200 between an ear/central region and an arm/peripheral region. The left image shows the thermal stability and robust perfusion of the ear/central region, indicated by a higher temperature range. The right image illustrates the arm/peripheral region, which exhibits lower temperature and poorer perfusion. The arrows in both images highlight the specific areas of interest for thermal and perfusion analysis.

In some aspects, the thermographic comparison 2200 may provide insights into the differences in temperature and perfusion between the ear/central region and the arm/peripheral region. These differences may have implications for the measurement of cerebral blood flow. For instance, the ear/central region, which exhibits higher temperature and robust perfusion, may provide a more accurate and reliable measurement of cerebral blood flow compared to the arm/peripheral region.

In some cases, the biometric sensor 101 may be configured to be removably retained against an external surface of a skin portion of the ear 1702 of the user. The ear 1702, being a part of the ear/central region, may provide a suitable location for the biometric sensor 101 due to its thermal stability and robust perfusion. The biometric sensor 101 may be configured to record a blood flow waveform of branches of the Superficial Temporal Artery and/or Posterior Auricular Artery, which are branches of the External Carotid Artery. The device 100 may then use this biometric data 1801 to infer changes in cerebral blood flow, blood flow to the head, carotid blood flow, stroke volume (SV), and/or cardiac output (CO).

In other embodiments, the biometric sensor 101 may be configured to be removably retained against an external surface of a skin portion of the arm of the user. However, due to the lower temperature and poorer perfusion of the arm/peripheral region, the measurements obtained from the arm may be less accurate or reliable compared to those obtained from the ear/central region. Therefore, in some cases, the system may preferentially use measurements obtained from the ear/central region to infer changes in cerebral blood flow, blood flow to the head, carotid blood flow, stroke volume (SV), and/or cardiac output (CO).

In some aspects, the system may display or transmit the inferred blood flow measurements. This may involve displaying the measurements on a display of the device 100 or transmitting the measurements to a remote device via the wireless communications transceiver 105. The remote device may be a computer, a smartphone, a medical device, or any other device capable of receiving and processing the transmitted measurements. This may allow healthcare providers to remotely monitor the user's cerebral blood flow and provide timely interventions as appropriate.

2.D. Flowchart

Figure 23:
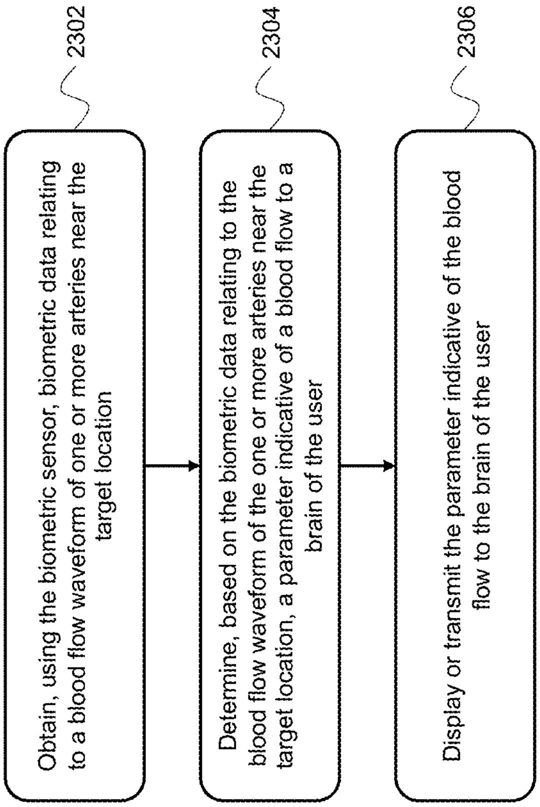
FIG. 23 depicts a flowchart diagram illustrating a method for non-invasively measuring blood flow to a brain, according to aspects of the present disclosure.

FIG. 23 depicts a flowchart diagram 2300 illustrating a method for non-invasively measuring blood flow to a brain. The method begins with obtaining biometric data step 2302, which involves using the biometric sensor 101 to collect data related to a blood flow waveform of one or more arteries near a target location. In some aspects, the biometric sensor 101 may be an optical sensor, an ultrasound transducer, a photoacoustic transducer, or an RF transducer. The target location may be an ear of the user, a temple of the user, or an underside of a wrist of the user, depending on the specific configuration of the system.

Following the obtaining biometric data step 2302, the method proceeds to determining blood flow parameter step 2304. In this step, the system determines a parameter indicative of a blood flow to a brain of the user based on the obtained biometric data. This determination may involve performing one or more computations using the biometric data and/or the blood flow waveform of the one or more arteries near the target location. The computations may be performed by a processor, a microcontroller, or any other suitable computing device. In some cases, the computations may be performed by a machine learning model that has been trained based on a plurality of sample data pairs to identify one or more relationships between the sample biometric data and the sample brain biometric data.

The parameter indicative of the blood flow to the brain of the user may be a measure of cerebral blood flow, blood flow to the head, carotid blood flow, stroke volume (SV), and/or cardiac output (CO). In some aspects, the parameter may be determined by analyzing the fullness of the blood flow waveform, calculating the area under the systolic period of the cardiac cycle, extracting features related to stroke volume (SV), or extracting carotid flow time, which is the time from the start of systole to the dichrotic notch.

After determining the blood flow parameter, the method proceeds to displaying or transmitting parameter step 2306. In this step, the system displays or transmits the parameter indicative of the blood flow to the brain of the user. The parameter may be displayed on a display of the device 100 or transmitted to a remote device via the wireless communications transceiver 105. The remote device may be a computer, a smartphone, a medical device, or any other device capable of receiving and processing the transmitted parameter. This allows for remote monitoring of the user's cerebral blood flow, which can be beneficial in diagnosing and managing conditions associated with poor cerebral blood flow.

3. OPTICAL WAVEGUIDES FOR HIGH EFFICIENCY AND HIGH QUALITY BIOSENSING

FIGS. 24-28 depict features of optical waveguides for high efficiency and high quality biosensing. FIGS. 24-28 may apply or use any of the features of FIGS. 1-16 and FIGS. 17-23 and 29-33.

Photoplethysmography (PPG) is a non-invasive method used to detect blood volume changes in the microvascular bed of tissue. It is a simple and low-cost technique that uses a light source and a photodetector at the skin surface to measure the volumetric variations of blood circulation. The light source emits light into the skin, and the photodetector measures the intensity of light that is either transmitted through or reflected off the skin. The changes in light intensity are related to changes in blood flow, and thus can provide information about the cardiovascular system.

PPG systems are commonly used in wearable devices for health monitoring, such as heart rate monitors and pulse oximeters. These devices typically use light-emitting diodes (LEDs) or lasers as the light source, and photodiodes as the photodetector. The light source and photodetector are often placed in close proximity to each other, and the light emitted by the light source is directed into the skin and then detected by the photodetector after it has been reflected off or transmitted through the skin.

The efficiency and quality of the PPG signal can be influenced by several factors, including the wavelength of the light source, the angle at which the light enters the skin, and the depth of the targeted blood vessels. Different wavelengths of light penetrate the skin to different depths, with longer wavelengths (such as infrared light) penetrating deeper than shorter wavelengths (such as green light). The angle at which the light enters the skin can also affect the path of the light through the tissue and the amount of light that is reflected back to the photodetector. Furthermore, the depth of the targeted blood vessels can affect the amount of light that is absorbed by the blood and the signal-to-noise ratio of the PPG signal.

In many PPG systems, the light source emits light in a broad pattern, often referred to as a Lambertian emission pattern. This pattern results in a large portion of the emitted light being directed away from the photodetector, which can reduce the efficiency of the system. Additionally, the light that is directed away from the target blood vessels can interact with other tissues and structures in the body, which can introduce noise into the PPG signal and reduce its quality.

The design of the optical components in a PPG system, such as the light source, photodetector, and any lenses or waveguides, can also influence the efficiency and quality of the PPG signal. For example, the design of the lens can affect the direction and focus of the emitted light, and the design of the waveguide can affect the path of the light through the tissue and the amount of light that is collected by the photodetector.

The present disclosure provides an optical waveguide system designed for use in photoplethysmography (PPG) applications. The system is designed to enhance power efficiency and signal quality in biosensing of shallow arterial beds. The optical waveguide system may include one or more optical emitters and photodiodes, along with optical waveguide cavities for the emitters. The system may also include one or more lenses that fill the optical waveguide cavities, which are designed to direct a majority of the emitted photons along an ideal photon emission path. This path is designed such that the photons enter human tissue at an exit angle 2410 in a range that is conducive to efficient and high-quality biosensing.

In some embodiments, the optical waveguide system is designed to target an arterial bed that is less than a specified depth below the surface of the skin. This design feature may allow for more efficient and accurate biosensing of shallow arterial beds. The system may also include reflective surfaces on one or more surfaces of the optical waveguide cavities, which can help to redirect emitted photons along the ideal photon emission path.

In some embodiments, the optical waveguide system may include a compliant light absorbing gasket that helps to absorb photons emitted at angles smaller than the ideal photon emission angle range. This feature may further enhance signal quality of the system. The system may also include optical waveguide cavities for one or more photodiodes, and a lower index material on one or more surfaces of the optical waveguide cavities to allow for total internal reflection.

In some embodiments, the lens of the system may be intentionally shaped in a convex, concave, or a combination of curves and faces to maximize light emission in the photon exit angle range. The lens may also protrude from the electronics housing 2402 to ensure first contact with human tissue, and may be made out of soft elastomeric material to maximize the lens' ability to conform to the skin to minimize Fresnel losses and maximize comfort.

In some embodiments, the optical emitters of the system may be Light-Emitting Diodes (LED) or Vertical Cavity Surface Emitting Lasers (VCSEL). The optical waveguide system may be adapted to attach to specific parts of the human body, such as the left auricle, and may be specifically designed to target shallow arterial branches of specific arteries.

The optical waveguide system disclosed herein may provide a more efficient and high-quality solution for biosensing of shallow arterial beds in PPG applications. The system's design features, including its optical waveguide cavities, lenses, and reflective surfaces, may contribute to its enhanced power efficiency and signal quality.

3.A. Optical Waveguides

Figure 24:
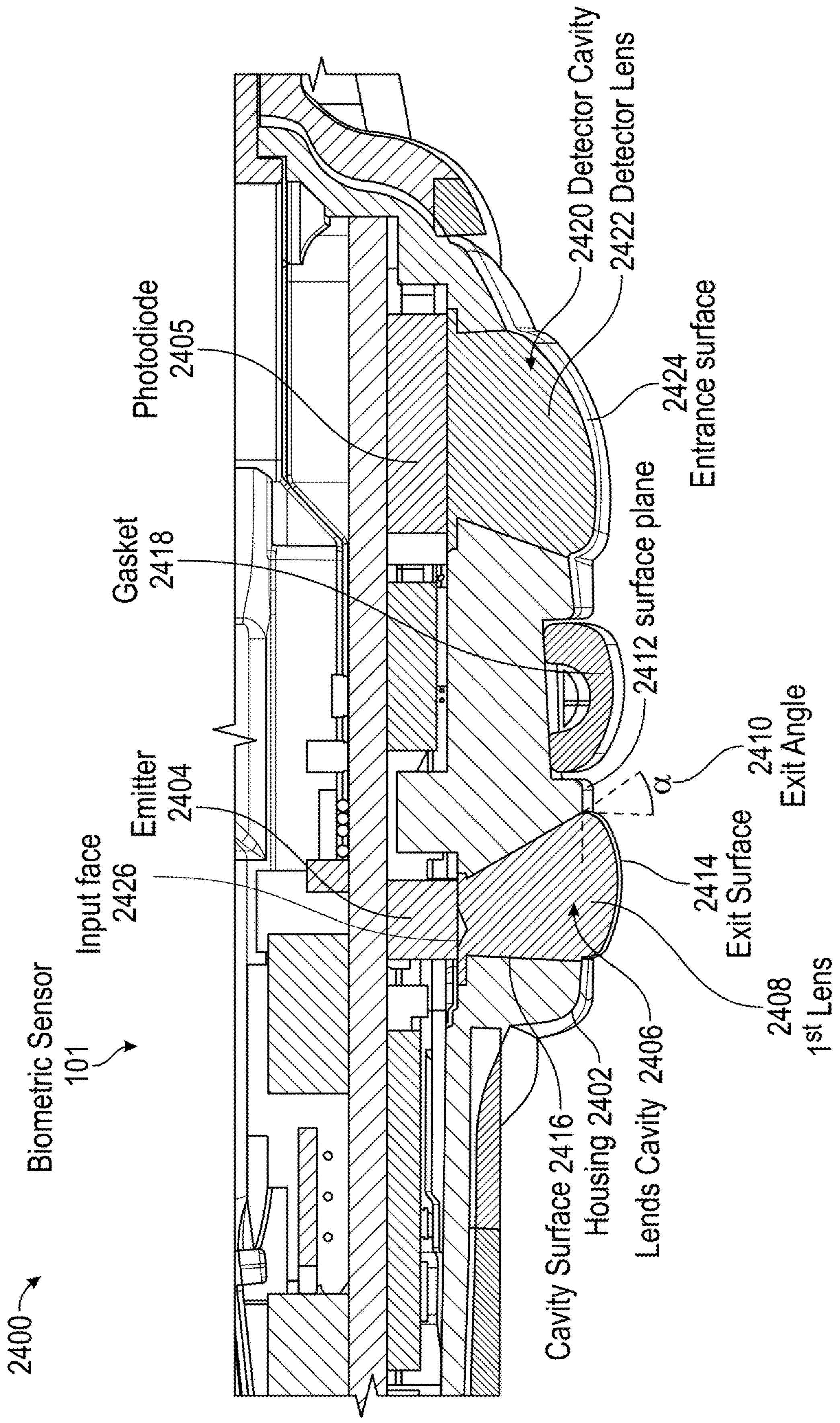
FIG. 24 depicts a cross-sectional view of an optical waveguide system with a biometric sensor, according to aspects of the present disclosure.

FIG. 24 depicts the wearable PPG system, or device 100, including a retaining insert, an emitter 2404 configured to emit photons having a wavelength of at least 590 nanometers, a photodiode 2405, a lens cavity 2406 adjacent to the emitter 2404, and at least one lens 2408 disposed within the lens cavity 2406.

In some aspects, when the wearable PPG system or device 100 is placed at a target location of a user, the lens 2408 may be configured to direct at least 75% of the photons within an exit angle 2410 ranging between 30 and 90 degrees, the exit angle range being defined relative to a surface plane 2412 of the wearable PPG system or device 100.

In some cases, the retaining insert may dispose the emitter 2404 and lens 2408 such that an arterial bed is less than 5 millimeters from an exit surface 2414 of the lens 2408 and within a path defined by the exit angle range. The arterial bed may be between 0.6 millimeters and 5 millimeters from the external surface of the skin of the user.

In some aspects, at least a portion of the photons emitted by the emitter 2404 may penetrate a tissue of the user, interact with the arterial bed, and then be redirected to and detected by the photodiode 2405.

In some cases, the lens 2408 may direct more than 90% of the photons within the exit angle range.

In some aspects, the lens cavity 2406 may include one or more surfaces 2416. The one or more surfaces 2416 may have reflective surfaces configured to reflect at least 50% of a plurality of photons that contact the one or more reflective surfaces.

In some cases, the emitter 2404 may be configured to emit the photons in a diffuse lambertian pattern, and the one or more reflective surfaces may form one or more off-axis parabolic reflectors configured to increase a collimation parameter of the plurality of photons that contact the one or more reflective surfaces.

In some aspects, the emitter 2404, lens cavity 2406, and lens 2408 may work together to direct photons towards the target location. The emitter 2404 may emit photons, which are then directed by the lens 2408 within the exit angle range towards the target location. The lens cavity 2406 may house the lens 2408 and may include one or more reflective surfaces that reflect a portion of the photons emitted by the emitter 2404, thereby increasing the number of photons that are directed towards the target location.

In some cases, the lens 2408 may be configured to direct a majority of the photons within the exit angle range, thereby improving the power efficiency and signal quality of the wearable PPG system or device 100. The lens 2408 may direct more than 90% of the photons within the exit angle range, further enhancing the power efficiency and signal quality of the wearable PPG system or device 100.

In some aspects, the lens cavity 2406 may include one or more reflective surfaces that reflect a majority of the photons that contact the one or more reflective surfaces. This feature may further enhance the power efficiency and signal quality of the wearable PPG system or device 100.

In some cases, the emitter 2404 may emit the photons in a diffuse lambertian pattern, and the one or more reflective surfaces of the lens cavity 2406 may form one or more off-axis parabolic reflectors that increase the collimation parameter of the photons. This feature may further enhance the power efficiency and signal quality of the wearable PPG system or device 100.

Referring again to FIG. 24, the optical waveguide system 2400, or device 100, may further include a compliant light absorbing gasket 2418. In some aspects, the gasket 2418 may be positioned to absorb misaligned photons emitted by the emitter 2404. These misaligned photons may be those emitted at angles smaller than the ideal photon emission angle range. By absorbing these misaligned photons, the gasket 2418 may help to enhance the signal quality of the device 100.

In some cases, the device 100 may include one or more detector cavities 2420 in which a detector lens 2422 is disposed to route photons to the photodiode 2405. The detector lens 2422 may include an entrance surface 2424. The detector cavity 2420 may be designed to house the photodiode in a manner that facilitates efficient detection of photons that have interacted with the arterial bed and have been redirected towards the photodiode.

In some aspects, the lens cavity 2406 may include one or more low-index surfaces. These low-index surfaces may have a refractive index that is lower than the refractive index of the lens 2408. In some cases, a boundary between the lens 2408 and the one or more low-index surfaces may promote total internal reflection of at least a portion of the photons emitted by the emitter 2404. This feature may further enhance the power efficiency and signal quality of the device 100 by ensuring that a majority of the emitted photons are directed towards the target location.

In some embodiments, the input face 2426 of the lens 2408 that abuts the emitter 2404 may be curved or angled. This curvature or angling of the input face 2426 may be designed to refract more photons into the exit angle range. By refracting more photons into the exit angle range, the input face 2426 may help to enhance the power efficiency and signal quality of the device 100.

In some aspects, the exit surface 2414 of the lens 2408 may protrude beyond the surface plane 2412 of the device 100. This protrusion of the exit surface 2414 may ensure that, when the device 100 is placed at the target location, the exit surface 2414 of the lens 2408 contacts the external surface of the skin of the user. This contact between the exit surface 2414 and the skin of the user may help to minimize Fresnel losses and maximize comfort for the user.

Referring again to FIG. 24, the emitter 2404 of the optical waveguide system 2400, or device 100, may be a light emitting diode (LED) in some aspects. In other cases, the emitter 2404 may be a vertical cavity surface emitting laser (VCSEL). Both types of emitters 2404 are capable of emitting photons with a wavelength of at least 590 nanometers, which is suitable for penetrating human tissue and interacting with an arterial bed.

In operation, the emitter 2404 emits photons, which are then directed by the lens 2408 within the exit angle range towards the target location. In some aspects, the lens 2408 is configured to direct at least 75% of the photons within an exit angle range between 30 and 90 degrees. This exit angle range is defined relative to a surface plane 2412 of the device 100. By directing a majority of the photons within this exit angle range, the lens 2408 enhances the power efficiency and signal quality of the device 100.

In some cases, the photons emitted by the emitter 2404 penetrate a tissue of the user, interact with the arterial bed, and are then redirected. These redirected photons are detected by a photodiode. The photodiode is configured to detect the redirected photons that have interacted with the arterial bed. This interaction between the photons and the arterial bed provides valuable information about the blood flow in the arterial bed, which can be used for various biosensing applications.

In some aspects, the photodiode is disposed within one or more detector cavities 2420. The detector cavity 2420 is designed to house the photodiode in a manner that facilitates efficient detection of photons that have interacted with the arterial bed and have been redirected towards the photodiode. This arrangement of the photodiode within the detector cavity 2420 further enhances the power efficiency and signal quality of the device 100.

3.B. Photon Collection

Figure 25:
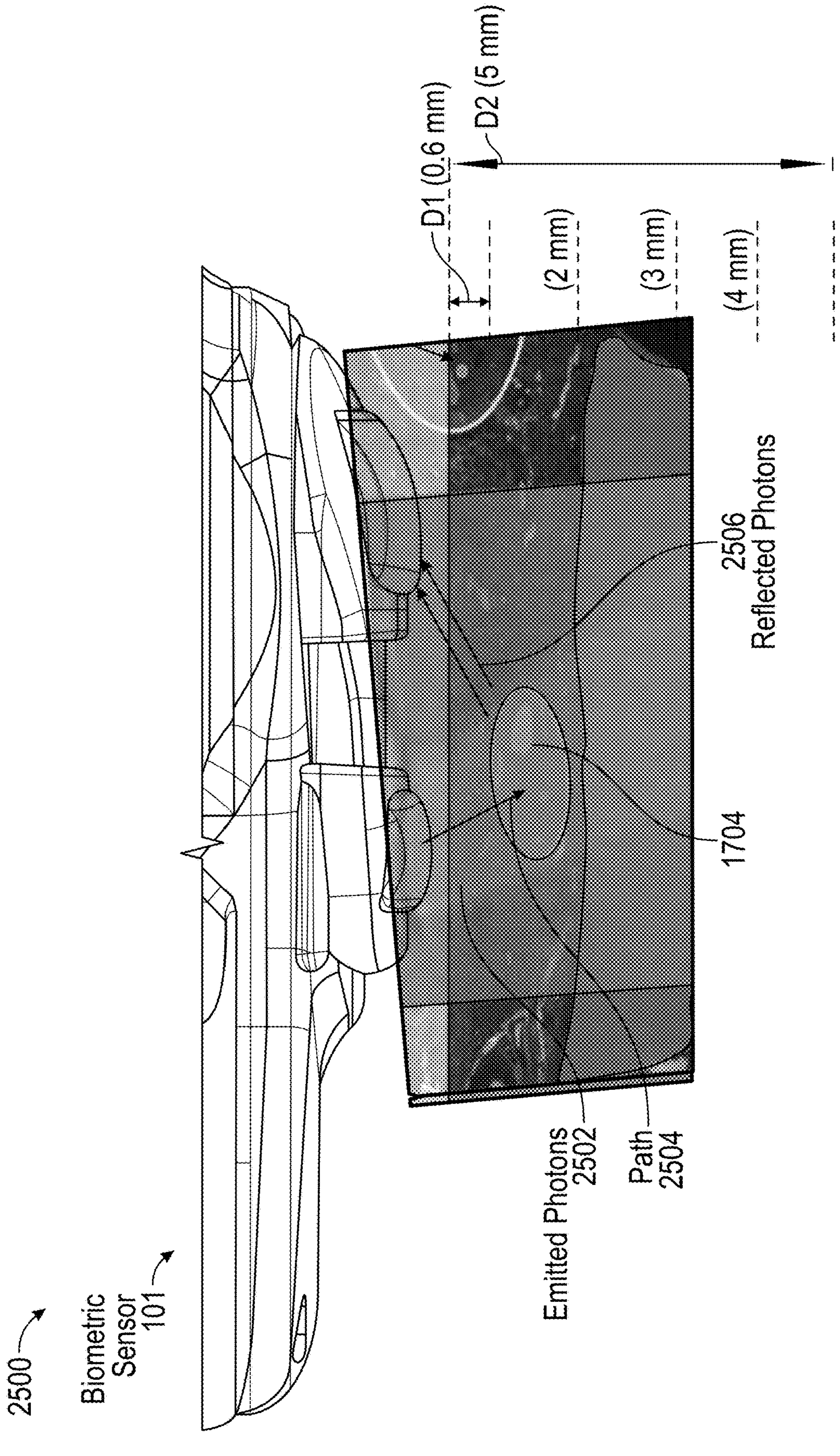
FIG. 25 shows a cross-sectional view of a photoplethysmography system with emitted and reflected photons, according to aspects of the present disclosure.

FIG. 25 depicts a cross-sectional view of the PPG system 2500, or device 100, illustrating the process of photon emission, interaction with the arterial bed 1704, and detection by the photodiode. In some aspects, the retaining insert positions the emitter 2404 and lens 2408 such that the arterial bed 1704 is within a specific distance from the lens 2408 and within the path 2504 defined by the exit angle range. This positioning may be such that the arterial bed 1704 is less than 5 millimeters from an exit surface 2414 of the lens 2408 and within a path defined by an exit angle range between 30 and 90 degrees relative to a surface plane 2412. The arterial bed 1704 may be between 0.6 millimeters and 5 millimeters from the external surface of the skin of the user.

In some cases, a portion of the photons emitted by the emitter 2404, referred to as emitted photons 2502, may penetrate the user's tissue, interact with the arterial bed 1704, and then be redirected as reflected photons 2506 to be detected by the photodiode. This interaction between the emitted photons 2502 and the arterial bed 1704 provides valuable information about the blood flow in the arterial bed 1704, which can be used for various biosensing applications.

In some aspects, the device 100 may be placed at a target location of the user such that the exit surface 2414 of the lens 2408 is less than 5 millimeters from the arterial bed 1704 and the arterial bed 1704 is within a path defined by an exit angle range between 30 and 90 degrees relative to a surface plane 2412. The arterial bed 1704 may be between 0.6 millimeters and 5 millimeters from the external surface of the skin of the user.

In some cases, the target location may be an ear of the user to target a posterior auricular artery of the user, a temple of the user to target a superficial temporal artery of the user, or an underside of a wrist of the user to target a radial artery of the user. These target locations are chosen due to the presence of shallow arterial beds that are less than 5 millimeters from the surface of the skin, making them ideal for biosensing applications.

In some aspects, the arterial bed 1704 may comprise an arterial branch of an external carotid artery. This arterial branch may be a shallow artery that is less than 5 millimeters below the surface of the skin, making it an ideal target for the device 100. The arterial branch may be a branch of the posterior auricular artery or the superficial temporal artery, depending on the target location.

3.C. Comparison and Wavelength

Figure 26:
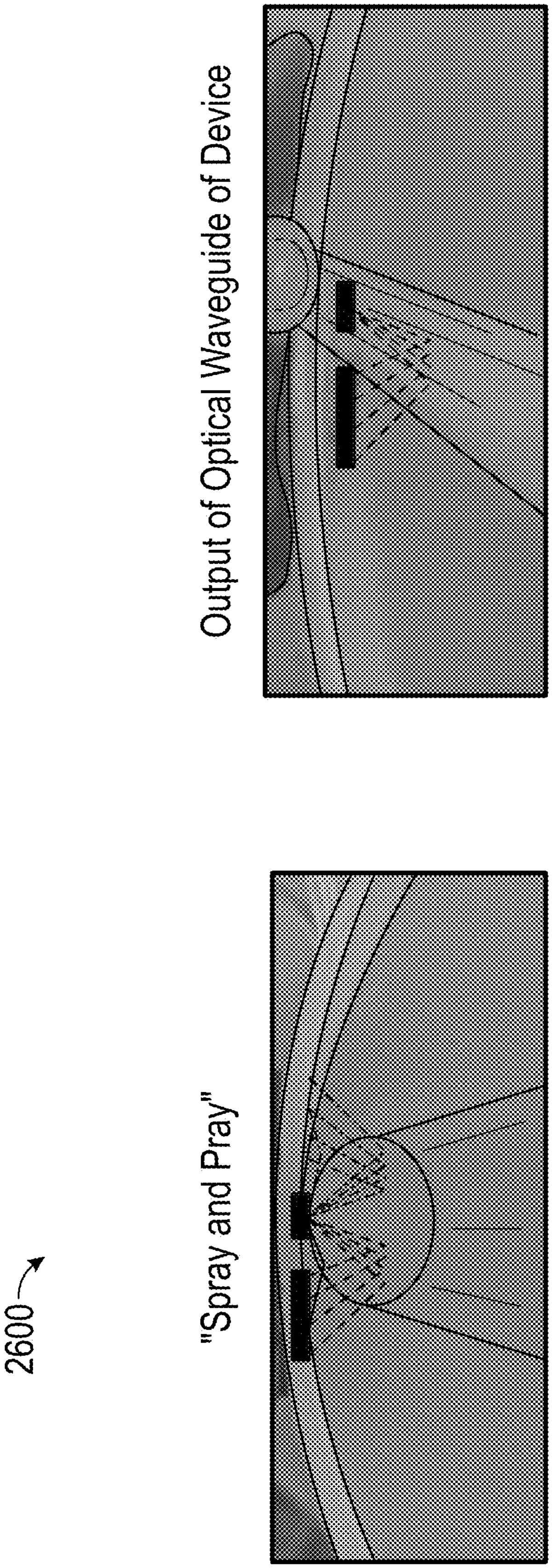
FIG. 26 compares optical waveguide designs for biometric monitoring, demonstrating an advanced design, according to aspects of the present disclosure.

FIG. 26 depicts a comparison 2600 is made between traditional PPG sensors and a PPG sensor of the present disclosure with an optical waveguide designed for biometric monitoring.

In some aspects, traditional wearables, as depicted on the left side of the figure, emit photons indiscriminately. This indiscriminate emission of photons results in photons emitted in a direction opposite from the receiving photodiode, represented by the yellow lines, leading to wasted energy and increased noise in the signal.

In contrast, the optical waveguide of the present PPG sensor, as depicted on the right side of the figure, directs photons more precisely towards the target arteries. This precision is achieved through the use of an optical waveguide system 2400, which may include an emitter 2404, a lens cavity 2406, and a lens 2408. The lens 2408 is designed to direct a majority of the emitted photons within an exit angle range, enhancing the likelihood of photon interaction with the arteries and subsequent detection by the photodiode.

In some cases, the optical waveguide of the present PPG sensor may reduce power usage by directing a majority of the emitted photons towards the target arteries, thereby reducing the number of photons that are wasted. This reduction in power usage may be particularly beneficial in wearable devices, where battery life is often a limiting factor.

In some aspects, the optical waveguide of the present PPG sensor may also enhance signal quality by directing photons more precisely towards the target arteries. This precision may reduce the amount of noise in the signal, leading to more accurate and reliable biometric monitoring.

In some cases, the optical waveguide of the present PPG sensor may be used in a variety of applications, including but not limited to health and wellness monitoring, fitness tracking, sleep tracking, stress management, and other types of applications. The optical waveguide of the present PPG sensor may also be used in a variety of settings, including but not limited to home, office, gym, outdoor, healthcare facility, research facility, and other types of settings.

In some aspects, the optical waveguide of the present PPG sensor may be used in conjunction with other devices, systems, or services, such as smartphones, tablets, computers, servers, cloud-based services, and other types of devices, systems, or services. The optical waveguide of the present PPG sensor may be configured to communicate with these other devices, systems, or services via wired or wireless communications links, and may exchange data with these other devices, systems, or services for various purposes, such as data processing, data analysis, data storage, data visualization, and other types of purposes.

In some cases, the optical waveguide of the present PPG sensor may be used in conjunction with other types of sensors, devices, or systems, such as other types of biometric sensors, environmental sensors, activity sensors, and other types of sensors, devices, or systems. The advanced optical design may be configured to integrate the data from these other sensors, devices, or systems with the data from the biometric sensor 101, and may use this integrated data for various purposes, such as health and wellness monitoring, fitness tracking, sleep tracking, stress management, and other types of purposes.

Figure 27:
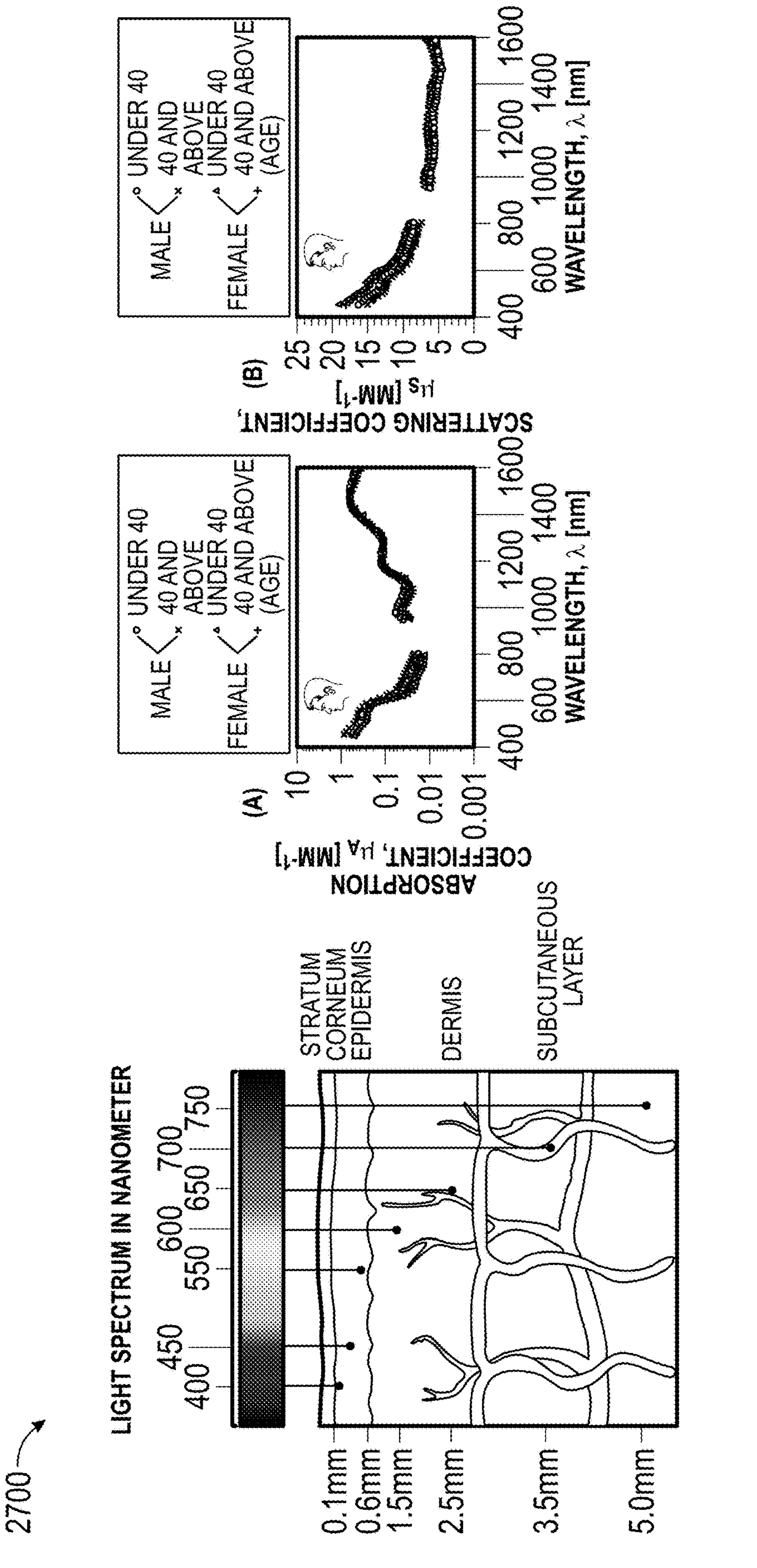
FIG. 27 presents a cross-sectional view of human skin layers and their interaction with different wavelengths of light, according to aspects of the present disclosure.

FIG. 27 depicts diagrams 2700 for the interaction of different light wavelengths with various layers of human skin. In some aspects, the figure illustrates the penetration of various light wavelengths, ranging from 400 nanometers to 750 nanometers, through different skin layers, including the Stratum corneum, Epidermis, Dermis, and Subcutaneous layer. The depth markers indicate the penetration depths at 0.1 millimeters, 0.6 millimeters, 1.5 millimeters, 2.5 millimeters, 3.5 millimeters, and 5.0 millimeters.

In some cases, the figure also includes two graphs showing absorption and scattering coefficients as a function of wavelength for different age and gender groups. These graphs provide average values for males and females under and over the age of 40. The absorption coefficient graph shows how much of the light is absorbed by the skin at different wavelengths, while the scattering coefficient graph shows how much of the light is scattered by the skin at different wavelengths.

In some aspects, the interaction of light with human skin can vary depending on the wavelength of the light. For example, shorter wavelengths, such as blue or green light, may be absorbed more by the skin and may not penetrate as deeply as longer wavelengths, such as red or infrared light. This can be seen in the figure, where green light is shown to penetrate less deeply into the skin than red or infrared light.

In some cases, the interaction of light with human skin can also vary depending on the age and gender of the individual. For example, the skin of older individuals may absorb more light than the skin of younger individuals, and the skin of males may absorb more light than the skin of females. This can be seen in the figure, where the absorption and scattering coefficients are shown to vary for different age and gender groups.

In some aspects, the device 100 may be configured to emit light at a wavelength that is optimized for penetration into the skin and interaction with the arterial bed 1704. For example, the emitter 2404 may be configured to emit light at a wavelength of at least 590 nanometers, which is within the red or infrared range. This wavelength may allow the light to penetrate more deeply into the skin and interact more effectively with the arterial bed 1704, thereby enhancing the power efficiency and signal quality of the device 100. Wavelengths longer than 590 nanometers can better reach their target vasculature through human tissue, because they penetrate deeper and stay more focused. This is a part of the present disclosure that provides benefits of imbuing emitted photons with directionality.

In some cases, the device 100 may be configured to adjust the wavelength of the emitted light based on the age and gender of the user. For example, the device 100 may emit light at a longer wavelength for older individuals or males, who may have skin that absorbs more light, and at a shorter wavelength for younger individuals or females, who may have skin that absorbs less light. This feature may further enhance the power efficiency and signal quality of the device 100 by optimizing the interaction of the light with the skin and the arterial bed 1704.

3.D. Flowchart

Figure 28:
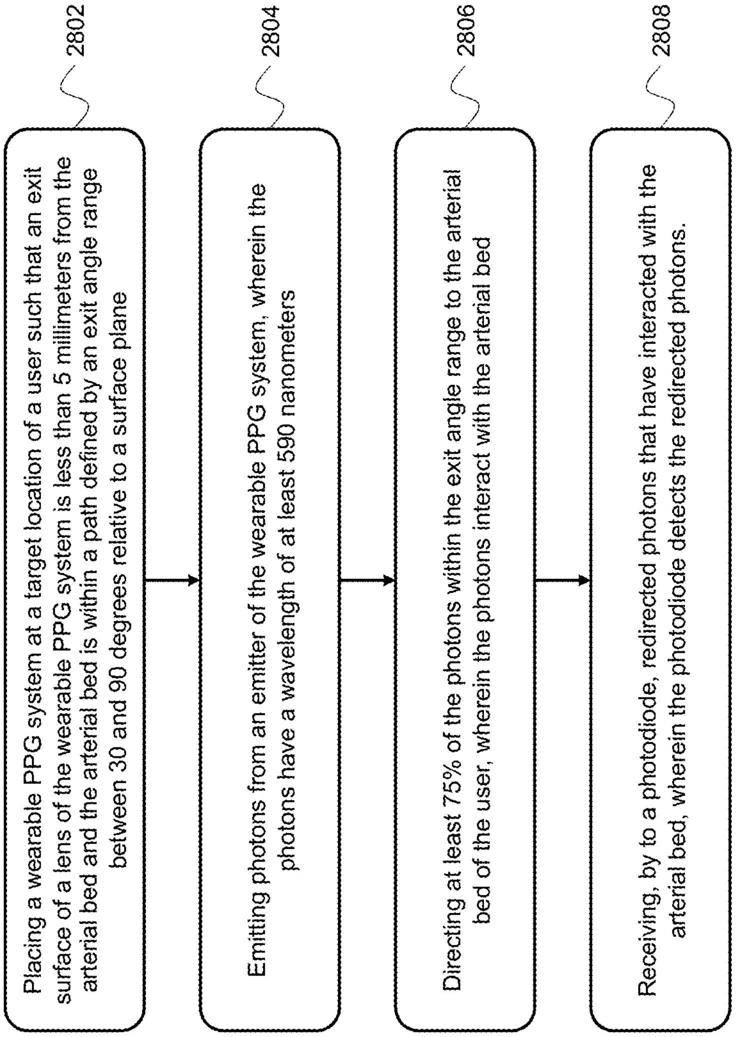
FIG. 28 outlines a flowchart of a method for monitoring blood flow in an arterial bed using a wearable photoplethysmography system, according to aspects of the present disclosure.

FIG. 28 depicts a method 2800 for monitoring blood flow in an arterial bed using a wearable photoplethysmography system (wearable PPG system) is depicted. The method 2800 may begin with placing the wearable PPG system 2802 at a target location of a user. In some aspects, the target location may be an ear of the user to target a posterior auricular artery of the user, a temple of the user to target a superficial temporal artery of the user, or an underside of a wrist of the user to target a radial artery of the user. These target locations are chosen due to the presence of shallow arterial beds that are less than 5 millimeters from the surface of the skin, making them ideal for biosensing applications.

In some cases, when the wearable PPG system 2802 is placed at the target location, an exit surface 2414 of a lens 2408 of the wearable PPG system is less than 5 millimeters from the arterial bed and the arterial bed is within a path defined by an exit angle range between 30 and 90 degrees relative to a surface plane 2412. The arterial bed may be between 0.6 millimeters and 5 millimeters from the external surface of the skin of the user.

The method 2800 may then involve emitting photons 2804 from an emitter 2404 of the wearable PPG system. In some aspects, the photons may have a wavelength of at least 590 nanometers. This wavelength may allow the photons to penetrate more deeply into the skin and interact more effectively with the arterial bed, thereby enhancing the power efficiency and signal quality of the wearable PPG system.

The method 2800 may further involve directing at least 75% of the photons within the exit angle range to the arterial bed 2806 of the user. In some cases, the lens 2408 of the wearable PPG system may be configured to direct the photons. By directing a majority of the photons within the exit angle range, the lens 2408 may enhance the power efficiency and signal quality of the wearable PPG system.

The method 2800 may also involve receiving, by a photodiode, redirected photons 2808 that have interacted with the arterial bed. In some aspects, the photodiode may be disposed within one or more detector cavities 2420. The detector cavity 2420 may be designed to house the photodiode in a manner that facilitates efficient detection of photons that have interacted with the arterial bed and have been redirected towards the photodiode. This arrangement of the photodiode within the detector cavity 2420 further enhances the power efficiency and signal quality of the wearable PPG system.

In some cases, the method 2800 may be used in a variety of applications, including but not limited to health and wellness monitoring, fitness tracking, sleep tracking, stress management, and other types of applications. The method 2800 may also be used in a variety of settings, including but not limited to home, office, gym, outdoor, healthcare facility, research facility, and other types of settings.

4. EAR INTERFACE MECHANISMS

FIGS. 29-33 depict features of ear interface mechanisms. FIGS. 29-33 may apply or use any of the features of FIGS. 1-16 and FIGS. 17-23 and 24-28.

Wearable electronic devices, particularly those designed for placement in the ear, have become increasingly popular due to their convenience and versatility. These devices can serve a variety of functions, ranging from audio playback to biometric monitoring. The ear, specifically the Cymba Concha, is a particularly advantageous location for such devices due to its proximity to the brain and the presence of various physiological features that can be monitored.

The Cymba Concha is a small, bowl-shaped depression in the external ear, located just above the earlobe. It is surrounded by several anatomical features, including the Antihelix, a curved prominence of cartilage, and the Antitragus, a small tubercle opposite the tragus. The Cavum Concha is the main cavity of the external ear, located adjacent to the Cymba Concha.

Biometric sensors are devices that measure and analyze human physical and behavioral characteristics. These sensors can be used to monitor a variety of physiological parameters, such as heart rate, blood oxygen levels, and body temperature. In the context of ear-worn devices, these sensors often require direct contact with the skin to function effectively.

The design and placement of wearable devices in the ear can be challenging due to the complex anatomy of the ear and the wide variation in ear shapes and sizes among individuals. The device's fit and stability in the ear are of paramount concern, as these factors can affect both the comfort of the wearer and the accuracy of any biometric sensors included in the device.

In some designs, compliant elements, such as legs or shims, are used to secure the device in the ear. These elements can be designed to hook under or press against various anatomical features of the ear, such as the Antihelix or Antitragus, to help retain the device in place. The compliance of these elements can be adjusted to accommodate different ear shapes and sizes.

In addition to fit and stability, the positioning of biometric sensors in ear-worn devices is also a major design consideration. The sensors often require direct contact with the skin and may be oriented in specific directions to target particular physiological features or signals. For example, an optical biometric sensor may be aimed medially, or towards the middle of the body, to target a shallow arterial branch in the ear.

In summary, the design of ear-worn electronic devices involves a complex interplay of factors, including the anatomy of the ear, the fit and stability of the device, and the positioning and operation of any included biometric sensors.

The present disclosure provides an ear interface mechanism for wearable electronic devices. This mechanism is designed to ensure the secure positioning of the device within the Cymba Concha of the user's ear. The design of the mechanism allows for the device's rigid housing 2402 to be entirely contained within the Cymba Concha, providing a comfortable and secure fit for the user.

The ear interface mechanism includes a device body that is designed to tuck underneath the Antihelix of the user's ear. This design feature contributes to the secure positioning of the device within the ear. The mechanism also includes one or more compliant retaining legs that extend from the device body into the Cavum Concha. These legs are designed to tuck under the Antitragus of the user's ear, further ensuring the retention of the device within the ear.

In addition to securing the device within the ear, the ear interface mechanism also ensures the proper positioning and contact of a biometric sensor with the user's ear. The biometric sensor is placed in the Cymba Concha and is aimed medially. The device body is designed to press into the underside of the Antihelix, applying a medial counterforce on the biometric sensor. This counterforce ensures that the biometric sensor maintains contact with the floor of the Cymba Concha, allowing for accurate biometric readings.

The ear interface mechanism may also include a mechanical connection to an element positioned in the Cavum Concha. This mechanical connection applies a medial counterforce on the biometric sensor, further ensuring its proper positioning and contact with the user's ear.

In some cases, the ear interface mechanism may include a shim that fills a variable gap between the device body and the Antihelix. This shim is designed to press into the underside of the Antihelix, applying a medial counterforce on the device body. The shim may be constructed with an air-filled cavity to increase its compliance, allowing for a more adaptable fit across different ear sizes.

The ear interface mechanism may also include a compliant nose that extends under the Helix of the user's ear. This nose helps in the proper positioning of the biometric sensor, allowing it to be better mechanically decoupled from jaw artifacts that may be present when the user chews or talks.

The ear interface mechanism may also include a compliant jacket that enshrouds the majority of the device body. This jacket allows for a modular and independently tunable combination of leg sizes, shim sizes, and nose sizes, providing a customizable fit for different users.

The present disclosure also provides a light-sealing gasket that improves the performance of any optical biometric sensor used in the device. This gasket may be constructed with an air-filled cavity to increase its compliance, allowing for more adaptability to block light for different ear curvatures.

Overall, the ear interface mechanism described herein provides a secure and comfortable fit for wearable electronic devices within the user's ear, while ensuring the proper positioning and contact of a biometric sensor with the user's ear.

4.A. Insert Features

FIG. 29-32 depict features of a wearable insert for an ear.

Figure 29:
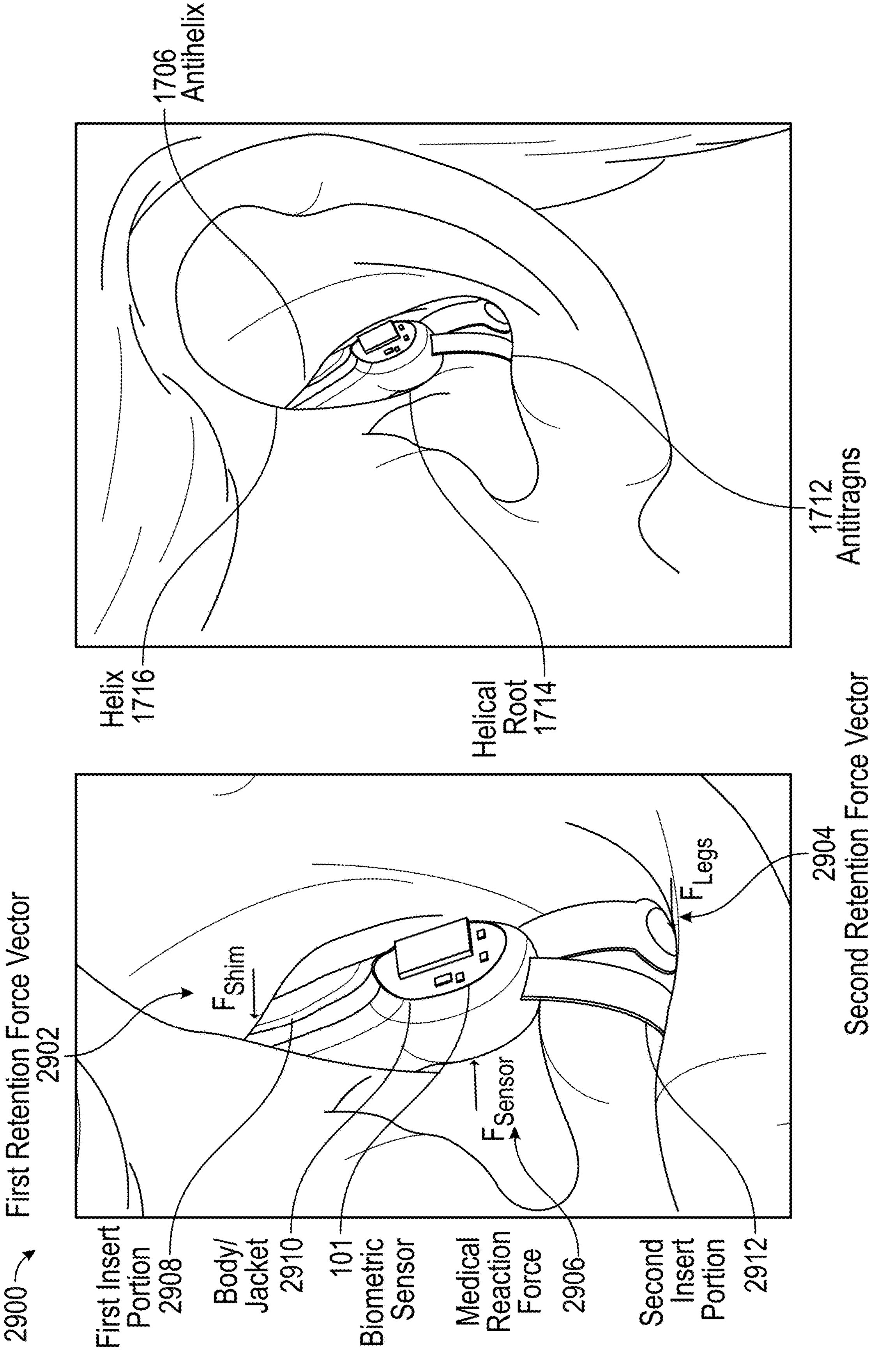
FIG. 29 illustrates a wearable insert positioned within the ear, according to aspects of the present disclosure.

FIG. 29 depicts a wearable insert 2900 positioned within the ear. The first insert portion 2908 of the wearable insert 2900 is configured to abut the antihelix 1706 of the user's ear. In some aspects, the first insert portion 2908 may be designed to conform to the shape of the antihelix 1706, providing a secure and comfortable fit. When the wearable insert 2900 is positioned within the ear, the engagement between the first insert portion 2908 and the antihelix 1706 applies a first retention force vector 2902 to the wearable insert 2900. This first retention force vector 2902 is oriented at least partially medially, contributing to the secure positioning of the wearable insert 2900 within the ear.

The wearable insert 2900 also includes a second insert portion 2912 that is configured to be disposed at least partially within a cymba cavum of the ear. In some cases, the second insert portion 2912 may include one or more legs that extend into the cavum concha. These legs are designed to tuck under the antitragus 1712 of the ear, providing additional retention for the wearable insert 2900 within the ear. The engagement between the second insert portion 2912 and the antitragus 1712 applies a second retention force vector 2904 to the wearable insert 2900. This second retention force vector 2904, in combination with the first retention force vector 2902, retains the wearable insert 2900 such that the biometric sensor 101 is pressed medially toward an external surface of a skin portion of the cymba concha of the ear, thereby forming a medial reaction force 2906.

The wearable insert 2900 also includes a cavity that is configured to hold the biometric sensor 101. This cavity is enclosed by a body/jacket 2910, which may be constructed from a compliant material to provide a comfortable fit for the user. The body/jacket 2910 may also be designed to protect the biometric sensor 101 from external forces and environmental conditions, ensuring the reliable operation of the sensor.

In some aspects, the second insert portion 2912 may be attached to the body/jacket 2910. This attachment may be achieved through various means, such as adhesive bonding, mechanical fastening, or integral molding. The second insert portion 2912 and the body/jacket 2910 may be constructed from the same or different materials, depending on the desired properties of the wearable insert 2900. For example, the second insert portion 2912 may be constructed from a more rigid material to provide structural support, while the body/jacket 2910 may be constructed from a more compliant material to provide so that the biometric sensor 101 is removable from the cavity.

The cavity of the wearable insert 2900 is enclosed by a jacket portion 2910. In some aspects, the jacket portion 2910 may be designed to protect the biometric sensor 101 from external forces and environmental conditions, ensuring the reliable operation of the sensor. The jacket portion 2910 may also provide a comfortable fit for the user, as it may be constructed from a compliant material. In some cases, the jacket portion 2910 may be attached to one or more legs that extend from the device body into the Cavum Concha. These legs are designed to tuck under the Antitragus 1712 of the user's ear, providing additional retention for the wearable insert 2900 within the ear.

The engagement between the second insert portion 2912 and an ear portion against which the second insert portion 2912 abuts applies a second retention force vector 2904 to the wearable insert 2900. In some aspects, the second retention force vector 2904 is oriented at least partially medially. This orientation of the second retention force vector 2904, in combination with the first retention force vector 2902, retains the wearable insert 2900 such that the biometric sensor 101 is pressed medially toward an external surface of a skin portion of the cymba concha of the ear.

In some cases, the wearable insert 2900 may include a shim that extends along and contacts a length of at least 4 millimeters of the antihelix 1706. This shim is designed to press into the underside of the antihelix 1706, applying a medial counterforce on the device body. The shim may be constructed with an air-filled cavity to increase its compliance, allowing for a more adaptable fit across different ear sizes.

The wearable insert 2900 may also include a nose portion that is disposed between a helix 1716 and the external surface of the skin portion of the cymba concha of the ear. In some aspects, the nose portion may help in the proper positioning of the biometric sensor 101, allowing it to be better mechanically decoupled from jaw artifacts that may be present when the user chews or talks. The nose portion may also contribute to the secure positioning of the wearable insert 2900 within the ear.

The wearable insert 2900 may comprise an aperture that is positioned less than five (5) millimeters from a branch of a posterior auricular artery that perforates an auricular cartilage that protrudes at an anterior face of the ear. This positioning of the aperture is strategic, as it allows the biometric sensor 101 to target a shallow arterial branch that perforates the cartilage at the helical root 1714 to emerge at the anterior face of the ear. This arterial branch may be a rich source of biometric data, making it a desirable target for the biometric sensor 101.

The aperture is located between the cavity of the wearable insert 2900 and the external surface of a skin portion of the cymba concha of the ear. This positioning ensures that the biometric sensor 101 is pressed medially toward the external surface of the skin portion of the cymba concha of the ear. This medial pressure is achieved through the application of the first retention force vector 2902 and the second retention force vector 2904.

The first retention force vector 2902 is applied through the engagement between the first insert portion 2908 and the antihelix 1706. When the wearable insert 2900 is positioned within the ear, the first insert portion 2908 abuts the antihelix 1706, applying a medial force that contributes to the secure positioning of the wearable insert 2900 within the ear.

The second retention force vector 2904 is applied through the engagement between the second insert portion 2912 and an ear portion against which the second insert portion 2912 abuts. In some cases, the second insert portion 2912 may include one or more legs that extend into the cavum concha. These legs are designed to tuck under the antitragus 1712 of the ear, providing additional retention for the wearable insert 2900 within the ear.

The combination of the first retention force vector 2902 and the second retention force vector 2904 retains the wearable insert 2900 such that the biometric sensor 101 is pressed medially toward an external surface of a skin portion of the cymba concha of the ear. This medial pressure ensures that the biometric sensor 101 maintains contact with the floor of the cymba concha, allowing for accurate biometric readings.

Figure 30:
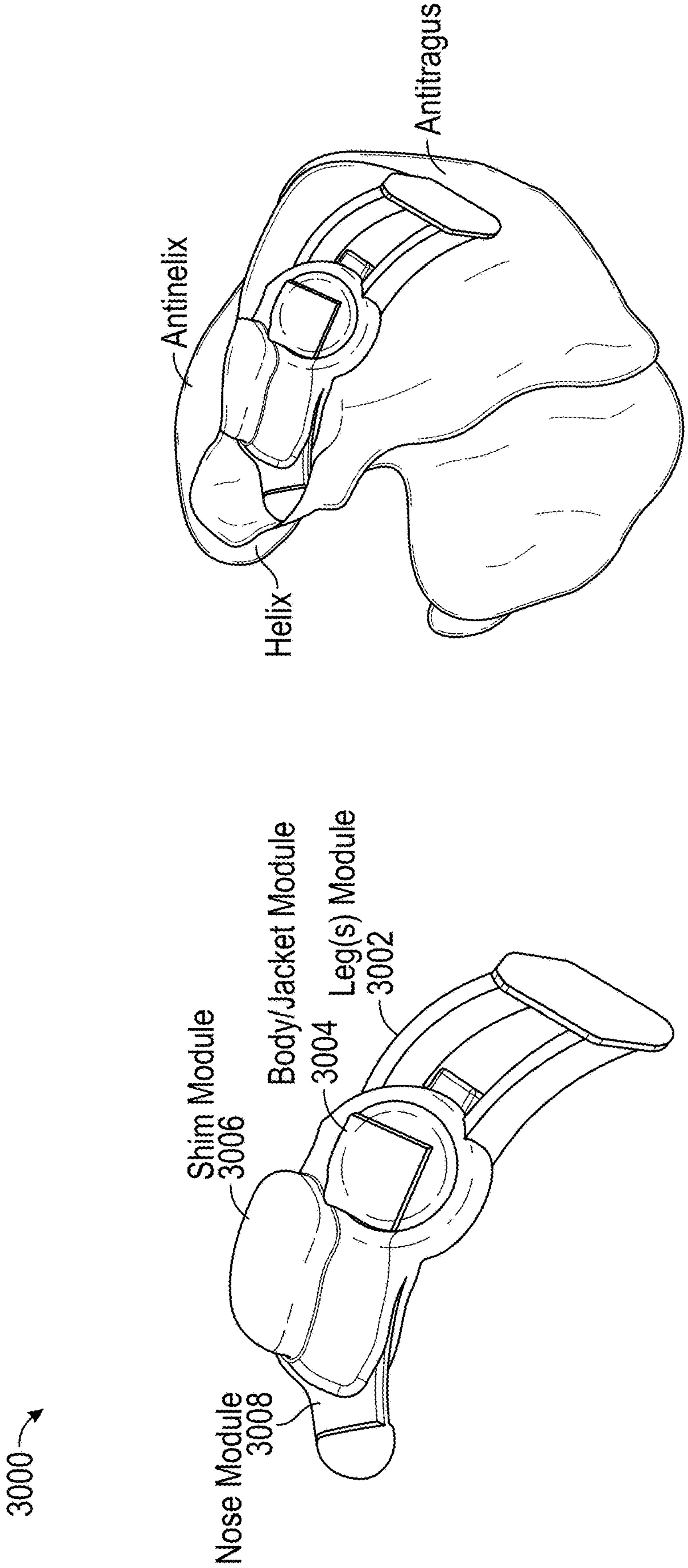
FIG. 30 depicts an ear interface mechanism with various modules, according to aspects of the present disclosure.

FIG. 30 depicts an ear interface mechanism 3000. The ear interface mechanism 3000 includes a jacket module 3004 that encloses a biometric sensors 101. In some aspects, the jacket module 3004 may be designed to protect the biometric sensor 101 from external forces and environmental conditions, ensuring the reliable operation of the sensor. The jacket module 3004 may also provide a comfortable fit for the user, as it may be constructed from a compliant material.

Extending from the jacket module 3004 are legs module 3002, which are designed to provide structural support and retention by tucking under the antitragus 1712. In some cases, the legs module 3002 may include one or more legs that extend into the cavum concha. These legs are designed to tuck under the antitragus 1712 of the ear, providing additional retention for the ear interface mechanism 3000 within the ear.

A shim module 3006 is positioned to abut the antihelix 1706, ensuring a secure fit and applying the first retention force vector 2902 for sensor contact. In some aspects, the shim module 3006 may be designed to conform to the shape of the antihelix 1706, providing a secure and comfortable fit. The shim module 3006 may be constructed with an air-filled cavity to increase its compliance, allowing for a more adaptable fit across different ear sizes.

Additionally, a nose module 3008 extends under the helix 1716, aiding in the proper positioning and stability of the ear interface mechanism 3000 within the ear. In some cases, the nose module 3008 may help in the proper positioning of the biometric sensor 101, allowing it to be better mechanically decoupled from jaw artifacts that may be present when the user chews or talks. The nose module 3008 may also contribute to the secure positioning of the ear interface mechanism 3000 within the ear. In some aspects, the nose module 3008 may be optional, based on the two-dimensional rescaled image or three-dimensional reconstructed model of the user's ear.

The jacket module 3004 is attached to the leg module 3002, the shim module 3006, and the nose module 3008. This attachment may be achieved through various means, such as adhesive bonding, mechanical fastening, or integral molding. The jacket module 3004, the leg module 3002, the shim module 3006, and the nose module 3008 may be constructed from the same or different materials, depending on the desired properties of the ear interface mechanism 3000. For example, the jacket module 3004 may be constructed from a more compliant material to provide comfort for the user, while the leg module 3002 may be constructed from a more rigid material to provide structural support.

In some cases, the jacket module 3004 may be removable from the biometric sensor 101 by a user, allowing for easy adjustment to a different combination of the leg module 3002, the nose module 3008, and the shim module 3006. This modular design allows for a customizable fit for different users, accommodating the natural diversity of human ear shapes and sizes. The leg module 3002, the nose module 3008, and the shim module 3006 are each selected from a plurality of respective modules having different sizes to fit the ear of the user. This selection may be based on a two-dimensional or three-dimensional smartphone-facilitated scan of the user's ear, ensuring a secure and comfortable fit for the wearable device.

In some aspects, the leg module 3002, the shim module 3006, and the nose module 3008 may exhibit a variety of shapes, sizes, and dimensions to accommodate the diverse anatomical structures of users' ears. These modules may be connected to the jacket module 3004 at different relative locations to optimize the fit and retention of the wearable insert within the ear. For instance, the nose module 3008 may be positioned opposite the leg module 3002, adjacent to the leg module 3002, or on an orthogonal face relative to the leg module 3002, and the like, depending on the specific design requirements and the user's ear anatomy. In some cases, the nose module 3008 may be opposite the leg module 3002 and the shim module 3006 may be on an orthogonal face (e.g., 90 degrees perpendicular to the axis) between leg module 3002 and the shim module 3006.

The modules may include cavities that serve various purposes, such as housing an air shim or air gasket. These cavities may be strategically placed in different portions of the modules to enhance the comfort and adaptability of the insert. For example, the air shim may be located within the shim module 3006. In some cases, the nose module 3008 may include an air shim or air gasket. In some cases, the jacket module 3004 may include air shim or air gasket to provide increased compliance where it is beneficial for the fit and function of the device.

The shim module 3006 may be positioned off the center axis of the jacket module 3004 (e.g., to right or left from a center line of biometric sensor) and/or be positioned centrally or on one end of the jacket module 3004 (e.g., above, at or below, a mid line of the biometric sensor). The shim module 3006 may be specifically designed to fill the gap between the jacket module 3004 and the ear, particularly the antihelix. This off-axis design allows the shim module 3006 to conform to the curvature of the antihelix, providing a secure and stable fit while minimizing pressure points within the ear.

Furthermore, the legs of the leg module 3002 may vary in length, number, and compliance to ensure a secure engagement with the ear. The engagement portion 3104 of the leg module 3002 may feature a sloped surface that is designed to frictionally engage with the ear's anatomy, such as the antitragus, to prevent slippage and maintain the position of the insert.

The nose module 3008 may be shaped to conform to various surfaces of the ear and is attached off-axis from the sensor (e.g., to fill a gap between the jacket module and the ear surface) thereby providing support and stability to the insert. The off-axis attachment allows the nose module 3008 to apply a counterforce that aids in the proper alignment and positioning of the biometric sensor against the skin of the cymba concha, ensuring consistent sensor readings.

Figure 31:
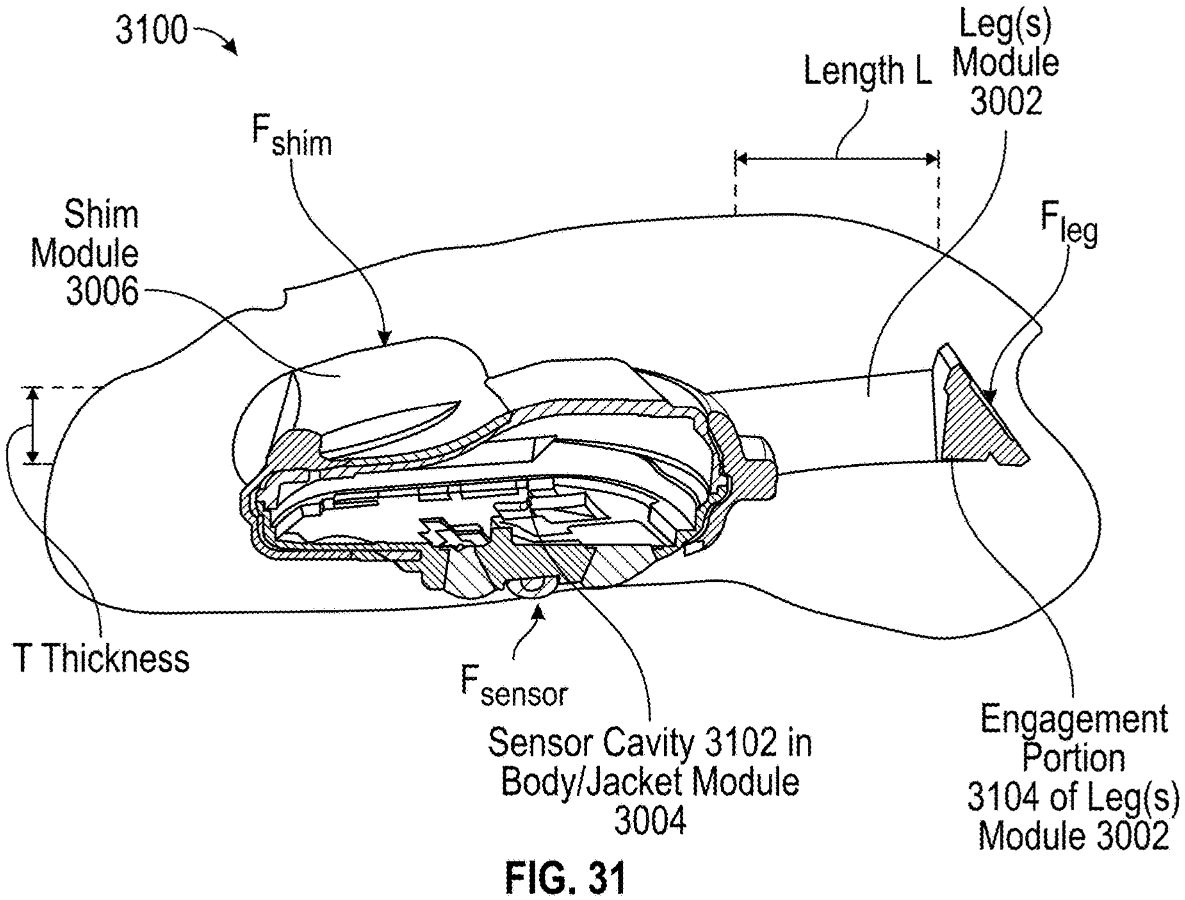
FIG. 31 shows an ear interface mechanism with adjustable modules, according to aspects of the present disclosure.

FIG. 31 depicts an isometric view of an ear interface mechanism 3100. The ear interface mechanism 3100 includes a shim module 3006, a leg(s) module 3002, and a body/jacket module 3004. Each of these modules plays a distinct role in the positioning and retention of the device within the user's ear.

The shim module 3006 is positioned to provide support and compliance against the ear structure. In some aspects, the shim module 3006 may be designed to conform to the shape of the antihelix 1706, providing a secure and comfortable fit. The shim module 3006 may be constructed with an air-filled cavity to increase its compliance, allowing for a more adaptable fit across different ear sizes. The shim module 3006 applies a first retention force to the device, contributing to the secure positioning of the device within the ear.

The leg(s) module 3002 extends into the ear, with an engagement portion 3104 designed to secure the mechanism by engaging with the ear anatomy. In some cases, the leg(s) module 3002 may include one or more legs that extend into the cavum concha. These legs are designed to tuck under the antitragus 1712 of the ear, providing additional retention for the ear interface mechanism 3100 within the ear. The leg(s) module 3002 applies a second retention force to the device, further ensuring its proper positioning and contact with the user's ear.

The body/jacket module 3004 houses a sensor cavity 3102, which is designed to hold and position the biometric sensor 101. In some aspects, the body/jacket module 3004 may be designed to protect the biometric sensor 101 from external forces and environmental conditions, ensuring the reliable operation of the sensor. The body/jacket module 3004 may also provide a comfortable fit for the user, as it may be constructed from a compliant material.

In some cases, the shim module 3006, the leg(s) module 3002, and the body/jacket module 3004 may be constructed from the same or different materials, depending on the desired properties of the ear interface mechanism 3100. For example, the shim module 3006 may be constructed from a more compliant material to provide comfort for the user, while the leg(s) module 3002 may be constructed from a more rigid material to provide structural support.

In some aspects, the shim module 3006, the leg(s) module 3002, and the body/jacket module 3004 may be selected from a plurality of respective modules having different sizes to fit the ear of the user. This selection may be based on a two-dimensional or three-dimensional smartphone-facilitated scan of the user's ear, ensuring a secure and comfortable fit for the wearable device. This modular design allows for a customizable fit for different users, accommodating the natural diversity of human ear shapes and sizes.

Figure 32:
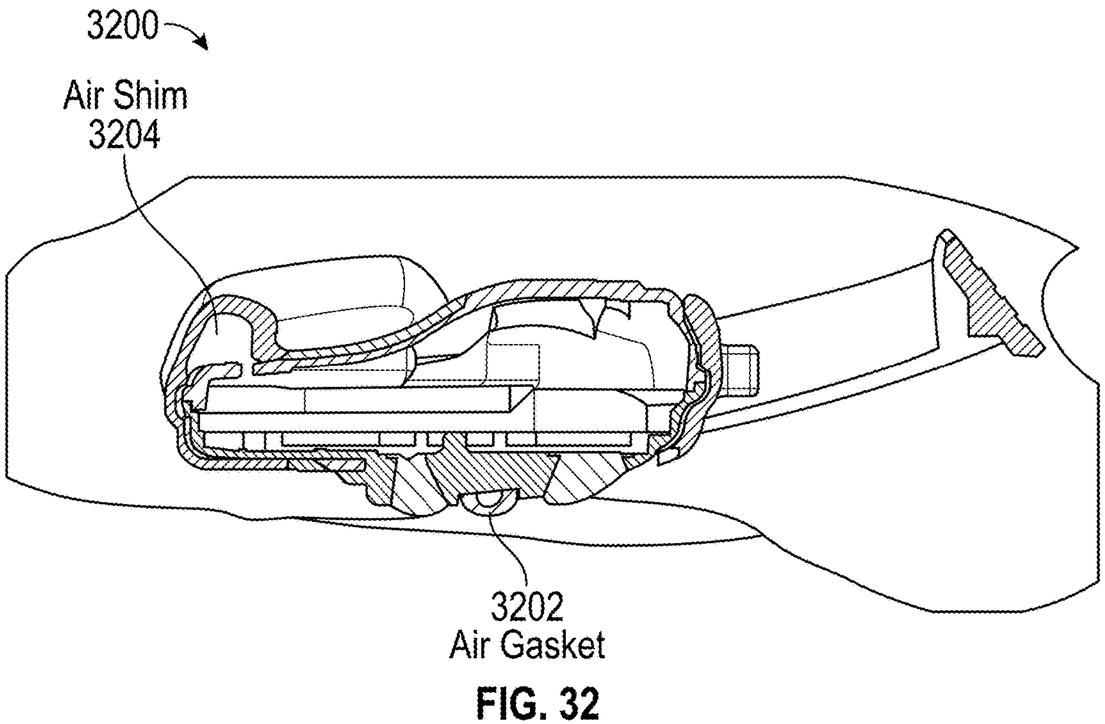
FIG. 32 provides a cross-sectional view of a wearable insert with an air gasket and air shim, according to aspects of the present disclosure.

FIG. 32 depicts a cross-sectional view of a wearable insert 3200. The wearable insert 3200 includes an air gasket 3202 and an air shim 3204, both of which contribute to the positioning and performance of the biometric sensor 101.

The air gasket 3202 is positioned below the wearable insert 3200. In some aspects, the air gasket 3202 may be designed to provide a light sealing function. This function is particularly beneficial when the biometric sensor 101 is an optical sensor, as it prevents emitted photons from escaping and ensures that the detector lens receives the maximum amount of light. The air gasket 3202 also provides a compliant surface so that the lens of the sensor presses against the skin of the user with an even force. This even force ensures that the biometric sensor 101 maintains consistent contact with the user's skin, allowing for accurate biometric readings. In some cases, the air gasket 3202 may be constructed with an air-filled cavity to increase its compliance. This increased compliance allows the air gasket 3202 to adapt to different ear curvatures, ensuring a secure and comfortable fit for different users.

The air shim 3204 is located above the wearable insert 3200. In some aspects, the air shim 3204 may be designed to ensure a secure and adaptable fit within the ear. The air shim 3204 may be constructed with an air-filled cavity to increase its compliance, allowing for a more adaptable fit across different ear sizes. The increased compliance of the air shim 3204 allows it to conform to the shape of the antihelix 1706, providing a secure and comfortable fit. The air shim 3204 applies a medial counterforce on the device body, contributing to the secure positioning of the wearable insert 3200 within the ear.

The relationship between the air gasket 3202 and the air shim 3204 ensures that the wearable insert 3200 is properly retained and positioned within the ear for the biometric sensor 101 to perform at its optimum. In some cases, the air gasket 3202 and the air shim 3204 may be constructed from the same or different materials, depending on the desired properties of the wearable insert 3200. For example, the air gasket 3202 and the air shim 3204 may be constructed from a compliant material to provide comfort for the user, while also providing the requisite structural support for the wearable insert 3200.

4.B. Flowchart

Figure 33:
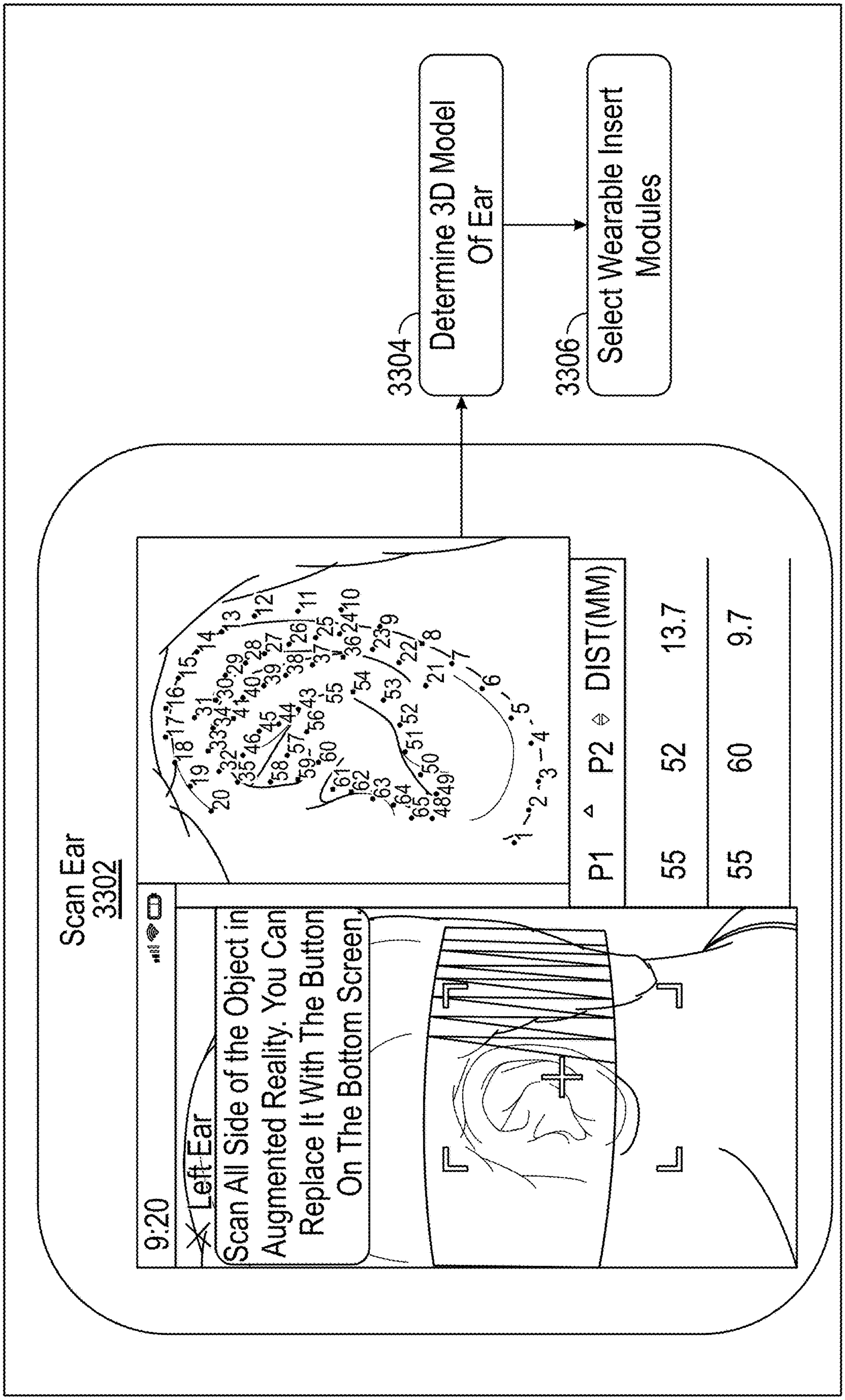
FIG. 33 presents a flowchart of a method for providing a wearable insert for a user, according to aspects of the present disclosure.

FIG. 33 depicts a flowchart 3300 for a method for providing a wearable insert for a user. This method involves scanning an ear of the user to obtain ear data, determining a two-dimensional rescaled image or three-dimensional reconstructed model of the ear based on the ear data, and selecting a wearable insert based on that 2D image or 3D model.

In some aspects, the scanning of the ear may be performed using a smartphone camera paired with 2D rescaling and 3D reconstruction techniques, such as photogrammetry. The scan ear 3302 process captures the detailed anatomical features of the user's ear, including the shape and size of the Cymba Concha, Antihelix, Antitragus, and other relevant ear structures. The ear scanning process may include adhering a coin for reference scaling in front of the ear. This process provides the basis for creating a two-dimensional rescaled and/or three-dimensional model of the user's ear.

The process of determining a two-dimensional rescaled or three-dimensional model of the ear, labeled as determine model of ear 3304, involves processing the ear data obtained from the scanning process. In some cases, this process may involve using the coin as a reference to rescale the image to physical millimeter measurement. In other cases, the process may involve the use of computer algorithms to reconstruct the ear data into a three-dimensional model. This model provides a detailed representation of the user's ear, allowing for the accurate selection and fitting of the wearable insert.

The final step in the method involves selecting wearable insert modules, labeled as select wearable insert modules 3306. This selection is based on either the two-dimensional rescaled or the three-dimensional model of the user's ear. In some aspects, the selection process may involve choosing a leg module, a nose module, and a shim module from a plurality of respective modules having different sizes. This modular design allows for a customizable fit for different users, accommodating the natural diversity of human ear shapes and sizes.

In some cases, the selection of the wearable insert modules may also take into account the type of biometric sensor to be used, the desired positioning of the sensor within the ear, and other factors relevant to the performance of the wearable insert. The selected modules are then assembled to form the wearable insert, which is designed to securely position the biometric sensor within the user's ear while ensuring its proper contact with the skin portion of the Cymba Concha for accurate biometric readings.

In some aspects, the method may also involve providing the wearable insert and the biometric sensor to the user, along with instructions for positioning the wearable insert within the ear. The user may then position the wearable insert within the ear according to the provided instructions, ensuring the proper positioning and contact of the biometric sensor with the skin portion of the Cymba Concha.

5. TERMINOLOGY

The terminology used above may be interpreted in its broadest reasonable manner, even though it is being used in conjunction with a detailed description of certain specific examples of the present disclosure. Indeed, certain terms may even be emphasized above; however, any terminology intended to be interpreted in any restricted manner will be overtly and specifically defined as such in this Detailed Description section. Both the foregoing general description and the detailed description are exemplary and explanatory only and are not restrictive of the features, as claimed.

Unless otherwise defined, all technical terms used herein have the same meaning as commonly understood by one of ordinary skill in the art to which this disclosure belongs.

As used herein, the singular forms "a," "an," and "the" include plural references unless the context clearly dictates otherwise. Any reference to "or" herein is intended to encompass "and/or" unless otherwise stated.

As used herein, the term "about" in some cases refers to an amount that is approximately the stated amount.

As used herein, the term "in-ear" in some cases refers to being on or attached to the ear of a subject. As used herein, the term "in-ear" in some cases refers to being inside the concha of the ear of a subject. As used herein, the term "in-ear" in some cases refers to being inside an ear canal of the subject.

As used herein, the term "about" refers to an amount that is near the stated amount by 10%, 5%, or 1%, including increments therein.

As used herein, the term "about" in reference to a percentage refers to an amount that is greater or less the stated percentage by 10%, 5%, or 1%, including increments therein.

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

As used herein, the terms "comprises," "comprising," "having," including," or other variations thereof, are intended to cover a non-exclusive inclusion such that a process, method, article, or apparatus that comprises a list of elements does not include only those elements, but may include other elements not expressly listed or inherent to such a process, method, article, or apparatus.

In this disclosure, relative terms, such as, for example, "substantially," "generally," and "approximately" are used to indicate a possible variation of +10% in a stated value. The term "exemplary" is used in the sense of "example" rather than "ideal."

6. EXAMPLES

Exemplary embodiments of the systems and methods disclosed herein are described in the numbered paragraphs below.

A1. A system for non-invasively measuring blood flow to a brain, the system comprising:

a biometric sensor configured to be removably retained against an external surface of a skin portion of a target location at a head of a user; and a processor and a memory storing computer instructions, wherein the system is configured to:

obtain, using the biometric sensor, biometric data relating to a blood flow waveform of one or more arteries near the target location;

determine, based on the biometric data relating to the biometric data and/or blood flow waveform of the one or more arteries near the target location, a parameter indicative of a blood flow to a brain of the user; and display or transmit the parameter indicative of the blood flow to the brain of the user;

wherein determining the parameter indicative of the blood flow to the brain of the user comprises performing one or more computations using the biometric data and/or the blood flow waveform of the one or more arteries at the target location, the one or more computations being statistically determined by:

obtaining sample target location biometric data relating to sample blood flow waveforms of one or more sample arteries within ears of a plurality of sample subjects;

obtaining sample brain biometric data relating to one or more brains of the plurality of sample subjects;

for each of at least a subgroup of the plurality of sample subjects, pairing the sample ear biometric data to the sample brain biometric data obtained for a respective sample subject to create a plurality of sample data pairs; and based on the sample data pairs, determine one or more relationships between the sample ear biometric data and the sample brain biometric data.

A2. The system of A1, wherein the one or more computations are performed by a machine learning model that has been trained based on the plurality of sample data pairs to identify the one or more relationships between the sample biometric data and the sample brain biometric data.

A3. The system of any of A1-A2, wherein the sample brain biometric data comprises a plurality of diffuse correlation spectroscopy measurements of frontal lobe perfusion of the plurality of sample subjects.

A4. The system of any of A1-A3, wherein the sample brain biometric data comprises a plurality of transcranial Doppler ultrasound measurements of middle cerebral arteries of the plurality of sample subjects.

A5. The system of any of A1-A4, wherein the sample brain biometric data comprises a plurality of ultrasound measurements of carotid and/or vertebral arteries of the plurality of sample subjects.

A6. The system of any of A1-A5, wherein the sample brain biometric data comprises a plurality of ultrasound measurements of carotid and/or vertebral arteries of the plurality of sample subjects, and the parameter indicative of the blood flow to the brain of the user is carotid flow time.

A7. The system of any of A1-A6, wherein the target location is an ear of the user to target a posterior auricular artery of the user, a temple of the user to target a superficial temporal artery of the user, or an underside of a wrist of the user to target a radial artery of the user.

A8. The system of any of A1-A7, wherein the biometric sensor is configured to be anchored to an ear of the user.

A9. The system of A8, wherein the biometric sensor is configured to be anchored at a cymba concha of the user.

A10. The system of any of A1-A6, wherein the target location is within the ear of the user, and the biometric sensor is attached to a polymeric insert comprising an aperture through which the biometric sensor emits light, wherein, when the polymeric insert is positioned within the ear of the user, the aperture is less than five (5) millimeters from a branch of the posterior auricular artery.

A11. The system of A10, wherein the branch emerges at an anterior face of the user's ear within seven (7) millimeters of a helical root of the user's ear, and the polymeric insert is at least partially disposed at the base of the helical root.

A12. The system of any of A1-A11, wherein the parameter indicative of the blood flow to the brain of the user is cerebral blood flow, blood flow to a head of the user, carotid blood flow, stroke volume (SV), and/or cardiac output (CO).

A13. The system of any of A1-A12, wherein the biometric sensor is an optical sensor, and the optical sensor uses photoplethysmography, laser doppler flowmetry, or laser speckle contrast imaging.

A14. The system of any of A1-A12, wherein the biometric sensor is an ultrasound transducer or photoacoustic transducer.

A15. The system of any of A1-A12, wherein the biometric sensor is an RF transducer.

A16. The system of any of A1-A15, wherein determining the parameter indicative of the blood flow to the brain of the user is performed by an integrated hardware device that includes the biometric sensor and is configured to be disposed at the target location of the user.

A17. The system of any of A1-A16, wherein the one or more computations comprise one or more of: (1) analyzing a fullness of the blood flow waveform of the one or more arteries near the target location; (2) determining an area under a systolic period of a cardiac pulse in the blood flow waveform of the one or more arteries near the target location; and (3) determining an assessment of a time period from a start of systole to a dichrotic notch of a cardiac pulse in a carotid artery of the user.

A18. The system of any of A1-A17, wherein the sample brain biometric data relates to one of: (i) sample blood flow wave forms within the one or more brains of the plurality of sample subjects, or (ii) cognitive function data relating to the plurality of sample subjects.

A19. A computer-implemented method comprising:

obtaining, using a biometric sensor, biometric data relating to a blood flow waveform of one or more arteries near a target location of a user;

determining, based on the biometric data relating to the blood flow waveform of the one or more arteries near the target location, a parameter indicative of a blood flow to a brain of the user; and displaying or transmitting the parameter indicative of the blood flow to the brain of the user;

wherein determining the parameter indicative of the blood flow to the brain of the user comprises performing one or more computations using the biometric data and/or the blood flow waveform of the one or more arteries near the target location.

A20. The computer-implemented method of A19, wherein the one or more computations comprise one or more of: (1) analyzing a fullness of the blood flow waveform of the one or more arteries near the target location; (2) determining an area under a systolic period of a cardiac pulse in the blood flow waveform of the one or more arteries near the target location; and (3) determining an assessment of a time period from a start of systole to a dichrotic notch of the cardiac pulse in a carotid artery of the user.

B1. A wearable photoplethysmography system (wearable PPG system) configured to be placed at a target location of a user, the wearable PPG system comprising:

a wearable device configured engage a body portion of the user;

an emitter configured to emit photons having a wavelength of at least 590 nanometers;

a photodiode;

a lens cavity adjacent to the emitter; and at least one lens disposed within the lens cavity;

wherein, when the wearable PPG system is placed at the target location of the user:

the at least one lens is configured to direct at least 75% of the photons within an exit angle range between 30 and 90 degrees, the exit angle range being defined relative to a surface plane of the wearable PPG system;

the wearable device disposes the emitter and lens such that an arterial bed is less than 5 millimeters from an exit surface of the lens and within a path defined by the exit angle range, the arterial bed being between 0.6 millimeters and 5 millimeters from an external surface of the skin of the user, the arterial bed comprising a portion of a posterior auricular artery, a superficial temporal artery, or a radial artery of the user; and at least a portion the photons emitted by the emitter penetrates a tissue of the user, interacts with the arterial bed, and is then redirected to and detected by the photodiode.

B2. The wearable PPG system of B1, wherein the target location is an ear of the user to target a posterior auricular artery of the user, a temple of the user to target a superficial temporal artery of the user, or an underside of a wrist of the user to target a radial artery of the user.

B3. The wearable PPG system of B2, wherein the arterial bed comprises a branch of the posterior auricular artery.

B4. The wearable PPG system of B3, wherein the branch emerges at an anterior face of the user's ear within seven (7) millimeters of a helical root of the user's ear.

B5. The wearable PPG system of B2, wherein, when the wearable PPG system is placed at the target location, the exit surface of the lens is less than 5 millimeters from a branch of the posterior auricular artery that perforates an auricular cartilage to protrude at an anterior face of the ear of the user.

B6. The wearable PPG system of B5, wherein the branch protrudes from a base of a helical root of the ear of the user, and the exit surface is positioned at the base of the helical root.

B7. The wearable PPG system of any of B1-B6, wherein the lens directs more than 90% of the photons within the exit angle range.

B8. The wearable PPG system of any of B1-B7, wherein the lens cavity comprises one or more reflective surfaces configured to reflect at least 50% of a plurality of photons that contact the one or more reflective surfaces.

B9. The wearable PPG system of B8, wherein the emitter is configured to emit the photons in a diffuse lambertian pattern, and the one or more reflective surfaces form one or more off-axis parabolic reflectors configured to increase a collimation parameter of the plurality of photons that contact the one or more reflective surfaces.

B10. The wearable PPG system of any of B1-B9, further comprising a light absorbing gasket that at least partially absorbs misaligned photons emitted by the emitter, the misaligned photons being emitted at angles below the exit angle range.

B11. The wearable PPG system of any of B1-B10, further comprising one or more detector cavities in which the photodiode is disposed.

B12. The wearable PPG system of any of B1-B11, wherein the lens cavity comprises one or more low-index surfaces having a refractive index that is lower than a refractive index of the lens, wherein a boundary between the lens and the one or more low-index surfaces promotes total internal reflection of at least a portion of the photons emitted by the emitter.

B13. The wearable PPG system of any of B1-B12, wherein an input face of the lens that abuts the emitter is curved or disposed at a transverse angle relative to a surface plane of a housing of the PPG system, the curve and/or transverse angle of the input face being configured to increase a percentage of photons that exit the lens within the exit angle range.

B14. The wearable PPG system of any of B1-B13, wherein the surface plane of the wearable PPG system is defined by a housing of the wearable PPG system, and the exit surface of the lens protrudes beyond the surface plane such that, when the wearable PPG system is placed at the target location, the exit surface of the lens contacts the external surface of the skin of the user.

B15. The wearable PPG system of any of B1-B14, wherein the lens comprises an elastomeric material having a Shore A durometer hardness of less than Shore 70 A.

B16. The wearable PPG system of any of B1-B15, wherein the emitter is a light emitting diode.

B17. The wearable PPG system of any of B1-B15, wherein the emitter is a vertical cavity surface emitting laser.

B18. A method for monitoring blood flow in an arterial bed of a user using a wearable photoplethysmography system (wearable PPG system), the method comprising:

placing the wearable PPG system at a target location of the user such that an exit surface of a lens of the wearable PPG system is less than 5 millimeters from the arterial bed and the arterial bed is within a path defined by an exit angle range between 30 and 90 degrees relative to a surface plane, wherein the arterial bed is between 0.6 millimeters and 5 millimeters from an external surface of the skin of the user;

emitting photons from an emitter of the wearable PPG system, wherein the photons have a wavelength of at least 590 nanometers;

directing at least 75% of the photons within the exit angle range to the arterial bed of the user, wherein the photons interact with the arterial bed; and receiving, by to a photodiode, redirected photons that have interacted with the arterial bed, wherein the photodiode detects the redirected photons.

B19. The method of B18, wherein the target location is an ear of the user to target a posterior auricular artery of the user, a temple of the user to target a superficial temporal artery of the user, or an underside of a wrist of the user to target a radial artery of the user.

B20. The method of B19, wherein the arterial bed comprises an arterial branch of an external carotid artery.

C1. A wearable insert for positioning a biometric sensor at least partially within a cymba concha of an ear of a user, the wearable insert comprising:

a first insert portion configured to abut an antihelix of the ear of the user;

a second insert portion configured to be disposed at least partially within a cymba cavum of the ear; and a cavity configured to hold the biometric sensor;

wherein, when the wearable insert is positioned within the ear:

an engagement between the first insert portion and the antihelix applies a first retention force vector to the wearable insert, the first retention force vector being oriented at least partially medially;

an engagement between the second insert portion and an ear portion against which the second insert portion abuts applies a second retention force vector to the wearable insert; and at least the first retention force vector and the second retention force vector retain the wearable insert such that the biometric sensor is pressed medially toward an external surface of a skin portion of the cymba concha of the ear.

C2. The wearable insert of C1, wherein the second insert portion comprises one or more legs that, when the wearable insert is positioned within the ear, extend into a cavum concha to tuck under a antitragus of the ear.

C3. The wearable insert of C2, wherein the cavity of the wearable insert is enclosed by a jacket portion, and the one or more legs are attached to the jacket portion.

C4. The wearable insert of C3, wherein the jacket portion is attached to a leg module, a shim module, and a nose module.

C5. The wearable insert of C4, wherein the jacket portion is removable from the biometric sensor by a user, allowing for easy adjustment to a different combination of the leg module, the nose module, and the shim module.

C6. The wearable insert of C4, wherein the leg module, the nose module, and the shim module are each selected from a plurality of respective modules having different sizes to fit the ear of the user.

C7. The wearable insert of any of claims C1-C6, wherein the second retention force vector is oriented at least partially medially.

C8. The wearable insert of any of C1-C7, wherein the wearable insert comprises a shim that, when the wearable insert is positioned within the ear, extends along and contacts a length of at least 4 millimeters of the antihelix.

C9. The wearable insert of C8, wherein the shim is constructed with an air-filled cavity that increases a compliance of the shim.

C10. The wearable insert of any of C1-C9, wherein the wearable insert comprises a nose portion that, when the wearable insert is positioned within the ear, is disposed between a helix and the external surface of the skin portion of the cymba concha of the ear.

C11. The wearable insert of any of C1-C10, wherein the second insert portion comprises electronic circuitry configured to perform one or more functions unrelated to biometric sensing.

C12. The wearable insert of C11, wherein the electronic circuitry is configured to play sound using a speaker.

C13. The wearable insert of any of C1-C12, wherein the biometric sensor comprises an optical sensor.

C14. The wearable insert of any of C1-C13, wherein the wearable insert comprises an aperture that, when the wearable insert is positioned within the ear, is positioned (i) less than five (5) millimeters from a branch of a posterior auricular artery that perforates an auricular cartilage that protrudes at an anterior face of the ear, and (ii) between the cavity of the wearable insert and the external surface of the skin portion of the cymba concha of the ear.

C15. The wearable insert of any of C1-C14, wherein the wearable insert comprises a light-sealing gasket.

C16. The wearable insert of C15, wherein the light-sealing gasket is constructed with an air-filled cavity that increases a compliance of the light-sealing gasket.

C17. A method for providing a wearable insert for a user, the method comprising:

scanning an ear of the user to obtain ear data;

determining a two-dimensional rescaled or three-dimensional reconstructed model of the ear based on the ear data;

selecting a wearable insert based on the two-dimensional or three-dimensional model; and providing the wearable insert and a biometric sensor to the user, wherein the wearable insert is configured to position the biometric sensor at least partially within a cymba concha of the ear;

wherein the wearable insert includes a first insert portion configured to abut an antihelix of the ear, a second insert portion configured to be disposed at least partially within a cymba cavum of the ear, and a cavity configured to hold the biometric sensor.

C18. The method of C17, further comprising selecting a leg module, a nose module, and a shim module from a plurality of respective modules having different sizes based on the two-dimensional or three-dimensional reconstructed model of the ear.

C19. The method of C17, wherein, when the wearable insert is positioned within the ear: (1) an engagement between the first insert portion and the antihelix applies a first retention force vector to the wearable insert, the first retention force vector being oriented at least partially medially; (2) an engagement between the second insert portion and an ear portion against which the second insert portion abuts applies a second retention force vector to the wearable insert; and (3) at least the first retention force vector and the second retention force vector retain the wearable insert such that the biometric sensor is pressed medially toward an external surface of a skin portion of the cymba concha of the ear.

C20. The method of C17, wherein the wearable insert comprises an aperture that, when the wearable insert is positioned within the ear, is positioned (i) less than five (5) millimeters from a branch of a posterior auricular artery that perforates an auricular cartilage that protrudes at an anterior face of the ear, and (ii) between the cavity of the wearable insert and an external surface of a skin portion of the cymba concha of the ear.

Other aspects of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A wearable photoplethysmography system (wearable PPG system) configured to be placed at a target location of a user, the wearable PPG system comprising:

a wearable device configured to engage a body portion of the user;

an emitter configured to emit photons having a wavelength of at least 590 nanometers;

a photodiode;

a lens cavity adjacent to the emitter; and at least one lens disposed within the lens cavity;

wherein, when the wearable PPG system is placed at the target location of the user:

the at least one lens is configured within the lens cavity relative to the emitter such that at least 75% of the photons emitted by the emitter are directed within an exit angle range between 30 and 90 degrees, the exit angle range being defined relative to a surface plane of the wearable PPG system;

the wearable device disposes the emitter and lens such that an arterial bed is less than 5 millimeters from an exit surface of the lens and within a path defined by the exit angle range, the arterial bed being between 0.6 millimeters and 5 millimeters from an external surface of the skin of the user; and at least a portion of the photons emitted by the emitter penetrates a tissue of the user, interacts with the arterial bed, and is then redirected to and detected by the photodiode; and a light absorbing gasket that at least partially absorbs misaligned photons emitted by the emitter, the misaligned photons being emitted at angles below the exit angle range.

2. The wearable PPG system of claim 1, wherein the target location is an ear of the user to target a posterior auricular artery of the user.

3. The wearable PPG system of claim 2, wherein the arterial bed comprises a branch of the posterior auricular artery.

4. The wearable PPG system of claim 3, wherein the branch emerges at an anterior face of the user's ear within seven (7) millimeters of a helical root of the user's ear.

5. The wearable PPG system of claim 2, wherein, when the wearable PPG system is placed at the target location, the exit surface of the lens is less than 5 millimeters from a branch of the posterior auricular artery that perforates an auricular cartilage to protrude at an anterior face of the ear of the user.

6. The wearable PPG system of claim 5, wherein the branch protrudes from a base of a helical root of the ear of the user, and the exit surface is positioned at the base of the helical root.

7. The wearable PPG system of claim 1, wherein the lens directs more than 90% of the photons within the exit angle range.

8. The wearable PPG system of claim 1, wherein the lens cavity comprises one or more reflective surfaces configured to reflect at least 50% of a plurality of photons that contact the one or more reflective surfaces.

9. The wearable PPG system of claim 8, wherein the emitter is configured to emit the photons in a diffuse lambertian pattern, and the one or more reflective surfaces form one or more off-axis parabolic reflectors configured to increase a collimation parameter of the plurality of photons that contact the one or more reflective surfaces.

10. The wearable PPG system of claim 1, further comprising one or more detector cavities in which the photodiode is disposed.

11. The wearable PPG system of claim 1, wherein the lens cavity comprises one or more low-index surfaces having a refractive index that is lower than a refractive index of the lens, wherein a boundary between the lens and the one or more low-index surfaces promotes total internal reflection of at least a portion of the photons emitted by the emitter.

12. The wearable PPG system of claim 1, wherein an input face of the lens that abuts the emitter is curved or disposed at a transverse angle relative to a surface plane of a housing of the PPG system, the curve and/or transverse angle of the input face being configured to increase a percentage of photons that exit the lens within the exit angle range.

13. The wearable PPG system of claim 1, wherein the surface plane of the wearable PPG system is defined by a housing of the wearable PPG system, and the exit surface of the lens protrudes beyond the surface plane such that, when the wearable PPG system is placed at the target location, the exit surface of the lens contacts the external surface of the skin of the user.

14. The wearable PPG system of claim 1, wherein the lens comprises an elastomeric material having a Shore A durometer hardness of less than Shore 70A.

15. The wearable PPG system of claim 1, wherein the emitter is a light emitting diode.

16. The wearable PPG system of claim 1, wherein the emitter is a vertical cavity surface emitting laser.

17. The wearable PPG system of claim 1, wherein the arterial bed comprises a portion of a posterior auricular artery.

* * * * *